United States Patent
Suzumura et al.

[11] Patent Number: 5,719,778
[45] Date of Patent: Feb. 17, 1998

[54] HEATER CONTROL APPARATUS FOR OXYGEN SENSOR

[75] Inventors: Toshihiro Suzumura, Nagoya; Shigenori Isomura, Kariya; Tomomichi Mizoguchi, Nagoya; Yukihiro Yamashita; Jun Hasegawa, both of Kariya, all of Japan

[73] Assignee: Nippondenso Co., Ltd., Kariya, Japan

[21] Appl. No.: 500,423

[22] Filed: Jul. 10, 1995

[30] Foreign Application Priority Data

| Aug. 5, 1994 | [JP] | Japan | 6-184847 |
| Dec. 22, 1994 | [JP] | Japan | 6-320623 |
| Feb. 10, 1995 | [JP] | Japan | 7-022503 |
| Mar. 22, 1995 | [JP] | Japan | 7-062746 |

[51] Int. Cl.$^6$ ................................. G06F 14/00
[52] U.S. Cl. .................... 364/477.01; 364/431.05
[58] Field of Search ............... 364/477.01, 431.05, 364/431.04, 148, 153, 166; 123/676, 689; 204/406, 408

[56] References Cited

U.S. PATENT DOCUMENTS

| 4,538,575 | 9/1985 | Chujo et al. | 123/440 |
| 4,543,176 | 9/1985 | Harada et al. | 204/40 |
| 4,611,562 | 9/1986 | Nakano et al. | 123/440 |
| 4,708,777 | 11/1987 | Kuraoka | 204/421 |
| 4,825,838 | 5/1989 | Osuga et al. | 123/489 |
| 4,873,642 | 10/1989 | Mieno et al. | 364/431.06 |
| 5,111,792 | 5/1992 | Nagai et al. | 123/440 |
| 5,148,795 | 9/1992 | Nagai et al. | 123/697 |
| 5,214,267 | 5/1993 | Hoshi et al. | 219/497 |
| 5,227,975 | 7/1993 | Nakaniwa | 364/431.05 |
| 5,291,673 | 3/1994 | Hamburg | 60/274 |
| 5,547,552 | 8/1996 | Hasegawa et al. | 123/440 |

FOREIGN PATENT DOCUMENTS

| 3842287 | 8/1989 | Germany . |
| 61-132851 | 6/1986 | Japan . |
| 63-249046 | 10/1988 | Japan . |

*Primary Examiner*—Paul P. Gordon
*Attorney, Agent, or Firm*—Cushman, Darby & Cushman IP Group of Pillsbury, Madison & Sutro LLP

[57] ABSTRACT

In a heater control of an oxygen sensor, a heater control circuit is rendered fully conductive at 100% duty initially to supply full power to a heater until the resistance value of the heater reaches a predetermined initial value corresponding to a predetermined temperature. Then, the duty of the heater control circuit is feedback controlled so that the heater temperature becomes a target value until the internal resistance of the oxygen sensor reaches a target temperature, and further, after the internal resistance of the oxygen sensor S reaches the target temperature, the duty of the heater control circuit is feedback controlled so that the element temperature of the sensor becomes a target value.

38 Claims, 41 Drawing Sheets

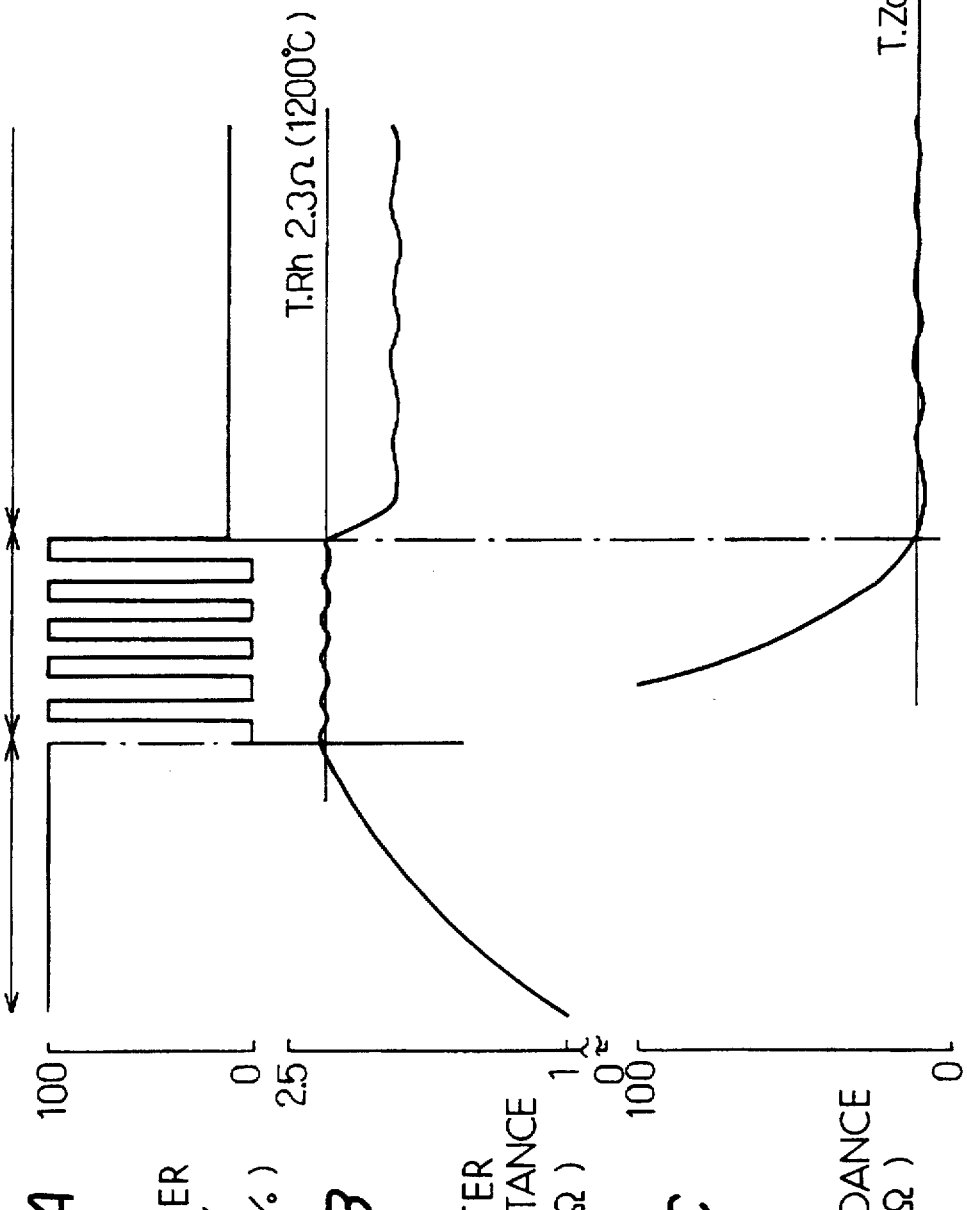

FIG. 14

| PM (mmHg) / NE (rpm) | 200 | 400 | 600 |
|---|---|---|---|
| 1000 | 683 | 709 | 736 |
| 2000 | 709 | 762 | 814 |
| 3000 | 736 | 814 | 893 |

FIG. 16

| NE*PM ($\times 10^5$) | 5 | 6 | 7 | 8 | 9 | 10 |
|---|---|---|---|---|---|---|
| TIME CONST. $\tau_1$ | 168 | 155 | 142 | 128 | 115 | 102 |
| TIME CONST. $\tau_2$ | 26 | 24 | 22 | 20 | 18 | 16 |

FIG.15A (5w)

| PM (mmHg) / NE (rpm) | 200 | 400 | 600 |
|---|---|---|---|
| 1000 | -142 | -137 | -132 |
| 2000 | -137 | -127 | -118 |
| 3000 | -132 | -118 | -104 |

FIG.15B (15w)

| PM (mmHg) / NE (rpm) | 200 | 400 | 600 |
|---|---|---|---|
| 1000 | 142 | 137 | 132 |
| 2000 | 137 | 127 | 118 |
| 3000 | 132 | 118 | 104 |

FIG.15C (25w)

| PM (mmHg) / NE (rpm) | 200 | 400 | 600 |
|---|---|---|---|
| 1000 | 409 | 395 | 382 |
| 2000 | 395 | 368 | 343 |
| 3000 | 382 | 343 | 305 |

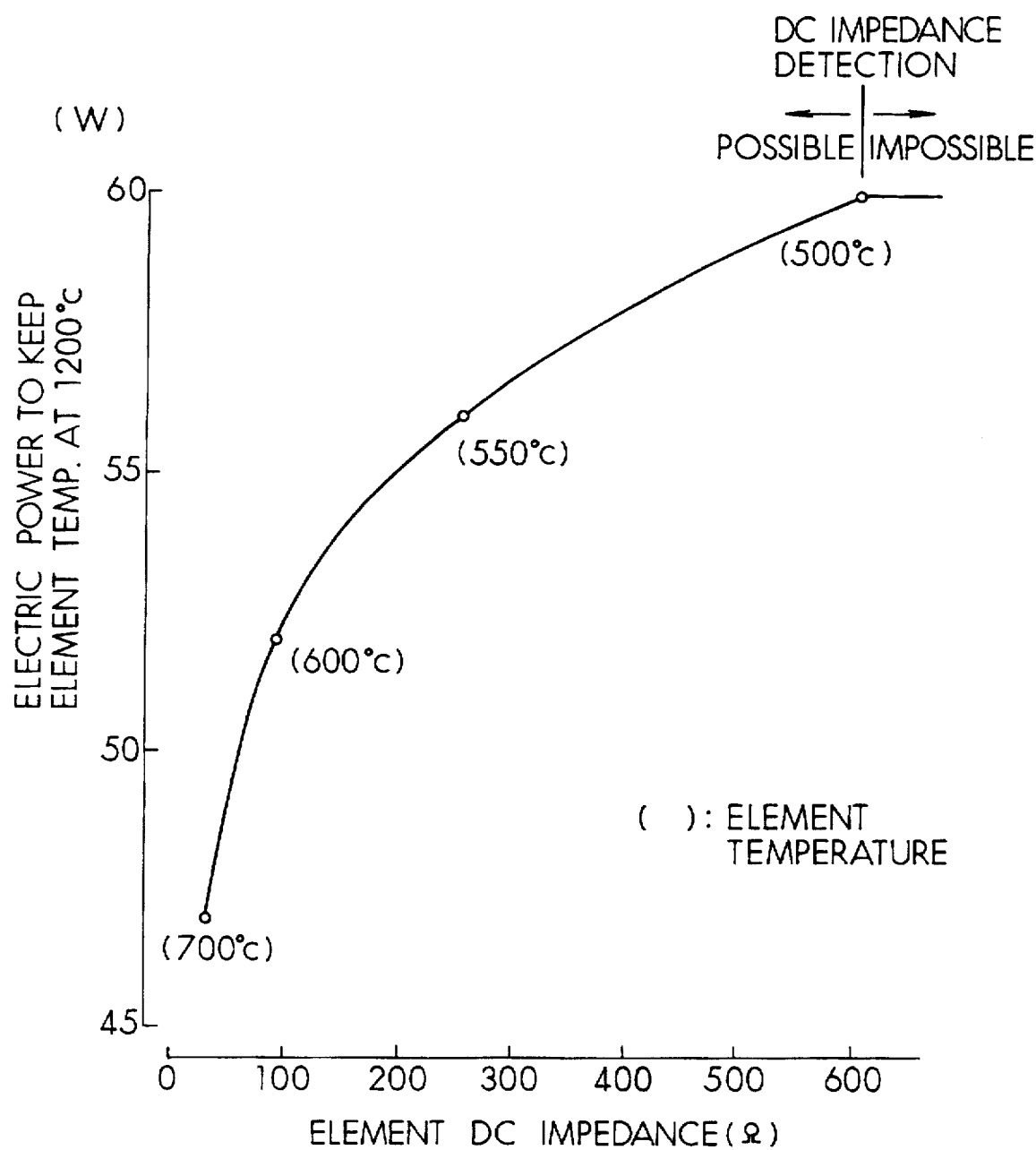

810 — FULL CONDUCT CONTROL
811 — XEFP = 1
812 — HDUTY = 100%
RET

820 — POWER CONTROL
821 — XEFP = 0, XEWAT = 1
822 — DETECT ZDC
823 — WHTG (W) vs ZDC (Ω)
824 — HDUTY = WHTG/WH(%)
RET

FIG. 43

| ELEMENT (Ω) \ HEATER (Ω) | 0.9 | 1.0 | 1.1 | 1.2 | ..... |
|---|---|---|---|---|---|
| 600 | LARGE | ...... | ...... | ...... | MEDIUM |
| 500 | ..... | ...... | ...... | ...... | ...... |
| 400 | ...... | ...... | ...... | ...... | ...... |
| 200 | MEDIUM | ...... | ...... | ...... | SMALL |
| 100 | 0 | 0 | 0 | 0 | 0 |
| 0 | 0 | 0 | 0 | 0 | 0 |

HEATER CONTROL APPARATUS FOR OXYGEN SENSOR

CROSS REFERENCE TO RELATED APPLICATIONS

This application is based on and claims priorities of Japanese Patent Applications No. 6-184847 filed on Aug. 5, 1994, No. 6-320623 filed on Dec. 22, 1994, No. 7-22503 filed on Feb. 10, 1995 and No. 7-62746 filed on Mar. 22, 1995, the contents of which are incorporated herein by reference.

BACKGROUND OF THE INVENTION

1. Field of the Invention

The present invention relates to an apparatus for controlling heating of a heater of an oxygen sensor for detecting an air-fuel ratio, i.e. oxygen density, in the exhaust gas of an internal combustion engine.

2. Description of Related Art

Conventionally, there are those among this type which, as well as noting changes in the internal resistance of a limited current type oxygen sensor and the resistance value of a heater according to temperature and supplying an electric power determined by the operating conditions of an internal combustion engine, control the power supply to the heater according to the internal resistance of the oxygen sensor and the resistance value of the heater, as shown in Unexamined Japanese Patent Publication No. S61-132851 for example.

Also, for example, there are those which control the power supply to the heater such that full power is supplied to the heater from a power source from commencement of current supply to the heater till the internal resistance of the oxygen sensor and the resistance value of the heater becomes a predetermined value corresponding to a predetermined temperature, whereafter the internal resistance of the sensor becomes a predetermined value corresponding to a predetermined temperature, as shown in Unexamined Japanese Patent Publication No. S63-249046.

However, in the former of the prior art described above there has been the problem that power supplied to the heater at commencement of current supply cannot place the sensor in an active state in a short period since it is set so that it cannot become an excess power.

Also, in the latter of the prior art described above, at the commencement of current supply, although full power is supplied to the heater, upon full power being supplied to the heater until the internal resistance of the sensor reaches a predetermined value, there is the possibility that durability is reduced due to wire breakage etc. of the heater, and there is also the problem that, upon supply of full power to the heater until the resistance value of the heater reaches the predetermined value, it is affected by the surrounding environment such as exhaust gas temperature and the like, the element temperature becomes too high or too low, and element temperature control at the commencement of current supply is likely to become insufficient.

SUMMARY OF THE INVENTION

The present invention, having been made to deal with such problems, has an object to favorably perform a heater element temperature control at the commencement of current supply and place an oxygen sensor in an active state in a short time, while preventing wire breakage to a heater and improving its durability.

According to the present invention, a heater control apparatus for an oxygen sensor includes, as shown in FIG. 1, element temperature detection means for detecting an element temperature of an oxygen sensor, a heater for heating the oxygen sensor, and heater temperature detection means for detecting a temperature of the heater. It further includes power supply means for supplying power in the vicinity of full power from a power source in the heater from commencement of current supply to the heater until a temperature of the heater reaches an initial heating temperature. It further includes heater temperature responsive current supply control means for controlling supply of current to the heater according to a heater temperature detected by the heater temperature detection means upon the temperature of the heater reaching the initial heating temperature by heating of the heater by the full electrical power supply means. It still further includes element temperature responsive current supply control means for controlling current supply to the heater according to the element temperature detected by the element temperature detection means upon the element temperature detected by the element temperature detection means reaching a predetermined value by heating of the heater by the heater temperature response current supply control means.

Thus, the electric power in the vicinity of full power is supplied to the heater by the power supply means from commencement of current supply to the heater till the temperature of the heater reaches the initial heating temperature, whereafter, upon the temperature of the heater reaching the initial heating temperature, the current supply to the heater is controlled by the heater temperature responsive current supply control means according to the temperature of the heater, after which the current supply to the heater is controlled by the element temperature responsive current supply control means according to the element temperature upon the element temperature of the oxygen sensor reaching the predetermined value.

BRIEF DESCRIPTION OF THE DRAWINGS

In the accompanying drawings:

FIGS. 4A, 4B, and 4C are time charts explaining the operation of the first embodiment;

FIG. 14 is a data map showing a steady heater temperature data;

FIGS. 15A, 15B and 15C are data maps showing power-corrected heater temperature data;

FIG. 16 is a map showing time constant data;

FIG. 23 is a characteristic graph showing the required power supply for maintaining the heater at 1200° C.;

FIG. 43 is a characteristic graph showing a target cumulative power supply with respect to an initial value of heater resistance and initial element impedance;

DETAILED DESCRIPTION OF THE PREFERRED EMBODIMENTS

The present invention will be described hereinunder with respect to various embodiments shown in the accompanying drawings.

[Embodiment 1]

Figure 1:
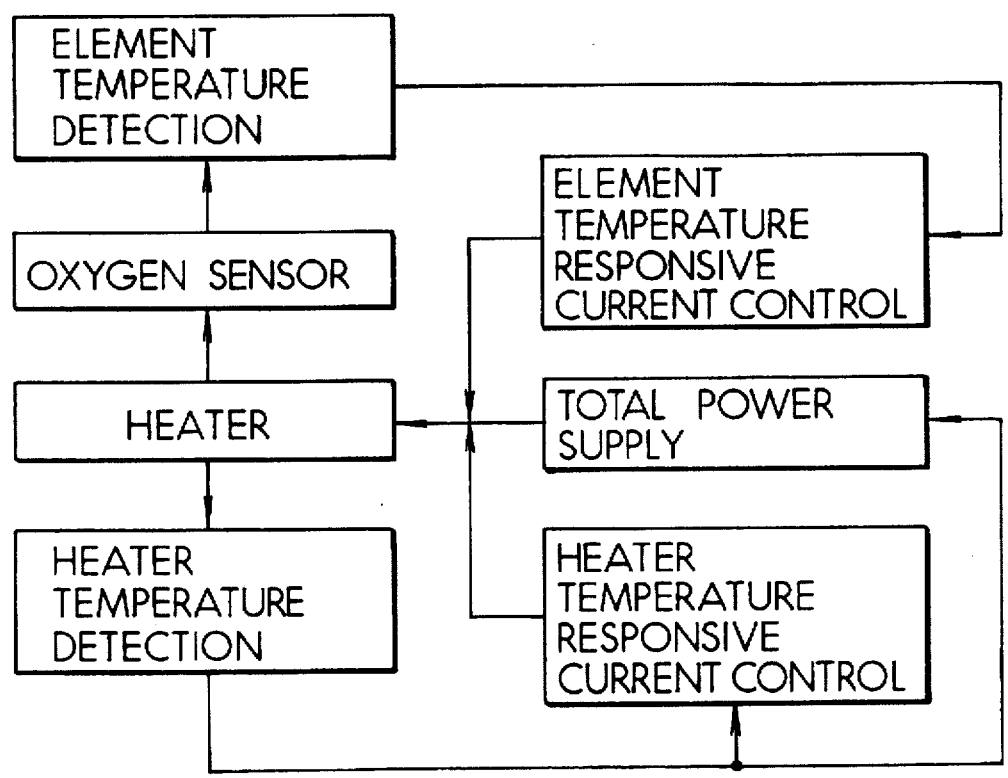
FIG. 1 is a block diagram showing the present invention.
Figure 2:
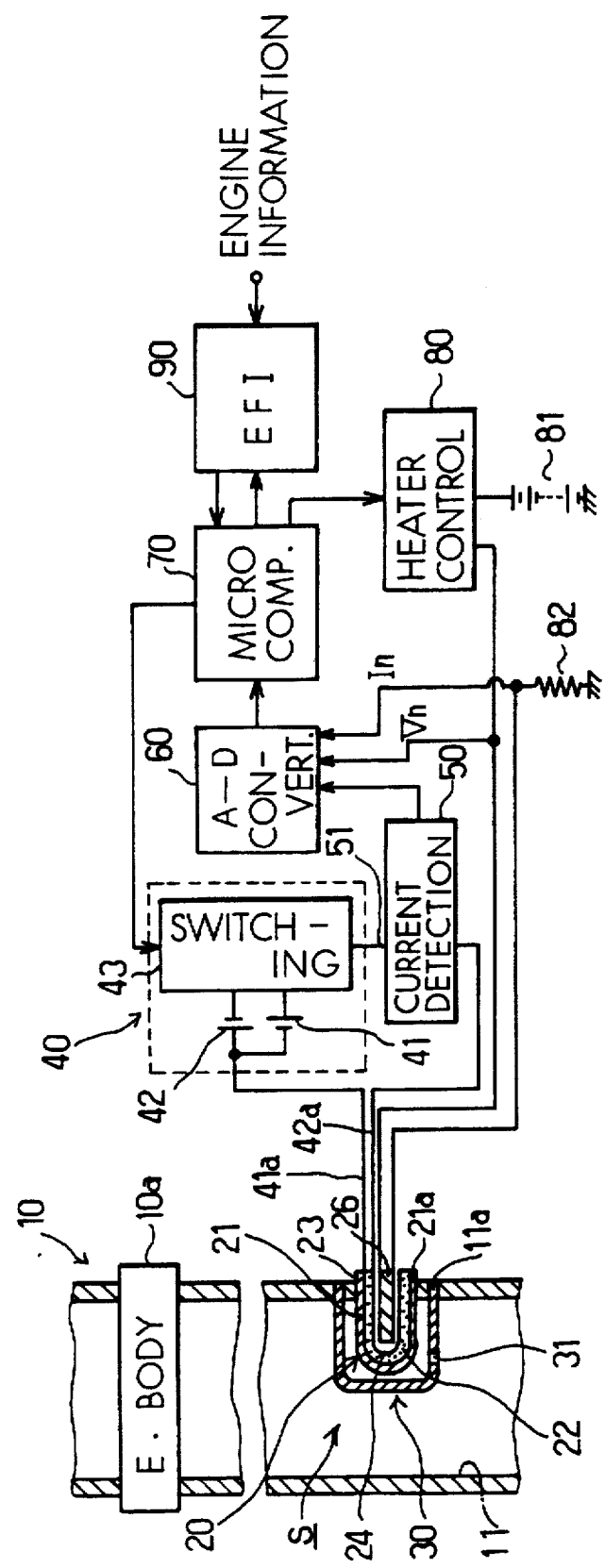
FIG. 2 is a block circuit diagram showing a first embodiment of the present invention.

Herebelow, a first embodiment of the present invention will be explained with reference to FIG. 2 showing an oxygen density detecting apparatus applied to an internal combustion engine 10 and mounted in an automobile. The oxygen density detecting apparatus comprises a limit current supply type oxygen sensor S, this oxygen sensor S being attached in an exhaust pipe 11 extending outward from a main engine body 10a of the internal combustion engine 10. The oxygen sensor S is constructed by a sensor main body 20 and a cross-sectional C-shaped cover 30, the sensor main body 20 being fitted into an attachment hole portion 11a provided in one portion of a surrounding wall of the exhaust pipe 11 at the base end portion thereof, extending outward while facing the inner portion of the exhaust pipe 11.

Figure 3A:
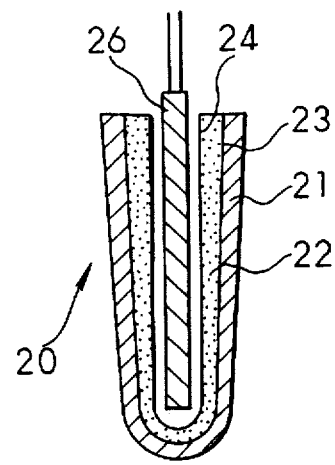
FIG. 3A is an enlarged cross-section view of a sensor main body of the oxygen sensor of FIG. 2.

The oxygen sensor 20, shown in detail in FIG. 3A, has a cross-sectional cup-shaped diffusion resistor layer 21, this diffusion resistance layer 21 being fitted into the attachment hole portion 11a of the exhaust pipe 11 at an opening end portion 21a thereof. The diffusion resistance layer 21 is formed by a plasma spraying method or the like of $ZrO_2$, etc. Also, the sensor main body 20 has a solid electrolyte layer 22, this solid electrolyte layer 22 being formed in a cross-sectional cup shape by an oxygen ion-conductive oxide sintered body, uniformly fitted to an inner peripheral wall of the diffusion resistance layer 21 via a cross-sectional cup-shaped exhaust gas-side electrode layer 23, and having an atmosphere-side electrode layer 24 uniformly fixed in a cross-sectional cup shape to an inner surface of this solid electrolyte layer 22. In this case, the exhaust-side electrode layer 23 and atmosphere-side electrode layer 24 are formed to be sufficiently porous by chemically plating a noble metal having high catalytic activity such as platinum or the like. Also, the area and thickness of the exhaust gas-side electrode layer 23 are in the order of 10 to 100 $mm^2$ and 0.5 to 2.0μ, while the area and thickness of the atmosphere-side electrode layer are 10 $mm^2$ or more and in the order of 0.5 to 2.0μ.

The sensor main body 20 thus constructed generates variable density electromotive force at a theoretical or stoichiometric air-fuel ratio point to generate a limit current according to a lean region oxygen density from the theoretical air-fuel ratio point. In this case, the limit current corresponding to the oxygen density is determined by the area of the exhaust gas-side electrode 23, the thickness of the diffusion resistance layer 21, air hole rate and average hole diameter. Also, although the sensor main body 20 can detect oxygen density by its linear characteristic, as well as a high temperature of approximately 650° C. or more being required to activate the sensor main body 20, because the activation temperature range of the sensor main body 20 is narrow, it cannot control an activation region during heating only by means of the exhaust gas of the internal combustion engine. Due to this, heating control by a heater 26 described later is used. It is to be noted that in a richer region than the theoretical air-fuel ratio, the density of carbon monoxide (CO), which is an unburned gas, changes substantially linearly to the air-fuel ratio and the limit current is generated according thereto.

Here, explaining the voltage-current characteristic of the sensor main body 20, which takes the temperature of the sensor main body 20 as a parameter, this voltage-current characteristic shows that a relationship between a current flowing into the solid electrolyte layer 22 of the sensor main body 20 and a voltage applied to the solid electrolyte layer 22, which is proportional to the detected oxygen concentration (air-fuel ratio) of the oxygen sensor S, is linear. Then, when the sensor main body 20 is in the active state at temperature T=T1, it exhibits a stable state as shown by the solid line in the characteristic graph L1 in FIG. 3B. In this case, the linear portion of the characteristic graph L1, which is parallel to a voltage axis V, specifies the limit current of the sensor main body 20. Then, the increase/decrease of this limit current corresponds to the decrease/increase (i.e. lean/rich) of the air-fuel ratio. Also, when the temperature T of the sensor main body 20 is at T2, which is lower than T1, the current-voltage characteristic is specified by the broken line in the characteristic graph L2 shown in FIG. 3B. In this case, a linear portion of the characteristic graph L2 which is parallel to the voltage axis V specifies the limit current of the sensor main body 20 at T=T2 and this limit current substantially corresponds to the limit current of the characteristic graph L1.

Figure 3B:
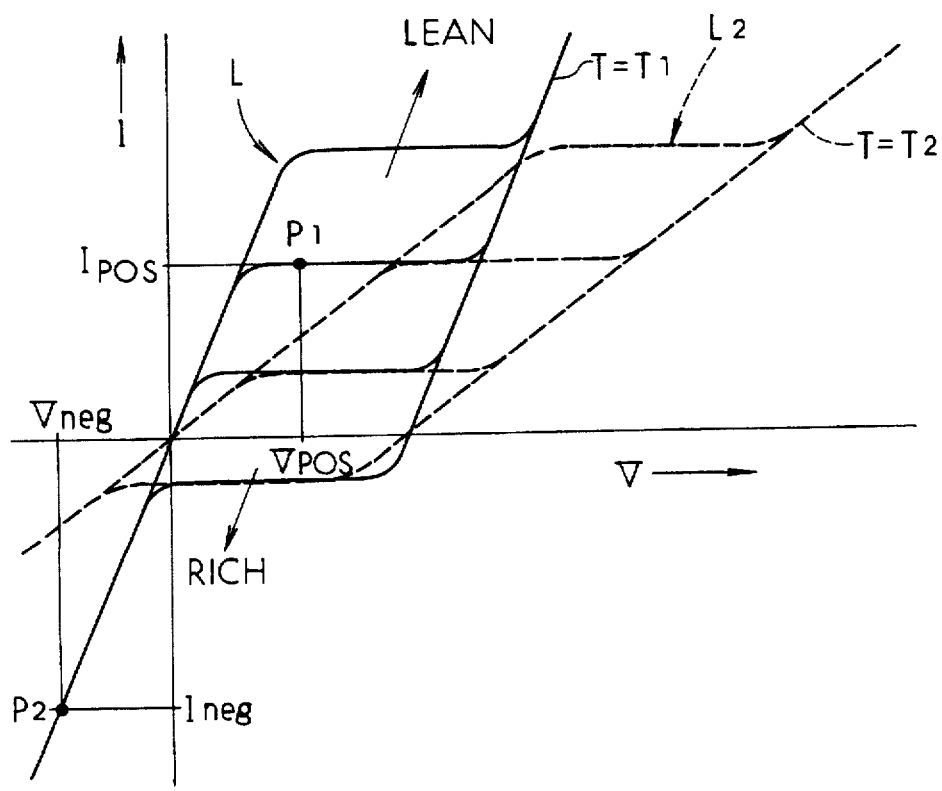
FIG. 3B is a graph showing the limit current-voltage characteristic of the oxygen sensor with temperature as a parameter.

Also, in the characteristic graph L1, when a positive applied voltage Vpos is applied to the solid electrolyte layer 22 of the sensor main body 20, the current flowing through the sensor main body 20 becomes a limit current Ipos (refer to point P1 in FIG. 3B). In addition, when a negative applied voltage Vneg is applied to the solid electrolyte layer 22 of the sensor main body 20, the current flowing through the sensor main body 20 becomes a negative current Ineg which is not dependent on the oxygen concentration but is proportional only to temperature and which is specified by a point P2.

Also, the sensor main body 20 comprises the heater 26, which is accommodated within the atmosphere side electrode layer 24, for heating the atmosphere side electrode layer 24, the solid electrolyte layer 22, the exhaust gas side electrode layer 23 and the diffusion resistance layer 21 by means of its exothermic energy. In this case, the heater 26 has a heating capacity sufficient to activate the sensor main body 20. The cover 30 covers the sensor main body 20 and is attached to a portion of the peripheral wall of the exhaust pipe 11 at its opening portion. A small hole 31 is perforated through a part of the peripheral wall of the cover 30 so that the outside of the cover 30 can communicate with the inside thereof. As a result, the cover 30 thermally shields the sensor main body 20 while preventing the sensor main body 20 from coming into direct contact with the exhaust gas.

Also, the oxygen concentration detecting apparatus, as shown in FIG. 2, comprises a bias control circuit 40, this bias control circuit 40 being formed by a DC (direct current) power source for positive bias 41, a DC power source for negative bias 42 and a switch circuit 43. The DC power source 41 is connected to one end of the exhaust gas side electrode layer 23 via a lead wire 41a at its negative side electrode and the DC power source 42 is connected to one end of the exhaust gas side electrode layer 23 via the lead wire 41a at its positive side electrode. The switch circuit 43 connects only the positive side electrode of the DC power source 41 to an input terminal 51 of a current detecting circuit 50 in its first switching state and, in its second switching state, connects only the negative side electrode of the DC power source 42 to the input terminal 51 of the current detecting circuit 50, then is connected from the input terminal 51 to the atmosphere side electrode layer 24 via the current detecting circuit 50 and a lead wire 42a. Accordingly, when the switch circuit 43 is in the first switching state, the DC power source 41 positively biases the solid electrolyte layer 22 and circulates the current in the positive direction through the solid electrolyte layer 22. On the other hand, when the switch circuit 43 is in the second switching state, the DC power source 42 negatively biases the solid electrolyte layer 22 and circulates the current in the negative direction through the solid electrolyte layer 22. In this case, the terminal voltages of the DC power sources 41 and 42 correspond respectively to the applied voltages Vpos and Vneg described above.

The current detecting circuit 50 detects the current flowing from the atmosphere side electrode layer 24 of the sensor main body 20 to the switch circuit 43 or that flowing in the opposite direction, i.e. the current flowing through the solid electrolyte layer 22, and outputs it to an A/D converter 60. The A/D converter 60 converts the detected current from the current detecting circuit 50 into digital and outputs to a microcomputer 70. The microcomputer 70 comprises a CPU, ROM, RAM, etc. not shown in FIG. 2 and executes a computer program in cooperation with the A/D converter 60, during which execution, it performs an arithmetic process necessary for driving and controlling a heater control circuit 80 and a fuel injection control apparatus (hereinafter referred to as an EFI) 90. The above-mentioned computer program is primarily stored in the ROM of the microcomputer 70.

Also, the heating control circuit 80 performs heating control of the heater 26 according to the heater element temperature of the oxygen sensor S under the control of the microcomputer 70 by turning the power supplied to the heater 26 from a battery 81 serving as a power source on and off to control the duty. Also, the current In flowing through the heater 26 is detected by a current detection resistor 82 and supplied to the A/D converter 60. It is to be noted that the EFI 90 performs fuel injection control according to internal combustion engine information such as the amount of exhaust gas, engine rotations, air intake flow amount, negative pressure of the air intake, cooling water temperature, etc. of the internal combustion engine 10, under the control of the microcomputer 70.

Figure 38:
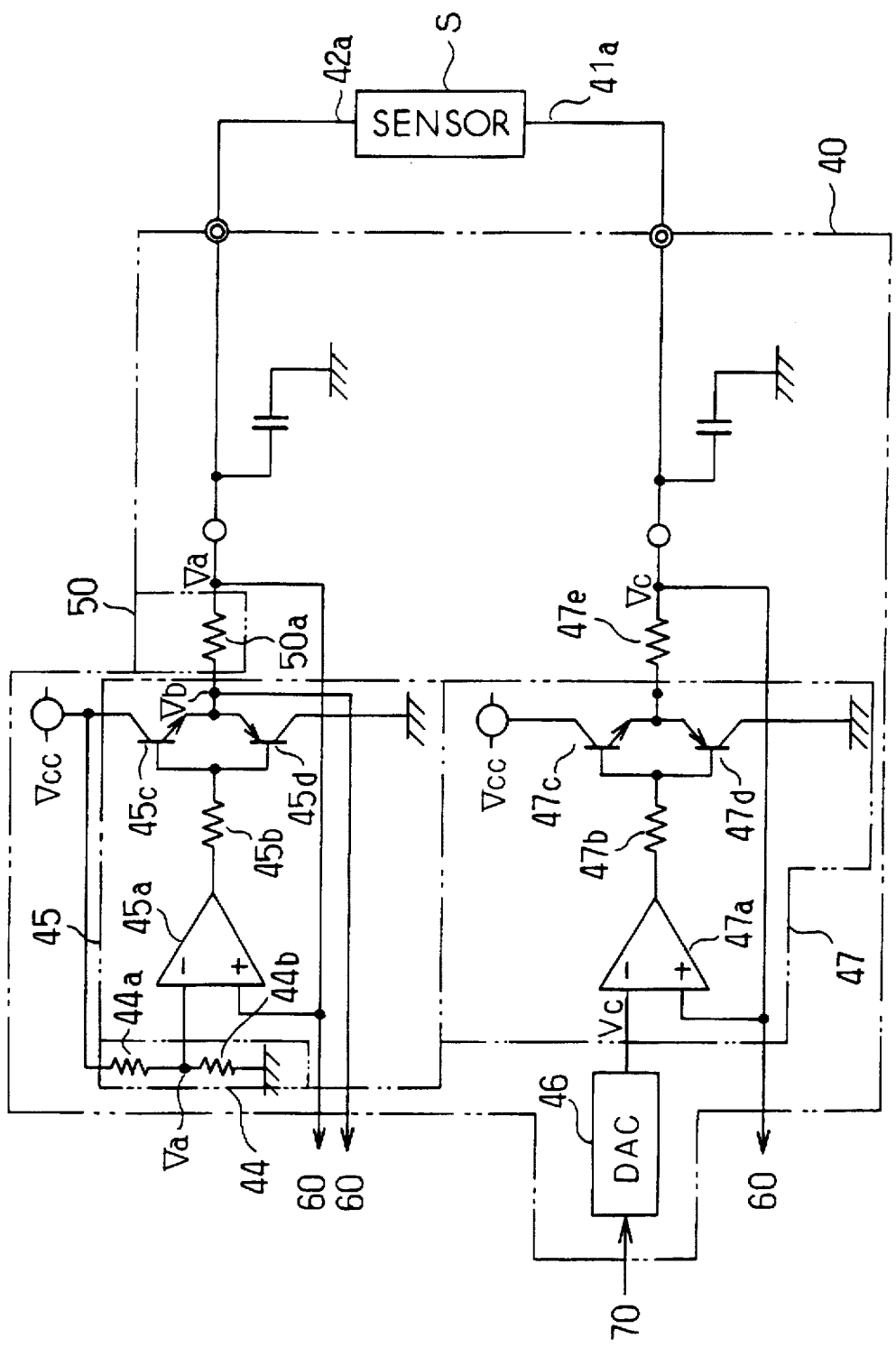
FIG. 38 is an electrical circuit diagram showing the detailed structure of a bias control circuit.

FIG. 38 shows the detailed electrical circuit structure of the bias control circuit 40, in which a reference voltage circuit 44 voltage-divides the constant voltage Vcc to produce a constant reference voltage Va by means of voltage dividing resistors 44a and 44b. A first voltage supply circuit 45 for supplying a voltage Va which is the same as the reference voltage Va of the reference voltage circuit 44 to one terminal of the oxygen sensor S (lead wire 42a connected to oxygen side electrode layer 24), and is formed by an operational amplifier 45a whose negative input terminal is connected to voltage dividing point of the voltage dividing resistors 44a and 44b and whose positive input terminal is connected to one terminal of the oxygen sensor S, resistor 45b one terminal of which is connected to the output terminal of the operational amplifier 45a and an NPN transistor 45c and PNP transistor 45d whose bases are connected to the other terminal of the resistor 45b.

Also, the collector of the NPN transistor 45c is connected to the constant voltage Vcc and the emitter thereof is connected to one terminal of the oxygen sensor S via a current detection resistor 50a which forms the current detection circuit 50, while the emitter of the PNP transistor 45d is connected to the emitter of the NPN transistor 45c and the collector thereof is grounded.

The D/A converter 46 converts a bias instruction signal (digital signal) from the microcomputer 70 to an analog signal voltage Vc. A second voltage supply circuit 47, for supplying a voltage Vc which is the same as the output voltage Vc of the D/A converter 46 to the other terminal (lead wire 41a connected to exhaust side electrode layer 23) of the oxygen sensor S, is formed by an operational amplifier 47a whose negative input terminal is connected to the output of the D/A converter 46 and whose positive input terminal is connected to the other terminal of the oxygen sensor S, a resistor 47b one end of which is connected to the output terminal of the operational amplifier 47a, and NPN transistor 47c and PNP transistor 47d whose bases are connected to one end of the resistor 47b.

Also, the collector of the NPN transistor 47c is connected to the constant voltage Vcc and the emitter thereof is connected to the other terminal of the oxygen sensor S via a resistor 47e, while the emitter of the PNP transistor 47d is connected to the emitter of the NPN transistor 47c and the collector thereof is grounded.

By means of the above, a continuous constant voltage Va is supplied to one terminal of the oxygen sensor S and a bias instruction signal equivalent to a voltage lower than the constant voltage Va is supplied from the microcomputer 70 to the D/A converter 46, whereby a voltage Vc lower than the constant voltage Va is supplied to the other terminal of the oxygen sensor S and the oxygen sensor S is positive biased by a voltage Va–Vc (Va>Vc), and by supplying a bias instruction signal equivalent to a voltage higher than the constant voltage Va is supplied from the microcomputer 70 to the D/A converter 46, a voltage Vc higher than the constant voltage Va is supplied to the other terminal of the oxygen sensor S and the oxygen sensor S is negative biased by the voltage Va–Vc (Va<Vc). Thereby, it is possible to control the bias voltage of the oxygen sensor S to a positive or negative arbitrary value based on the bias instruction supplied to the D/A converter 46 from the microcomputer 70.

Also, a voltage difference (Vb–Va) of both terminals of the current detection resistor 50a is input as a detection current from the current detection circuit 50 to an A/D converter 60 and a voltage difference (Va–Vc) of both terminals of the oxygen sensor S is input as an element voltage of the oxygen sensor S to the A/D converter 60.

Figure 5:
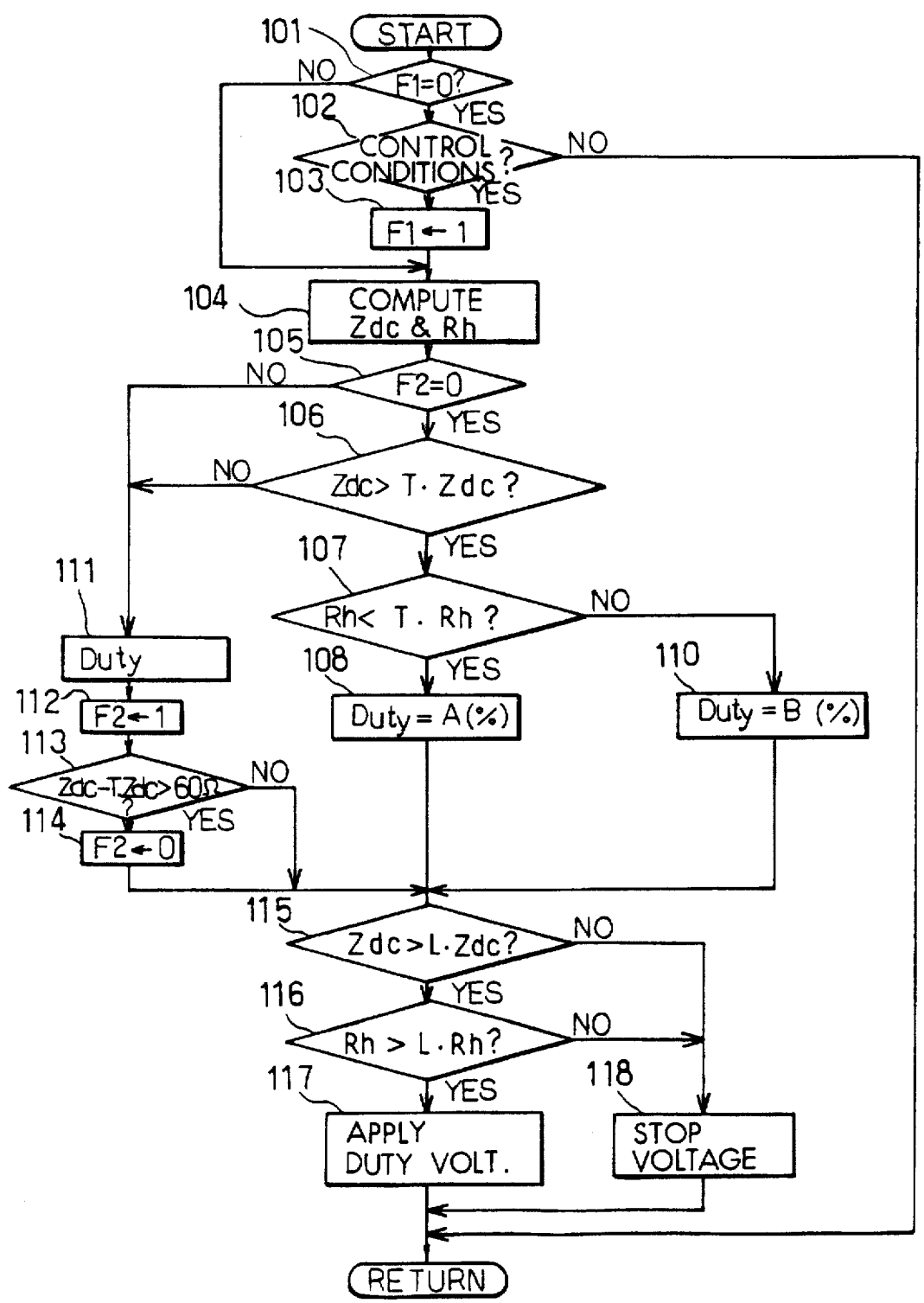
FIG. 5 is a flow chart showing an operation of a microcomputer of FIG. 2.

An explanation will be made using FIGS. 4A–4C and 5 regarding heater control executed in the first embodiment. FIGS. 4A through 4C show time charts after commencement of power supply to the heater accompanying the start of the internal combustion engine till the oxygen sensor S is fully activated, and FIG. 5 shows a flow chart which is repeatedly executed by the microcomputer 70 at predetermined intervals under the operation of the internal combustion engine 10 (since measurement of oxygen density is known from U.S. Pat. No. 4,543,176 (Japanese Unexamined Patent Publication No. S59-163556) for example, explanation thereof will be omitted here for brevity).

In FIGS. 4A through 4C, immediately after an electric power is input to the heater 26, a heater control circuit 80 is controlled at 100% duty to supply full power to the heater 26 from a battery 81 to rapidly heat it. This is called heater full current supply control and is period (1) of FIGS. 4A through 4C. At this time, by means of a negative current Ineg detected by the sensor current detection circuit 50 and a heater current In detected by a current detection resistor 82, a sequential element direct current impedance (internal resistance) and heater resistance are calculated.

Before the element direct current impedance reaches a target element direct current impedance equivalent to a complete activation temperature of the oxygen sensor S, where a detected heater resistance reaches a target heater resistance value equivalent to the heater being at 1200° C. (equivalent to initial setting temperature set at a somewhat lower value than the limit heat resistance temperature), the heater voltage is duty-controlled by the heater control circuit 80 and feedback-controlled so as to become the target heater resistance value. This is called heater upper limit temperature hold control. This is the period (2) in FIGS. 4A through 4C.

Thereafter, upon the element direct current impedance reaching the target direct current impedance, the heater upper limit temperature hold control executed up till then is finished and the heater voltage is duty-controlled by the heater control circuit 80 such that it becomes a target element direct current impedance. This is called element temperature feedback control. This is the period (3) in FIGS. 4A through 4C.

Thereafter, until the engine stops, this element temperature feedback control is basically continued. The above is a heater control method after heater power input and until complete activation of the oxygen sensor S.

Next, heater control executed by the microcomputer 70 will be explained according to the flow chart of FIG. 5. In the present embodiment, the operation cycle of this flow chart is 100 ms. First, in step 101 it is determined whether a flag F1 is "0" or not. Whether heater control has already been executed is determined by this flag F1. Where YES has been determined in step 101, since heater control has not yet been accomplished, step 102 is proceeded to and it is determined whether execution conditions for heater control have been established. Where NO is determined in step 101 the process skips steps 102 and 103 and proceeds to step 104.

The heater control execution conditions in step 102 are considered conditions such as: (1) whether the ignition switch is on, (2) whether a predetermined time tsec has elapsed or not after commencement of operation, (3) whether an alternator has commenced generating electricity, etc. In the present embodiment, control is performed under the condition of (1). In other words, heater control is initiated when the ignition switch is ON. However, after the ignition switch is ON, time is required until the microcomputer 70 reaches commencement of operation, in which case the microcomputer 70 commences heater control when it reaches a standby state.

Where YES is determined in step 102, step 103 is proceeded to and the flag F1 is set to "1". In other words, execution of heater control is indicated. In the next step 104, an element direct current impedance Zdc and heater resistance Rh are calculated as Zdc=Vneg/Ineg and Rh=Vn/In by the applied voltage Vn of the heater 26, element applied voltage Vneg, negative current Ineg detected by the sensor current detection circuit 50 and the heater current In detected by the current detection resistor 82.

Figure 6:
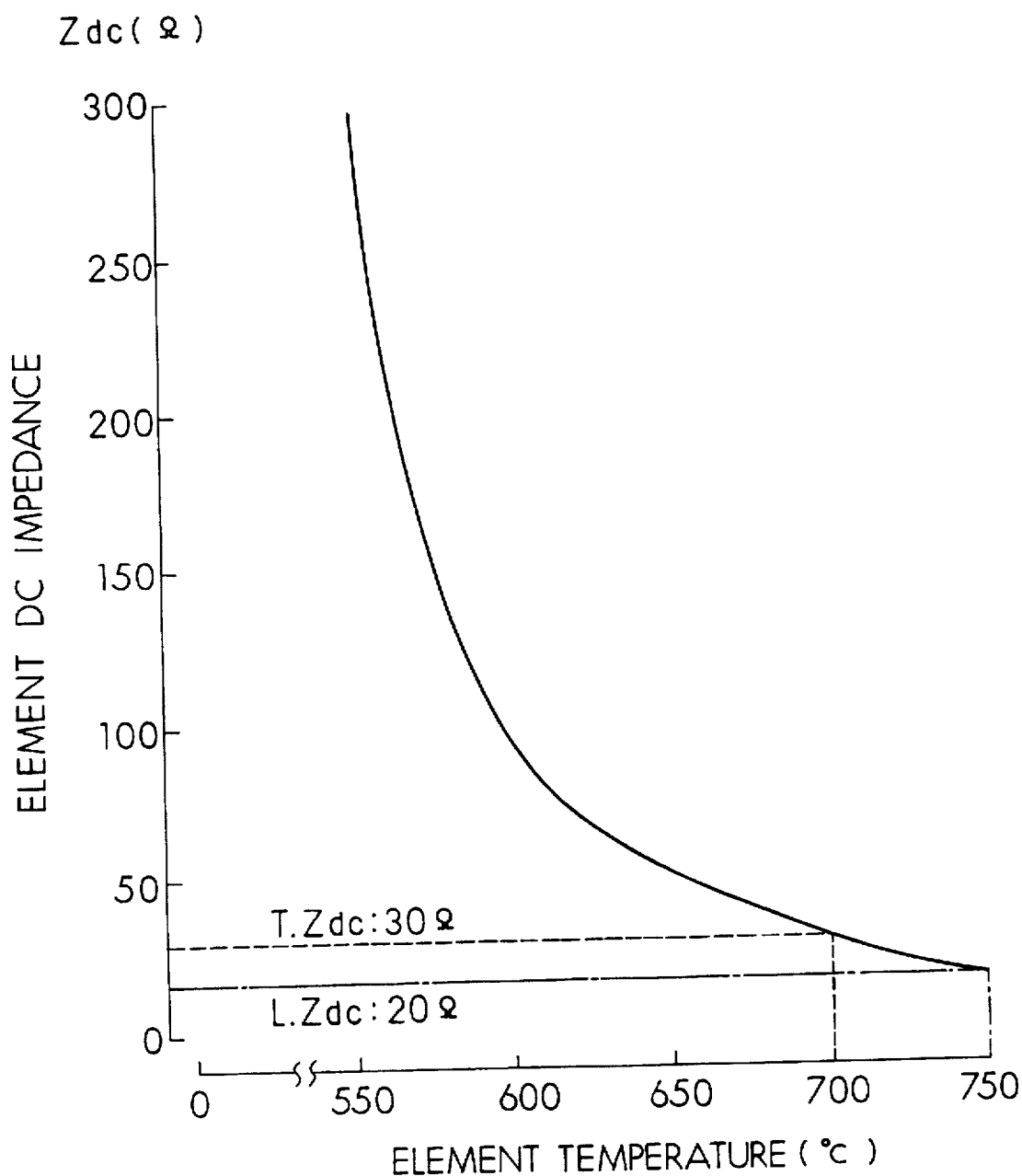
FIG. 6 is a characteristic diagram showing the relationship between element temperature and element direct current.

In the next step 105 whether a flag F2 is "0" or not is determined. The flag F2 indicates whether or not heater control is performing element temperature feedback. Where YES is determined in step 105, i.e. when not in a state of element temperature feedback, step 106 is proceeded to. In step 106, it is determined whether or not Zdc calculated in step 104 is larger than a target element direct current impedance T.Zdc. Here, the relationship between the element temperature and the element direct current impedance Zdc is shown in FIG. 6.

In the present embodiment, T.Zdc is set at 30Ω equivalent to the element temperature 700° C. where the oxygen sensor S is in a complete activation state. In other words, step 106 is where it is determined whether the oxygen sensor S is in a complete activation state or not. Where Zdc is greater than T.Zdc (where the element temperature is low and not in a complete activation state), heater full current supply control or heater upper limit temperature hold control is executed and functions to heat the oxygen sensor S.

When YES is determined in step 106, step 107 is proceeded to and when NO is determined, step 111 is proceeded to and element temperature feedback is executed.

Figure 7:
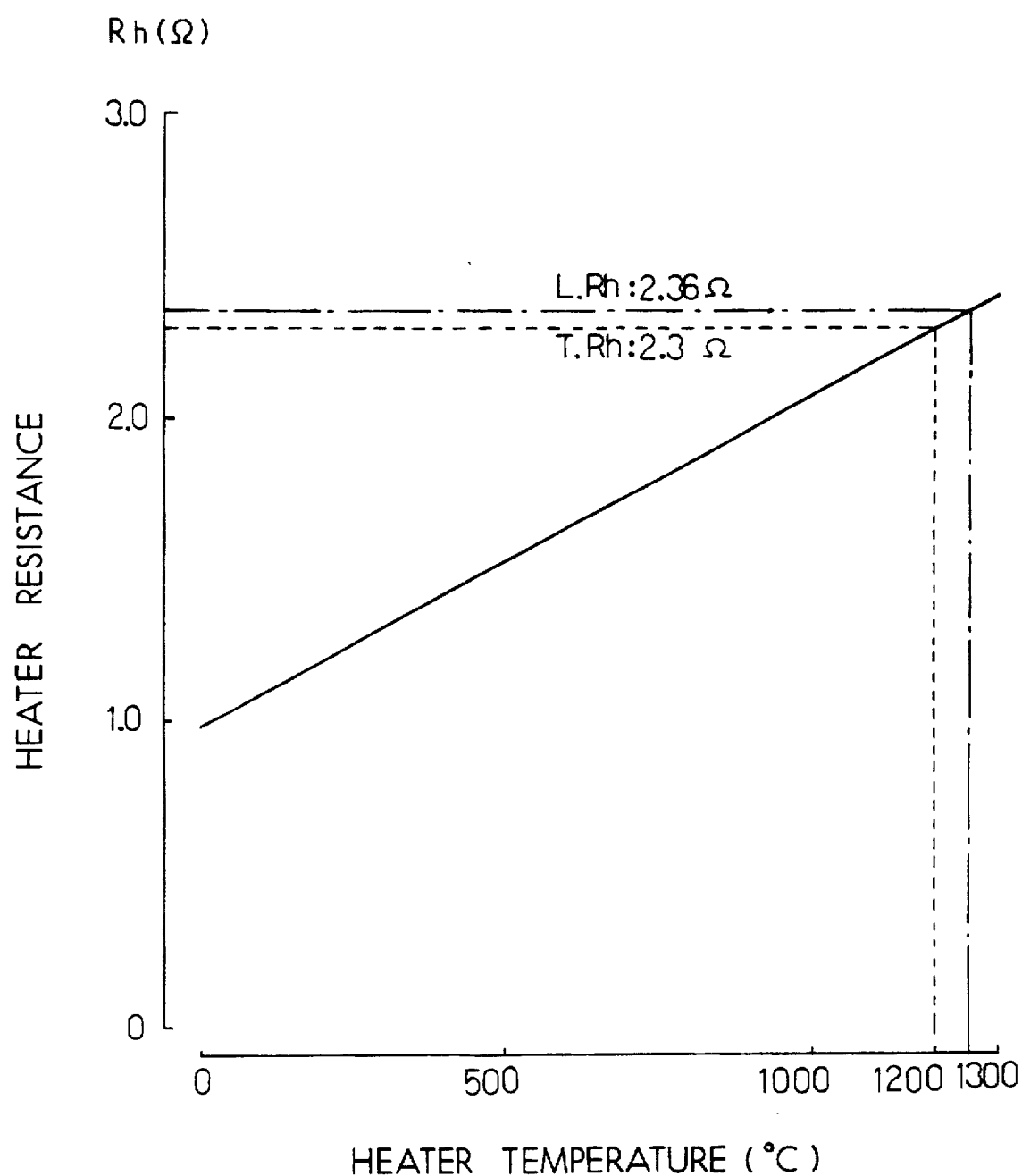
FIG. 7 is a characteristic diagram showing the relationship between heater temperature and heater resistance.

In step 107, whether the heater resistance Rh calculated in step 104 is larger than a target heater resistance T.Rh is determined. The relationship of the heater temperature and heater resistance Rh is shown in FIG. 7. Since the resistance/temperature characteristic shown here is determined by heater material shape etc., this one example is shown in the present embodiment, and this heater control is executable in any resistance/temperature characteristic. In the present embodiment, the limit heat resistance temperature of the heater 26 is 1250° C., therefore T.Rh is set at 2.3Ω equivalent to a somewhat lower heater temperature of 1200° C. than the limit heat resistance temperature. Also, this setting value depends on the user's intentions and there are no problems whatsoever in setting this at any value at all if it is within the heat resistance temperature range.

When Rh is less than T.Rh, YES is determined in step 107 and step 108 is proceeded to, wherein the duty ratio of the heater voltage is set to A(%). Here, A=100% full current supply (full power supply).

Also, where No is determined in step 107, step 110 is proceeded to and the duty ratio of the heater voltage is set to B(%). Here, B=0%. However, where there is a difference between the rise rate and fall rate of the heater temperature, it is possible to use a duty where B is in the order of 0 to 30%.

In the present embodiment, in steps 108 and 110, since duties of 100% and 0% are set as heater voltages, when heating the heater during heater full current supply control and heater temperature upper limit hold control, a voltage is supplied to the heater 26 at 100% duty by the heater control circuit 80, and 0% duty, i.e. not applying a voltage to the heater, is applied when cooling the heater during heater temperature upper limit hold control.

Also, where NO is determined in step 106, step 111 is proceeded to and duty operation of the heater voltage is executed for element temperature feedback control. The equation for duty in step 111 is expressed as follows.

$$Duty = Duty.1 + GP + GI$$
$$GP = KP \times (Zdc - T.Zdc) \quad \text{proportional item}$$
$$GI = GI + KI \times (Zdc - T.Zdc) \quad \text{integral item}$$

Here, Duty.I is an initial value for the duty and is 20%. Also, KP and KI are a proportional constant and an integral constant, and are respectively 4.2% and 0.2%. These values are experimentally obtained and are modified values according to the specifications of the heater 26. In the next step 112, the flag F2 is set at "1". When the flag F2 is set, it indicates element temperature feedback, and upon the flag F2 being set, the judgment in step 105 from the next process is NO and step 106 is not passed, and heater full current supply control and heater temperature upper limit hold control are not executed.

Also, in step 113, whether the difference between Zdc and T.Zdc calculated in step 104 is greater than 60Ω or not is determined. Where greater, this is a case where the element temperature is 100° C. or more lower than the target element temperature, step 114 is proceeded to and the flag F2 is cleared to "0". Thereby, in the next computation the determination of step 105 is YES and step 106 is proceeded to, and heater full current supply control or heater temperature upper limit hold control are again executed. However, in normal use, this does not occur if element temperature feedback control is executed once.

Also, in step 115 it is determined whether Zdc is greater than a limit element direct current impedance L.Zdc shown in FIG. 6 (set to a value smaller than the target element direct current impedance T.Zdc). Here, L.Zdc is set to 20Ω equivalent to the limit heat resistance temperature 750° C. of the element of the oxygen sensor S, and where Zdc is lower than L.Zdc, i.e. where the element temperature is higher than the limit heat resistance temperature, step 118 is proceeded to and application of voltage is immediately stopped. Also, when YES is determined in step 115, step 116 is proceeded to. In step 116, whether Rh is greater than a limit heater resistance L.Rh shown in FIG. 7 (set greater than the target heater resistance T.Rh) is determined. Here, L.Rh indicates the limit heat resistance temperature of the heater, and where Rh is greater than L.Rh, where the heater temperature is higher than the limit heat resistance temperature, step 118 is proceeded to and application of voltage is immediately stopped. Here, L.Rh is set to 2.36Ω equivalent to a heater temperature of 1250° C.

Steps 115 and 116 are for a fail safe, and when the element temperature and heater temperature are less than the heat resistance limit, step 117 is proceeded to. In step 117, the heater control circuit 80 is driven to apply a voltage to the heater 26 at the duty ratios set in steps 108, 110 and 111.

It is to be noted that in the present embodiment, the heater temperature upper limit hold control controls at 100% and 0%, i.e. executes restriction of ON and OFF, but there are no problems in controlling by operating the duty ratio as in the case of the element temperature feedback.

According to the first embodiment described above, by applying the voltage to the heater 26 at 100% duty at commencement of current supply to the heater 26, it becomes possible to activate the oxygen sensor S in a short time, and thereafter, upon reaching the target heater resistance T.Rh, by feedback-controlling the heater resistance Rh to the target heater resistance T.Rh (heater upper limit temperature hold control), electrical wire breakage in the heater 26 can be prevented, and thereafter, upon reaching the target element temperature, since the element temperature of the oxygen sensor S is normally continuously controlled to a target element temperature, there are the excellent advantages of not receiving the effects of exhaust temperature etc., being able to maintain the oxygen sensor S in an activated state, and damage to the oxygen sensor S being preventable.

[Second Embodiment]

The overall structure of the second embodiment is similar to the first embodiment of FIG. 2, and heater control of the oxygen sensor S which is repeatedly executed in predetermined cycles by the microcomputer 70 will be explained according to the flow chart of FIG. 8.

The heater control shown in this flow chart indicates a control process from when heater current supply is commenced till the element is activated. Explanation will be given regarding heater control after activation during element temperature feedback. The ignition switch (IG) signal, which is the current supply condition to the heater 26, is determined in step 201. Where IG is not ON processing is stopped, and when IG is ON step 203 is proceeded to.

In step 203, element direct current impedance Zdc of the oxygen sensor S is computed. As the computation method for this direct current impedance Zdc, $$\frac{\text{Direct current}}{\text{impedance } Zdc(\Omega)} = \text{applied voltage } Vneg(V) + \text{detected current } Ineg(A)$$

is computed with the addition of a negative voltage Vneg to the element and determining the current value Ineg at that time. Generally, the relationship between element temperature and element direct current impedance is as in FIG. 6 described previously, and the element temperature can be found by detecting the element direct current impedance Zdc.

Next, in step 202, whether the flag F1 is "1" or not is determined.

The flag F1 is the activation flag for the oxygen sensor S, and indicates whether or not the heater temperature after heater current supply is 700° C. or more (30Ω at the element direct current impedance). Where the flag F1 is "1", it is determined that the element is already activated and step 211 is proceeded to, wherein a heater control routine for element activation is executed and element temperature feedback control for maintaining an active state of the element temperature is performed. The control content is described below.

Also, where the flag F1 is "0" in step 202, it is determined to be an element inactive state and step 204 is proceeded to. In step 204, it is determined whether the element direct current impedance Zdc detected in step 203 is greater than 30Ω or not. In other words, whether the element temperature is greater than 700° C. or not is determined. Where NO is determined in step 204, a state where the element temperature is 700° C. or more is indicated and it is determined that the element is activated. In this case, step 210 is proceeded to and the oxygen sensor S activation flag F1 is set to "1" and heater control for feedback controlling the element temperature is proceeded to.

Figure 9:
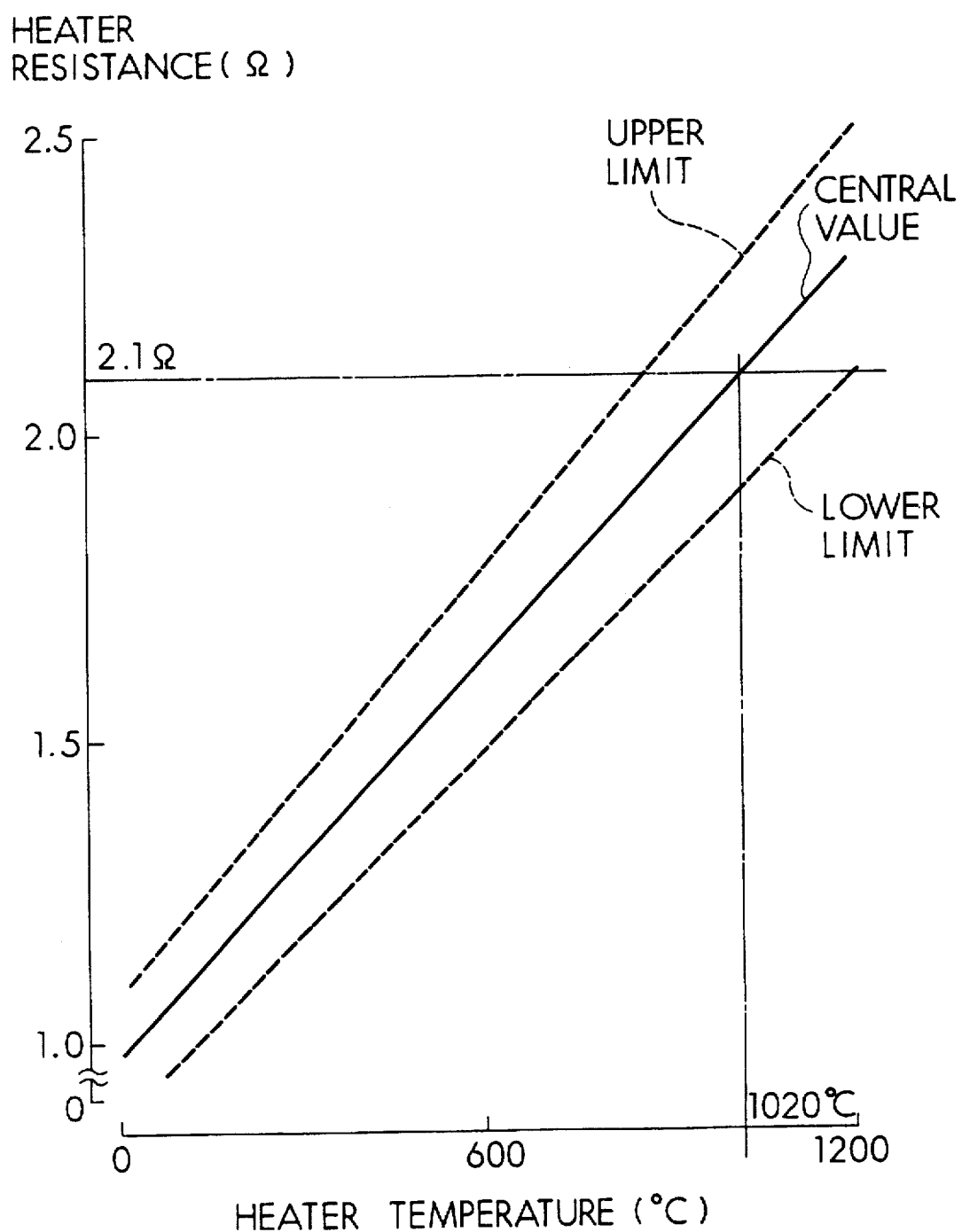
FIG. 9 is a characteristic diagram showing the relationship between heater temperature and heater resistance.

Also, where YES is determined in step 204, the element temperature is lower than 700° C., this is taken as an inactive state and heater control for activating the element is performed. Firstly, in step 205, the applied voltage Vn and current In to the heater 26 are detected. Next, in step 206, the heater resistance Rh is computed as Rh=Vn/In from the voltage Vn and current In detected in step 205. The relationship between heater temperature and heater resistance is shown in FIG. 9. The heater temperature can be known by detecting the heater resistance Rh.

Next, in step 207, whether the resistance value detected in step 206 is 2.1Ω or less is determined. Although the heater resistance Rh of 2.1Ω is equivalent to a heater temperature of 1020° C., considering inconsistencies in the heater resistance Rh as shown in FIG. 9, the heater temperature varies within the range of 870° to 1200° C. Here, the reason for setting the criterion of 2.1Ω is because even where using a heater with any type of heater resistance temperature characteristic, the heater resistance limit of the heater 26 does not exceed 1200° C. It is possible to set this setting value on the safe side.

Also, where YES is determined in step 207, since the heater 26 is still in a state where it can heat, the duty is taken as 100% in step 208 and a voltage of 100% duty is applied to the heater by the heater control circuit 80 in step 209. Although the duty cycle here is 10 Hz, this may be an arbitrary value.

In addition, where NO is determined in step 207, this state indicates that lower limit products of the heater resistance temperature characteristic in the heater 26 have approached 1200° C., and indicates timing proceeding from the voltage control up till this time to power control. Firstly, in step 212, whether the heater power control flag F2 is "1" or not is determined. This flag F2 indicates whether heater power control has already been performed.

Where NO is determined in step 212, this is state where heater power control has not yet been performed, and step 219 is proceeded to. In step 219, the initial duty of the heater power control is set and although a value according to the heater capacity is input, in the present embodiment it is experimentally set to 20%. This value is a suitable value for restricting sudden heater temperature changes when proceeding from heater voltage control to full power control.

Also, since there is a surplus increase in heater temperature also immediately after a heater power shift in a case where the criterion of the heater resistance Rh in step 207 is set 2.0Ω on the safe side, it is possible to set the initial duty in step 219 to a value greater than 20%.

Next, in step 220, the heater power control flag F2 is set to "1". In other words, indicating heater power control execution. Next, step 209 is proceeded to and a voltage is applied to the heater 26 by the heater control circuit 80 based on the initial duty set in step 219.

Also, a case where YES is determined in step 212 is taken as being during heater power control execution and step 222 is proceeded to. In step 222, it is determined whether the heater resistance value Rh computed in step 206 is greater than 2.5Ω. This step 222 is a heater protection function with respect to cases such as where the heater temperature is abnormally heated by a rise in exhaust temperature accompanying rapid changes in the operating conditions of the engine, or some kind of damage etc., and where the heater resistance Rh is 2.5Ω or more, YES is determined in step 222 and step 223 is proceeded to. In step 223 a value which rapidly decreases 10% duty from the previously set duty is taken as the present duty. Here, where the duty is 0% or less, all duties equal 0%. Also, the next step 209 is proceeded to and a voltage is applied to the heater 26 by the heater control circuit 80 based on the duties set in step 223 and the heater temperature is reduced.

Figure 10:
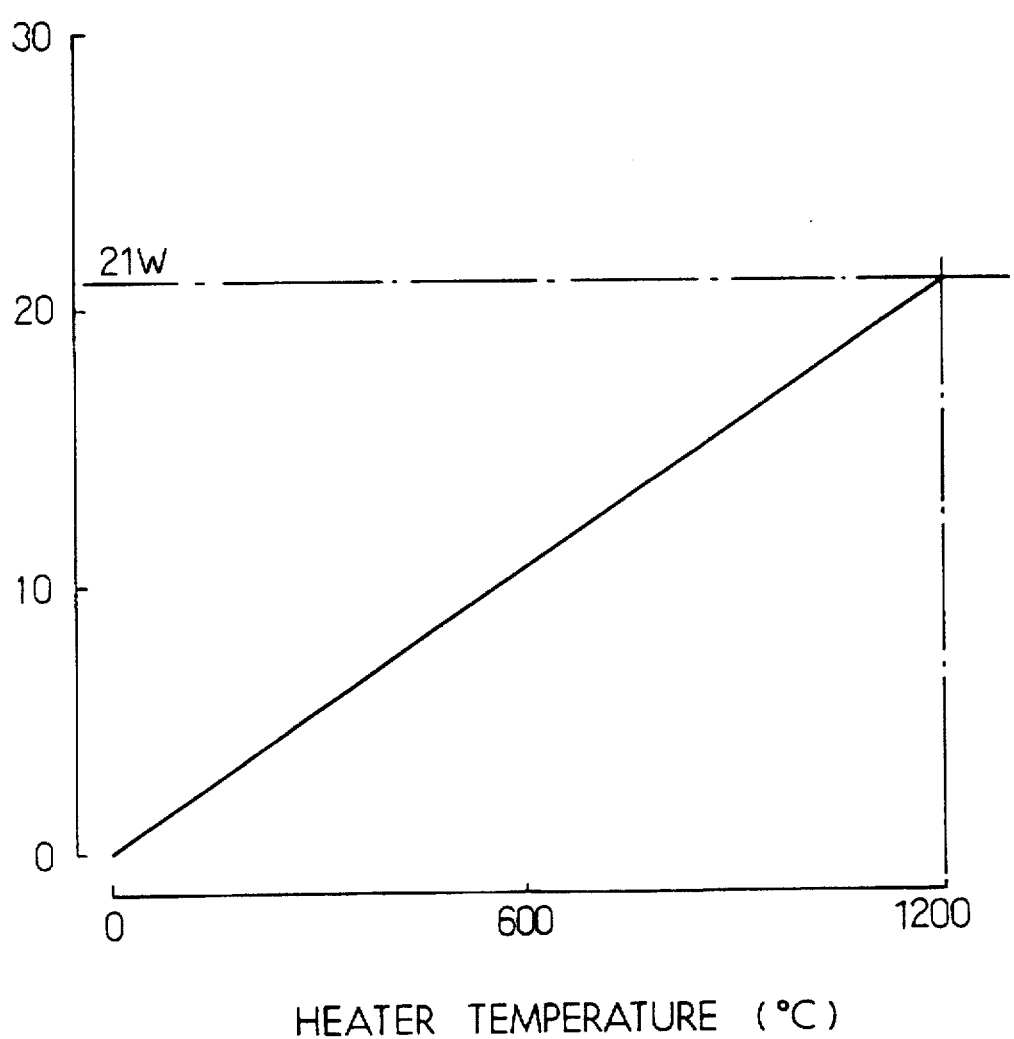
FIG. 10 is a characteristic graph showing the relationship between heater temperature and power supply.

Also, where NO is determined in step 222, step 213 is proceeded to, based on the present duty % determined by steps 219, 223 or 215, 217 and the heater voltage Vn and current In detected in step 205, the heater power Wn is computed by Wn=Vn×In×Duty/100. In the next step 214 it is determined whether the power Wn computed in step 213 is 21 (W) or less. Here, the relationship between heater temperature and heater supply power is shown in FIG. 10. This relationship indicates a constant proportional relationship not affected by inconsistencies in the heater resistance temperature characteristic described above. Thereby, if it is a capacity (heater exothermic effectiveness) equivalent to supplying 21 (W) in the heater used in the present embodiment, all heater temperatures are saturated at 1200° C. regardless of inconsistencies in the resistance characteristic. Thereby, it does not exceed the heat resistance temperature and extend to damage and wire breakage.

Also, where YES is determined in step 214, it is taken that the power supply to the heater 26 is lower than the target power and step 215 is proceeded to. In step 215, 3% is added to the previous duty rate. This value is a value determined by heater capacity. Next, step 209 is proceeded to and a voltage is applied to the heater 26 by the heater control circuit 80 based on the duty ratio set in step 215, and the power supply to the heater 26 is increased.

Also, where NO is determined in step 214, the power supply to the heater 36 is taken as being higher than the target power and the duty ratio is deceased by 3% in step 217. Next, step 209 is proceeded to and a voltage is applied to the heater 26 by the ratio control circuit 80 at a duty set at step 217, and the power supply to the heater 26 is decreased. The supply capacity to the heater 26 may be controlled with the target power at 21 W in the processes of steps 213 to 217.

Here, the computing process detects whether the actual power supply Wn to the heater 26 is higher or lower than the target power of 21 W, and although this is an addition/subtraction operation of a predetermined value, but there are also methods for duty operation by proportional and integral control. For example, duty can be computed by a method of $Duty = GP + GI + C$
$GP = a(Wn - 21)$ Proportional item
$GI = GI + b(Wn - 21)$ Integral item where a, b and c equal constants, and it is possible to control the heater power at a target power.

Next, the method of element temperature feedback in step 211 will be explained. Based on the element direct current impedance Zdc detected in step 203, the duty ratio of the voltage applied to the heater 26 such that the element direct current impedance Zdc is 30Ω (corresponding to element temperature 700° C.) is computed. Duty computation is expressed by the following equation.

$Duty = GP + GI + C$
$GP = a(Zdc - 30)$ Proportional item
$GI = GI + b(Zdc - 30)$ Integral item
$(a = 4.2, b = 0.2, c = 20)$ a, b and c are constants, in agreement with the present embodiment as described above.

By controlling the heater based on the duty ratio computed as above, continuously controlling the element direct current impedance Zdc in the vicinity of 30Ω is possible, and it can be continuously maintained in a favorable active state, and element damage by abnormal heating of the element temperature can be further prevented.

FIGS. 11A through 11D show timing charts after heater current supply in the second embodiment till the oxygen sensor S becomes fully active, and immediately after power is input to the heater 26, the heater control circuit 80 controls it at 100% duty and the heater 26 is rapidly heated by constant voltage controlling (heater full conduction control) the power supply to the heater 26. Thereafter, upon the heater resistance Rh reaching the target value (2.1Ω), the duty ratio of the heater control circuit 80 is controlled such that the power supply Wn to the heater 26 is kept at the target power of 21 W (such that the temperature of the heater 26 is 1200° C.) and the power supply to the heater 26 is constant power controlled. Thereafter, upon the internal resistance Zdc of the oxygen sensor S reaching a target value of 30Ω, the duty ratio is controlled by the heater control circuit 80 and the power supply to the heater 26 is element temperature feedback controlled such that the internal resistance Zdc of the oxygen sensor S is kept around the target value of 30Ω (element temperature is 700° C.).

According to the second embodiment above, since it can be effectively used from during activation of the heater 26 by an applied voltage till the heat resistance temperature region of the heater 26 by switching from constant voltage control to constant power control, the oxygen sensor S can be activated in a faster time. Also, wire breakage in the heater 26 can be prevented by constant power control and element temperature can be simultaneously detected, therefore there is the excellent advantage that damage to the element can be prevented.

[Third Embodiment]

In the third embodiment shown in FIG. 12, differences from the second embodiment will be explained. Although shift timing from the heater constant voltage control to constant power control was performed in accordance with the heater resistance value Rh in the second embodiment, the third embodiment switches in accordance with the time lapse after commencement of heater current supply. The flow chart of FIG. 12 determines whether the time lapse after commencement of operation is the predetermined value, 12 seconds, in step 307 when YES is determined in step 204. Where YES is determined in step 307, since it is determined that the heater 26 is not yet sufficiently heated, step 208 is proceeded to and a voltage is applied to the heater 26 at a duty of 100%.

Also, where NO is determined in step 307, it is taken that the heater 26 is in a sufficiently heated state and heater power control of steps 205, 206 and thereafter is proceeded to. Here, setting of the time lapse is determined by heater capacity. Although in the present embodiment it has been set at a value of 12 seconds, it is preferable to set the time lapse such that the time is short where the engine coolant temperature is high.

Note that also in cases where recommencing operation in a state where the heater temperature has not sufficiently cooled, since the element direct current impedance Zdc is compared with a predetermined value in step 204, it is possible to avoid abnormal heating of the heater 26 and the oxygen sensor S. Also, in cases where the heater resistance temperature characteristic changes over time, the shift to power control under the same conditions is possible and this is useful for protecting the heater 26.

[Fourth Embodiment]

Two methods of shifting from full conduction control at commencement of heater current supply to upper limit hold control for holding the heater temperature in the vicinity of a heat resistance limit, and shifting to the constant power control for supplying a constant power have been presented in the first to third embodiments as heater controls for rapid activation of the oxygen sensor S. However, there is no means for converting from heat resistance without having a means for direct detection of the heater temperature of the oxygen sensor S. However, there are inconsistencies as shown in FIG. 9 in the heater temperature resistance characteristic of the oxygen sensor S, and there is the problem that temperatures differ greatly due to the oxygen sensor S (heater 26) while there is the same resistance.

Here, upper limit hold control performs control such that the resistance becomes a target resistance value and shift timing to constant power control is determined by the heater resistance value, thus while ensuring the reliability of the heater 26 it is difficult to raise the heating performance.

Here, according to the fourth embodiment, the heater temperature is estimated from engine revolutions, air intake pressure, power supply, etc., it is possible to update the target heater resistance by detecting heater resistance at that time (upper limit hold control and shift timing) and compatibility between reliability and heating performance is possible.

An outline of the heater temperature estimation method will be explained.

Heater temperature is determined by the ratio of supplied heat amount and heat radiation amount from the heater 26. Considering the constant thermal state, the supplied heat amount to the heater 26 is determined by the amount of power supplied to the heater 26, and the amount of radiated heat from the heater 26 is substantially determined by the temperature and flow speed of exhaust gases of the internal combustion engine which constitute the surrounding environment of the oxygen sensor S. The amount of radiated heat from the heater 26 varies in atmospheric temperature and exhaust manifold temperature in a sensor attachment position etc., but comparing these with heat radiation to the exhaust, the effect thereof is small.

Also, where the temperature and flow speed of exhaust gas restrict combustion, air-fuel ratio, ignition timing, etc., these are substantially readily determined by engine revolutions NE and air intake pressure PM or air intake amount QA. Thereby, where the power supply is fixed, heater temperature can be determined from engine revolutions NE and air intake pressure PM.

Next, explanation will be given of a transition state. Where outside air temperature, air-fuel ratio (A/F), ignition timing, etc. do not change, the heater temperature changes due to engine revolutions, air intake pressure and heater power supply. Regarding changes in heater temperature with respect to changes in these parameters, it is understood that an approximation can be made by a first order lag from the standpoint of heat transfer dynamics.

Also, time constants between heater temperature changes accompanying changes in the surrounding environment (engine revolutions NE and air intake pressure PM) and heater temperature changes accompanying power supply changes each differ greatly. In other words, regarding changes in the surrounding environment reaching to heater temperature changes after temperature distribution changes in element portions, these are due to power changes being distributed by heat conduction rate determined by the quality of the heater 26, and time constants accompanying power changes are smaller than time constants accompanying changes in changes in the surrounding environment. Further, it is understood that these two time constants are each readily determined by experimental exhaust gas flow amounts (can be substantially approximated by the type of engine revolutions NE and air intake pressure PM).

Thereby, it is possible to estimate heater temperature by calculating (1) heater temperature in a constant state with respect to NE and PM at a time of constant power and (2) a first-order lag or delay relative to changes in NE, PM or power supply.

Figure 13:
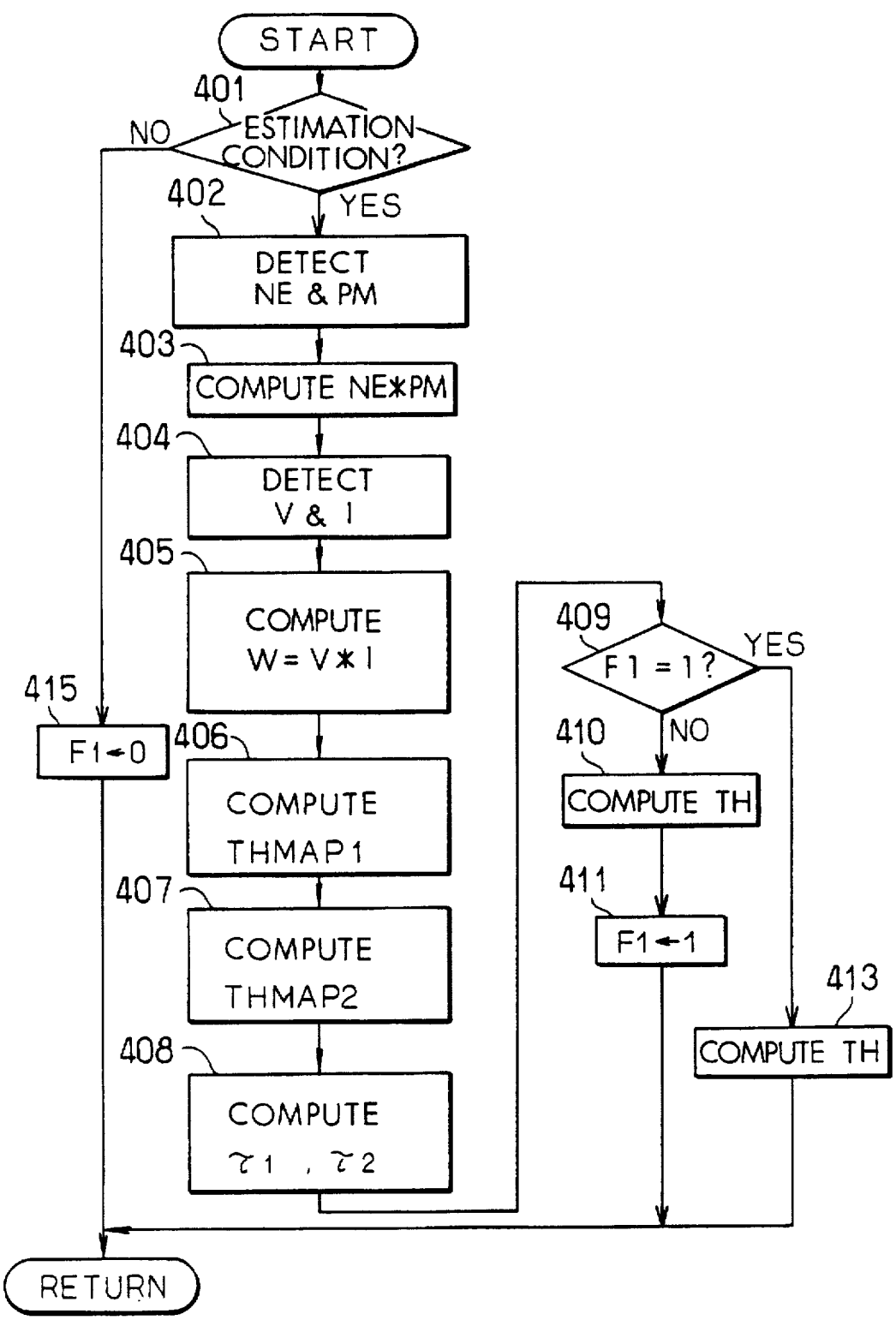
FIG. 13 is a flow chart showing an operation of a microcomputer in a fourth embodiment of the present invention.

Next, a detailed explanation according to the flow chart of FIG. 13 executed every 100 ms by the microcomputer 70 will be made. Step 401 determines whether or not heater temperature estimation is possible. This is for ensuring the precision of the heater temperature estimation, and conditions are restricted for attempting to increase estimation precision. Causes of errors are thought to be (1) NE, PM and power→constant heater temperature and (2) NE*PM→time constant computation. The execution conditions of the present embodiment are:

1000≦NE≦3000 rpm;

200≦PM≦600 mmHg;

20≦outside air temperature≦30° C.;

80° C.≦water temperature; and during air-fuel ratio feedback control.

When these conditions are met, step 402 is proceeded to. Also, ignition timing and vehicle speed etc. may be considered as estimation execution conditions at this time.

Where NO is determined in step 401, step 415 is proceeded to and the process of clearing the flag F1 is made. In step 402, engine revolutions NE and air intake pressure PM are detected. In step 403 NE*PM (multiplication of NE and PM) is computed based on the detected values of step 402. In step 404 the heater voltage V and heater current I applied to the oxygen sensor S are detected. In step 405 power supply W=V*I is computed based on the detected values of step 404.

In steps 406 and 407, heater temperature in a constant state is computed. In the present embodiment, heater temperature is computed by the sum of a reference heater temperature THMAP1 with respect to NE and PM under a given reference power supply and a corrected heater temperature THMAP2 which corrects THMAP1 according to a difference in power supply W computed in step 405 with respect to the reference power. In other words, this is expressed in the form of heater temperature=THMAP1+THMAP2. For this reason, in step 406 THMAP1 is computed according to NE and PM detected in step 402. In the present embodiment, the constant heater temperature map of step 406 is set as shown in FIG. 14.

Also, the reference power at this time is 10 W for example, this value being based on where the frequency of the power being applied to the heater 26 is large in order to maintain an active state of the element. Thereby, since the amount of power changes due to each engine and the attachment of the oxygen sensor S, it is also necessary to change this reference power.

In the next step 407, THMAP2 is computed from the power supply W computed in step 405 and NE and PM detected in step 402. The power correction heater temperature map THMAP2 of step 407 is shown in FIGS. 15A through 15C. In the present embodiment, although three maps are set as THMAP2 and the power supply W of each is taken as 5 W, 15 W and 25 W, these values substantially include the amount of power W supplied to the heater 26 and can be arbitrarily set. Also, NE, PM and power supply W may be each linearly interpolated.

Here, since the constant heater temperature map of step 406 for example takes 10 W as a standard, when the detected power of step 405 is 10 W the power correction heater temperature THMAP2 of step 407 is 0° C. and the constant heater temperature map value THMAP1 of step 406 is the heater temperature as is.

The heater temperature is computed by these two maps THMAP1 and THMAP2 where operating conditions and power supply are restricted.

Where considering a transition state, a first-order lag time constant of the heater temperature differs when only NE and PM change as described above and only the power supply W changes. Here, first-order lag computation when only NE and PM change is performed based on THMAP1 from the constant heater temperature map, and where only the power changes is computed based on THMAP2 from the power correction heater temperature where only the power supply W changes. In actuality, since all of NE, PM and power supply W change, the first-order lag computations of THMAP1 and THMAP2 are simultaneously executed. The time constants used in each of the first-order lag computations are shown in FIG. 16. The time constant $\tau 1$ relates to changes in NE and PM, while the time constant $\tau 2$ relates to changes in the power supply W. Also, each of these time constants is substantially readily determined by NE*PM. It is to be noted that since the time constants are effected by NE and PM, NE and PM can also be stored by a two-dimensional map.

Next, in step 408, time constants $\tau 1$ and $\tau 2$ are computed by NE*PM computed in step 403. In the next step 409 whether the flag F1 is set or not is determined. The flag F1 determines whether the heater temperature computation has been previously executed or not, and where it is determined as NO, in other words where the heater temperature computation is executed for the first time, steps 410 and 411 are proceeded to and where otherwise step 413 is proceeded to.

The heater temperature computation in steps 410 and 413 is executed by the following equation.

Step 413 is expressed as follows.
[Equation 1]

Heater temperature $TH(i+1)=TH1(i+1)+TH2(i+1)$ $TH1(i+1)=e^{-\Delta T/\tau 1} \cdot TH1(i)+(1-e^{-\Delta T/\tau 1}) \cdot THMAP1(i)$ $TH2(i+1)=e^{-\Delta T/\tau 2} \cdot TH2(i)+(1-e^{-\Delta T/\tau 2}) \cdot THMAP2(i)$ Step 410 is expressed as follows.
[Equation 2]

$TH(1)=THMAP1(1)+THMAP2(1)$

Here $\Delta T$ indicates an operation period, and in the present embodiment is set as $\Delta T=0.1$ (sec). In step 411, the flag F1 is set and YES is determined in step 409 in the next operation, and after proceeding to step 413, the process is finished. Consequently, without departing from the conditions of step 401, the heater temperature is computed in step 413 for each operation cycle of 100 ms.

Although air intake pressure PM is used in the present embodiment, similar heater temperature estimation can be executed by air intake amount QA per engine revolution.

The map values used in the present embodiment may vary depending on the characteristics of each engine.

Also the execution conditions of step 401 can be selectively used depending on required accuracy of heater temperature estimation and computation.

Figure 8:
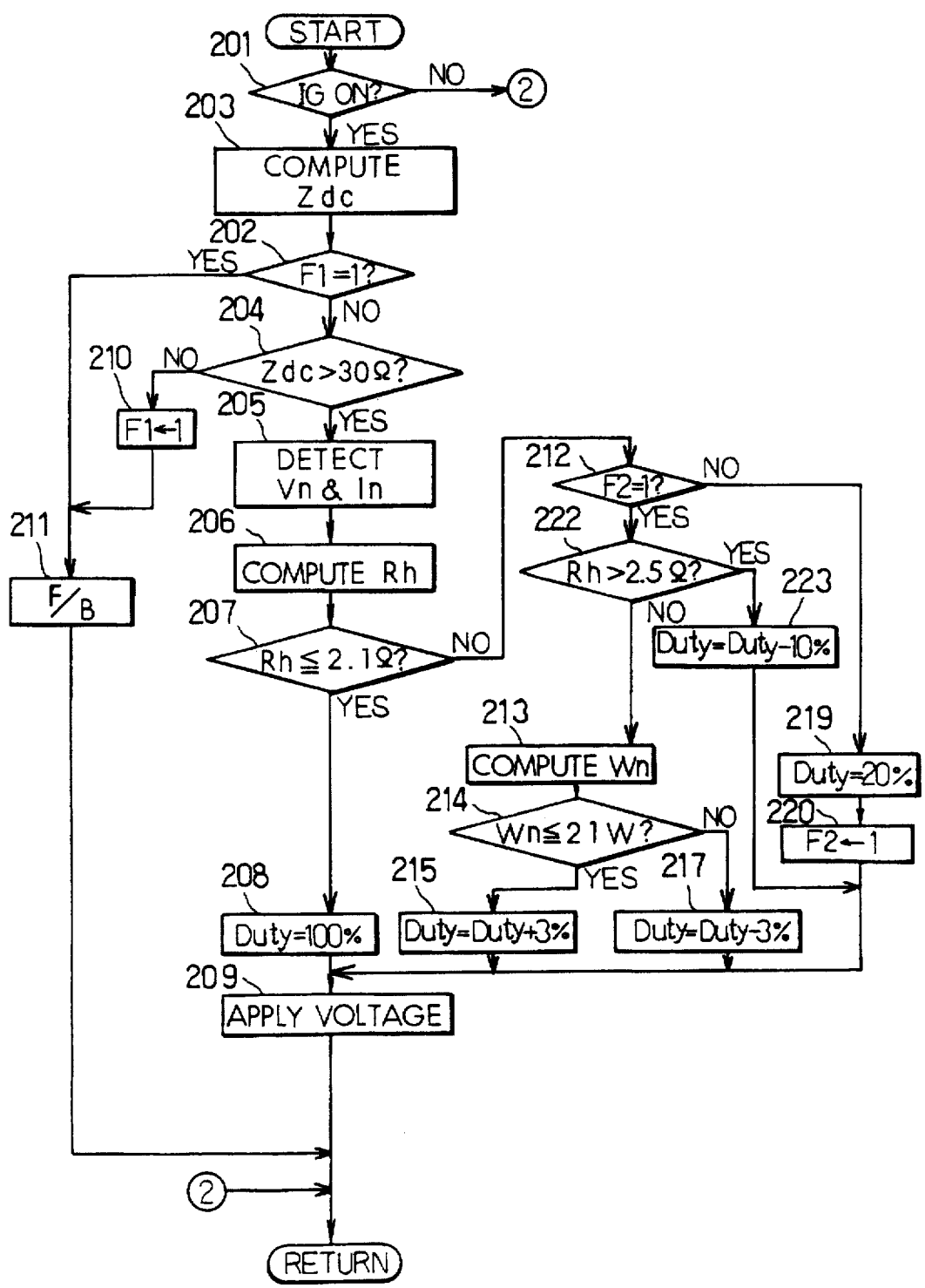
FIG. 8 is a flow chart showing an operation of the microcomputer in a second embodiment of the present invention.
Figure 12:
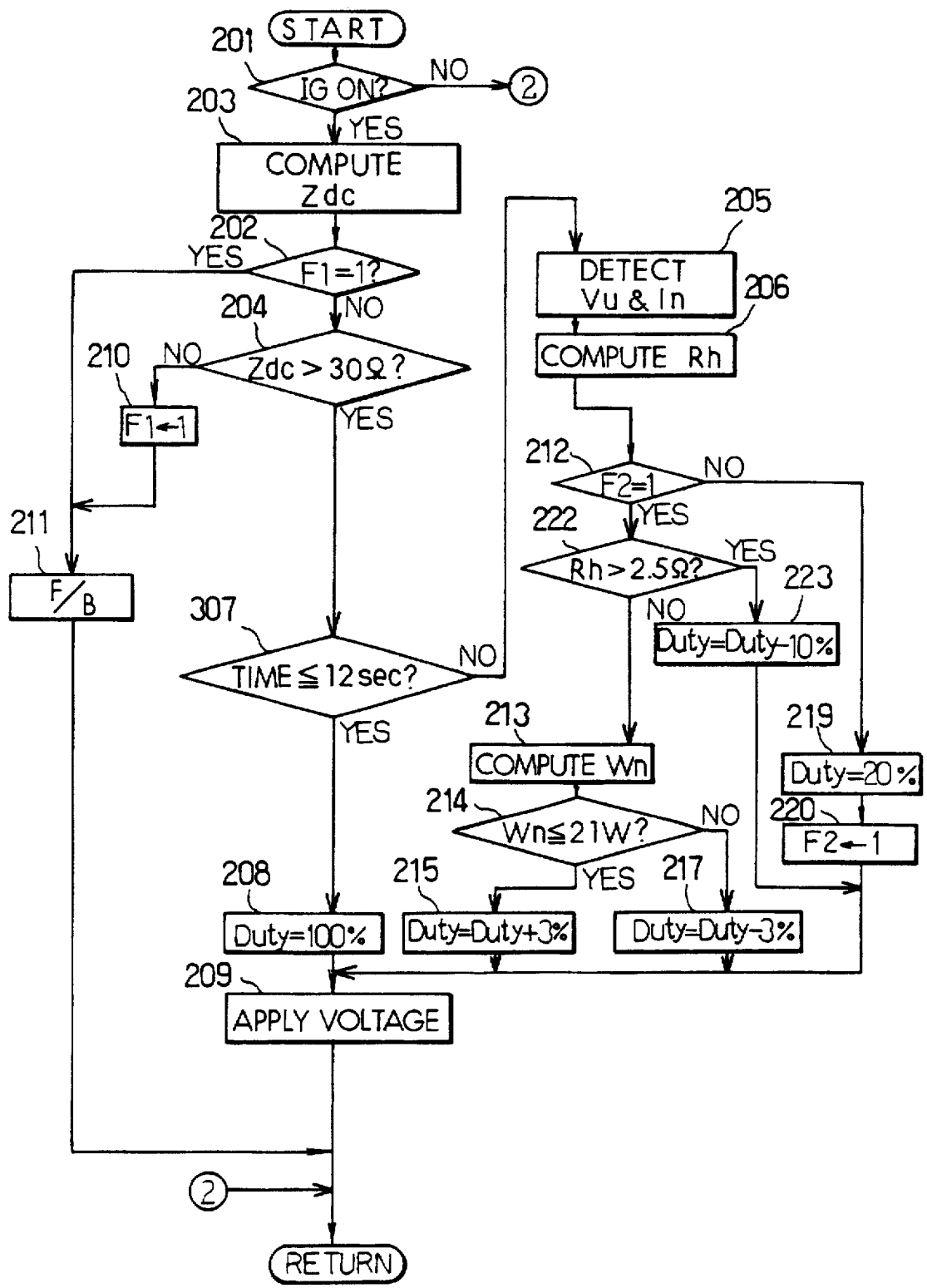
FIG. 12 is a flow chart showing an operation of a microcomputer in a third embodiment of the present invention.
Figure 17A:
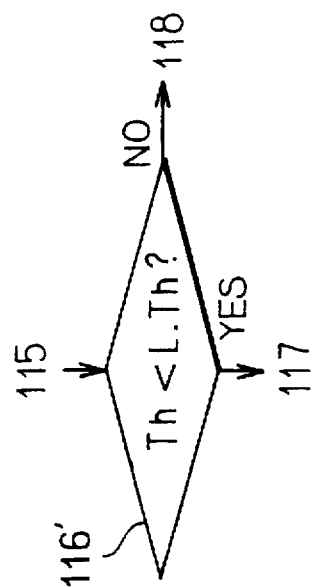
FIGS. 17A and 17B are flow charts showing differing portions of FIG. 5 in the case of where it is applied to the above fourth embodiment.
Figure 17B:
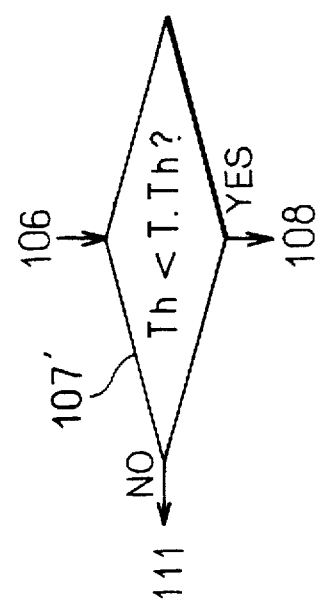

By using the heater temperature Th estimated in this way in place of heater resistance Rh in the flow charts of FIG. 5, FIG. 8 and FIG. 12, it is possible to apply it to power supply control with respect to the heater 26. In this case, in FIG. 5, as shown in step 107' of FIG. 17A in place of step 107, as well as determining whether or not the heater temperature Th is greater than the target heater temperature T.Th (e.g. 1200° C.), as shown in step 116' of FIG. 17B in place of step 116, it is determined whether or not the heater temperature Th is greater than the limit heater temperature L.Th (e.g. 1250° C.).

Figure 17C:
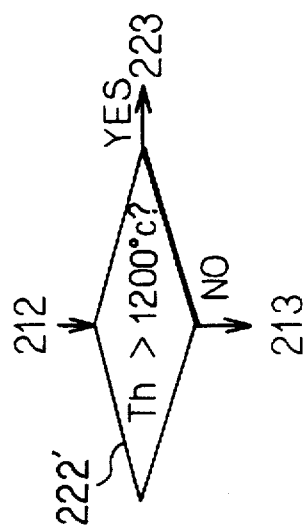
FIGS. 17C and 17D are flow charts showing differing portions of FIG. 12 in the case of where it is applied to the above fourth embodiment.
Figure 17D:
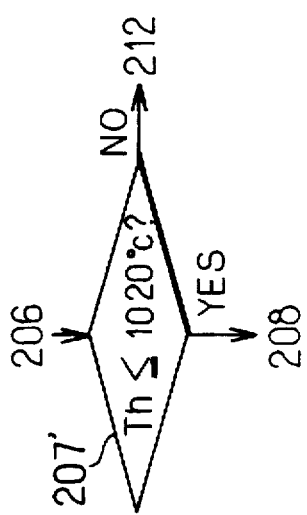

Also, in FIG. 8, as shown by step 207' of FIG. 17C in place of step 207, whether or not the heater temperature Th is 1020° C. or more is determined, and in step 222' of FIG. 17D in place of step 222, whether or not the heater temperature is greater than 1200° C. is determined.

Also in FIG. 12, step 222' of FIG. 17D may be executed in place of step 222.

[Fifth Embodiment]

Next, explanation will be given of the setting method for the target resistance value in heater control based on the heater temperature estimated in the fourth embodiment. This target resistance value is used for determining the shift timing from full conduction control to heater upper limit hold control or constant power control in the first to third embodiments described above. Also, it can be used in setting the limit heater resistance.

Figure 18:
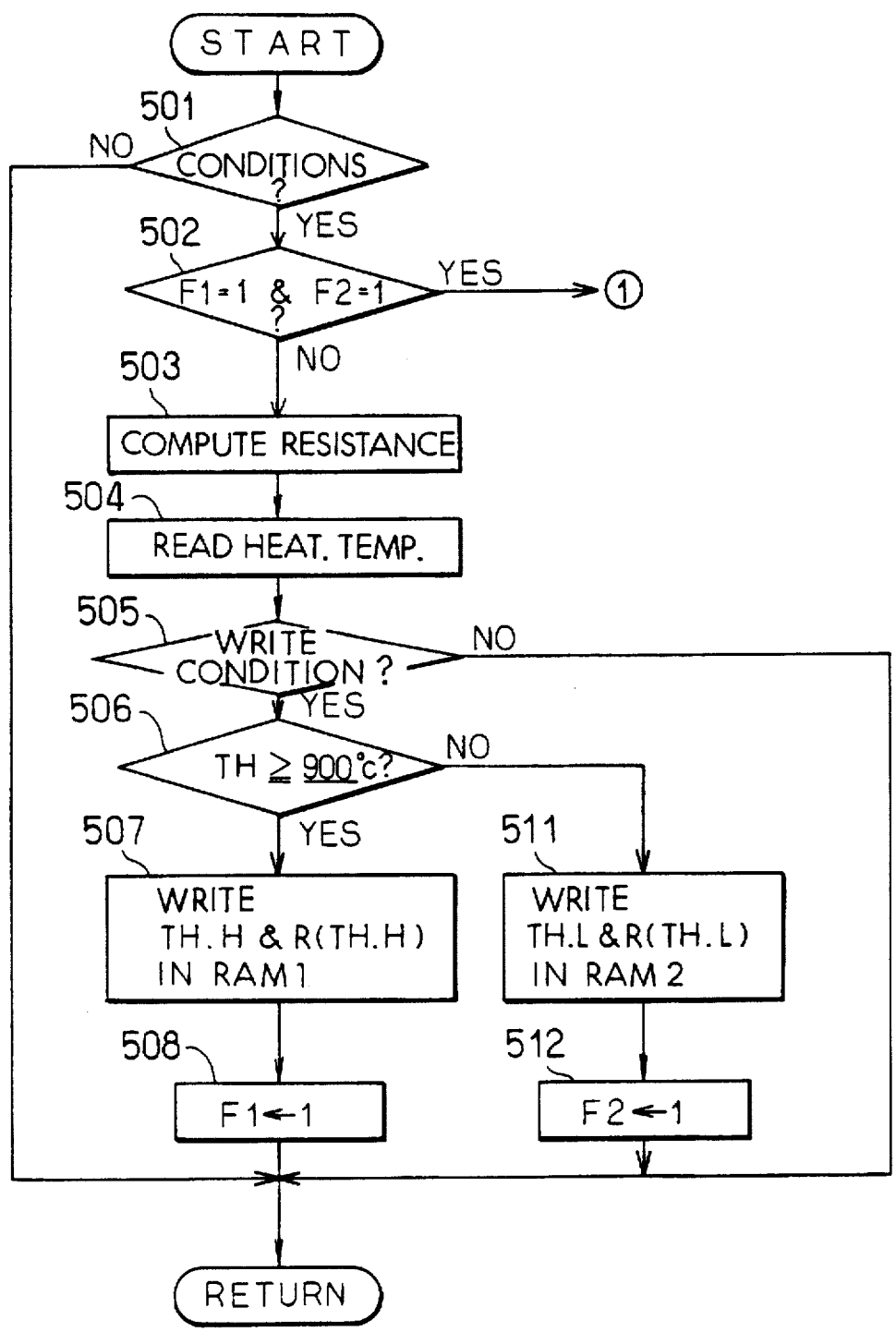
FIG. 18 is a flow chart showing an operation of a microcomputer in a fifth embodiment of the present invention.

In the flow chart of FIG. 18 executed every 100 ms by the microcomputer 70, step 501 determines whether or not the execution conditions for target resistance value update control are set or not, and when determined as YES, step 502 is proceeded to and when determined as NO, the operation is completed as is. The execution conditions of step 501 are for example:

during execution of heater temperature estimation control; NE change rate$\leq$500 rpm and continuation interval$\geq$20 sec; and PM change rate$\leq$300 mmHg and continuation interval$\geq$20 sec. These conditions are to ensure the precision of heater temperature estimation and may be used with other signals.

Figure 19:
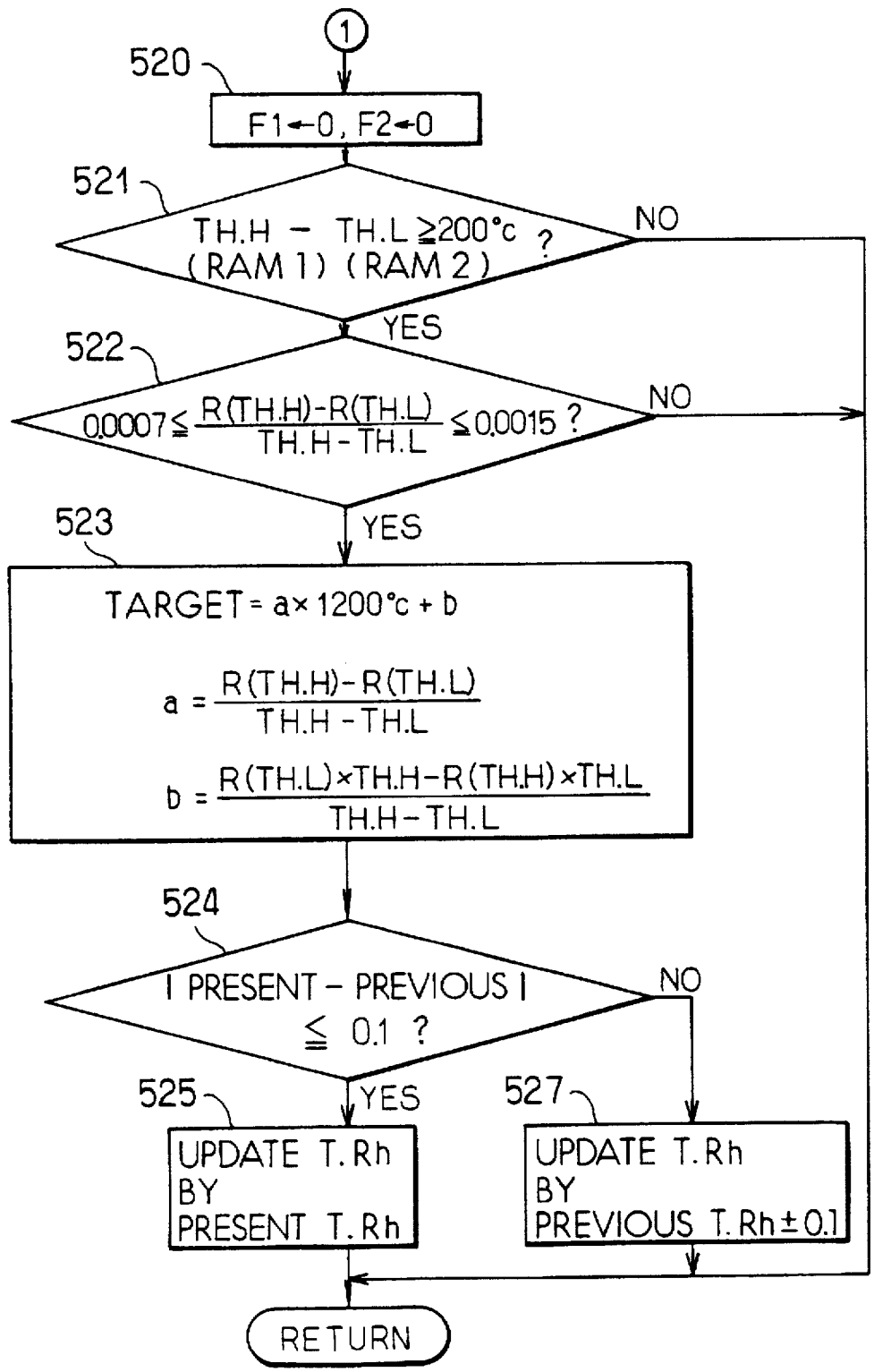
FIG. 19 is a flow chart showing an operation of the microcomputer in the fifth embodiment of the present invention.

In step 502 it is determined whether either one of flags F1 and F2 are set. Where YES is determined, step 520 of FIG. 19 is proceeded to and the target resistance value is set. With NO in step 502 on the contrary, the heater resistance value is computed in step 503 based on the detected heater voltage and heater current. In step 504 the heater temperature estimated in the heater temperature estimation control in FIG. 13 described above is read.

In the next step 505 it is determined whether the relationship of heater temperature to heater resistance read in step 504 is appropriate or not. In other words, inconsistencies in the heater resistance-temperature characteristic used in the present embodiment within the range of:

(characteristic upper limit)

heater resistance=0.0013×heater temperature+1.0671; and (characteristic lower limit)

heater resistance=0.0009×heater temperature+0.8776, as shown in FIG. 9, can be understood. Thereby, in step 505 whether the heater temperature-heater resistance determined in steps 504 and 505 is within the above inconsistency range is determined.

Where NO is determined in step 505 the process is finished and where YES is determined step 506 is proceeded to. In step 506 it is determined whether the heater temperature in step 504 is 900° C. or more. Where YES is determined in step 506, step 507 is proceeded to and the heater temperature and heater resistance at that time are written into a RAM1 as TH.H and R(TH.H), and when NO is determined step 511 is proceeded to and the heater temperature and heater resistance at that time are written into a RAM2 as TH.L and R(TH.L). Here, RAMs 1 and 2 use a back-up RAM and this information is also stored when the key switch is off and the engine is stopped. Upon completion of the writing in of heater temperatures TH.H and TH.L and heater resistances R(TH.H) and R(TH.L) in steps 507 and 511, each process proceeds to steps 508 and 512 and the process of setting the flags F1 and F2 is completed.

Next, an explanation of FIG. 19 will be given. Where YES is determined in step 502 of FIG. 18, this is a case where the heater temperatures TH.H and TH.L and the heater resistances R(TH.H) and R(TH.L) corresponding thereto are stored in RAM1 and RAM2, and a target heater resistance value with respect to the target heater temperature is computed using these two points.

Step 520 of FIG. 19 clears each of the flags F1 and F2. Thereby, the next target resistance value update is not executed only if no new information is entered into RAM1 and RAM2. In the next step 521 whether the difference between the heater temperatures TH.H and TH.L stored in RAM1 and RAM2 is 200° C. or more is determined. Here, the 200° C. which is set is used where the heater temperature during element temperature feedback is in the vicinity of 800° to 1100° C., and is for ensuring accuracy when calculating heater resistance at 1200° C. from these two points. Thereby, by balancing precision and detection opportunity, arbitrarily setting this temperature is possible.

Where NO is determined in step 521 the process is finished and where YES is determined step 522 is proceeded to. Step 522 determines whether the heater temperature-heater resistance relationship stored in RAM1 and RAM2 is suitable. Difference can be understood in the range where the resistance change is from 0.0007 (Ω/°C.) to 0.0015 (Ω/°C.) with respect to temperature changes in the heater used in the present embodiment. Consequently, where the bias obtained in the form of
[Equation 3]

$$\{R(TH.H)-R(TH.L)\} \div \{TH.H-TH.L\}$$

from RAM1 and RAM2 is not within this range, the process is finished, and where within this range it is determined that the relationship of these two points is suitable and step 523 is proceeded to.

In step 523 heater resistance when the heater temperature is 1200° C. is computed from the heater temperatures and heater resistances of RAM1 and RAM2. This resistance value is the target heater resistance T.Rh and 1200° C. is the upper limit temperature of the heater used in the present embodiment. Thereby, this becomes a switching reference value in heater control for rapid activation (full conduction control→upper limit hold control or full conduction→power control), and heater temperature by means of this value does not exceed the heat resistance limit.

The computation of step 523 is as per the following equation.
[Equation 4]

$$\text{Target resistance value}=a \times 1200 + b$$

$$a=[R(TH.H)-R(TH.L)] \div [TH.H-TH.L]$$

$$b=[R(TH.L) \times TH.H - R(TH.H) \times TH.L] \div \{TH.H-TH.L\}$$

In the next step 524 it is determined whether the absolute value of the difference between the target heater resistance value computed in step 523 and the previous target heater resistance value is 0.1 or less. Where the present update is the first update, it is compared to an initial value of the target resistance value and in the present embodiment is taken as 2.3Ω. The determination here includes prevention of mislearning and restriction of learning speed. Where YES is determined in step 524, step 525 is proceeded to and the present computed target resistance value is updated as a new target heater resistance value T.Rh as is.

Where NO is determined in step 524, step 527 is proceeded to and where the presently computed target resistance value is large with respect to the previously updated target heater resistance value or the initial value 0.1 is added to the previous value and where it is small 0.1 is subtracted, whereby the target heater resistance value T.Rh.

[Sixth Embodiment]

In the previously described fifth embodiment the target resistance value is computed from the relationship of two heater temperatures-heater resistances. Alternatively, in the present embodiment, the target resistance value is computed from one heater temperature-heater resistance.

Heater resistance changes with respect to heater temperature changes of the present embodiment are 0.0011 (Ω/°C.) as a central value. By using this value, a resistance value of 1200° C. is computed.

Figure 20:
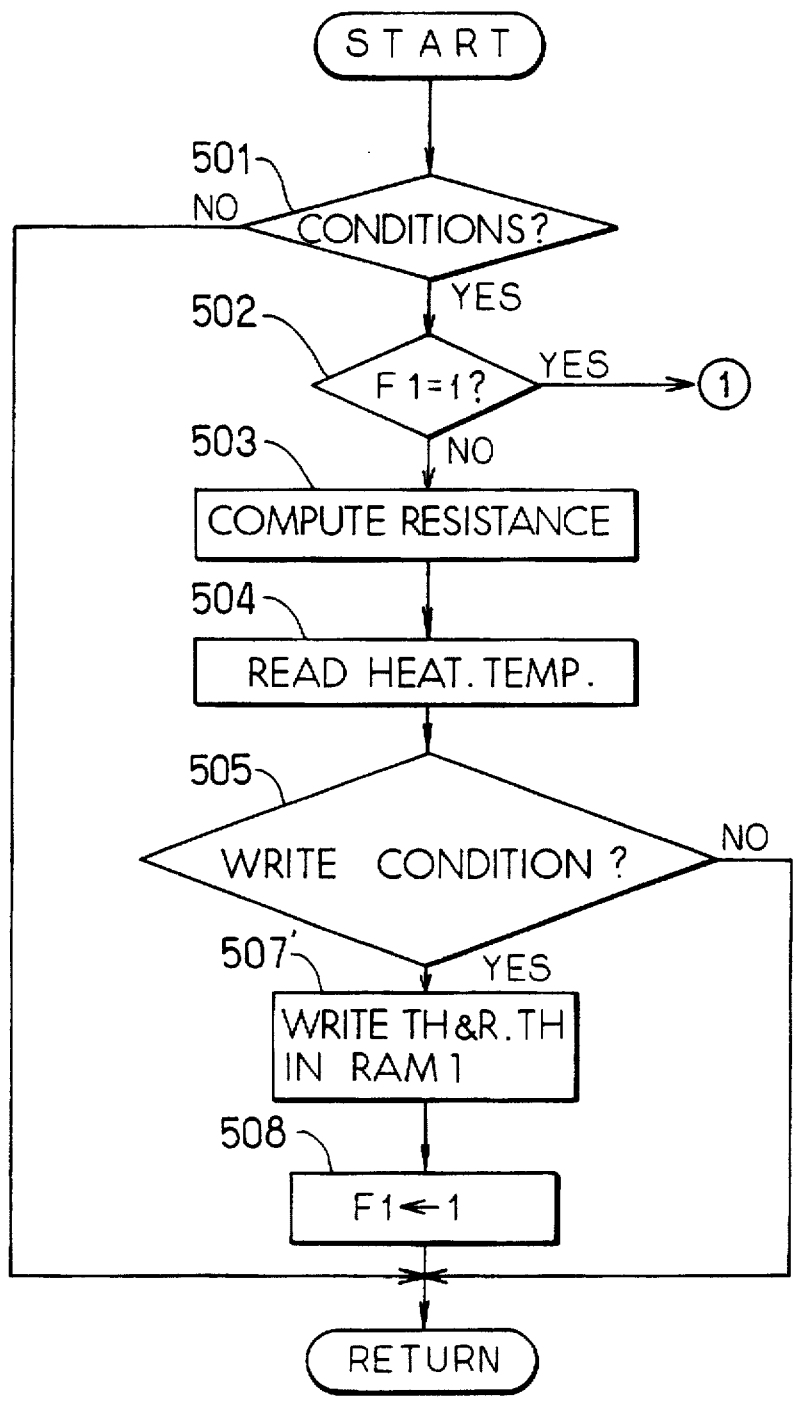
FIG. 20 is a flow chart showing an operation of a microcomputer in a sixth embodiment of the present invention.
Figure 21:
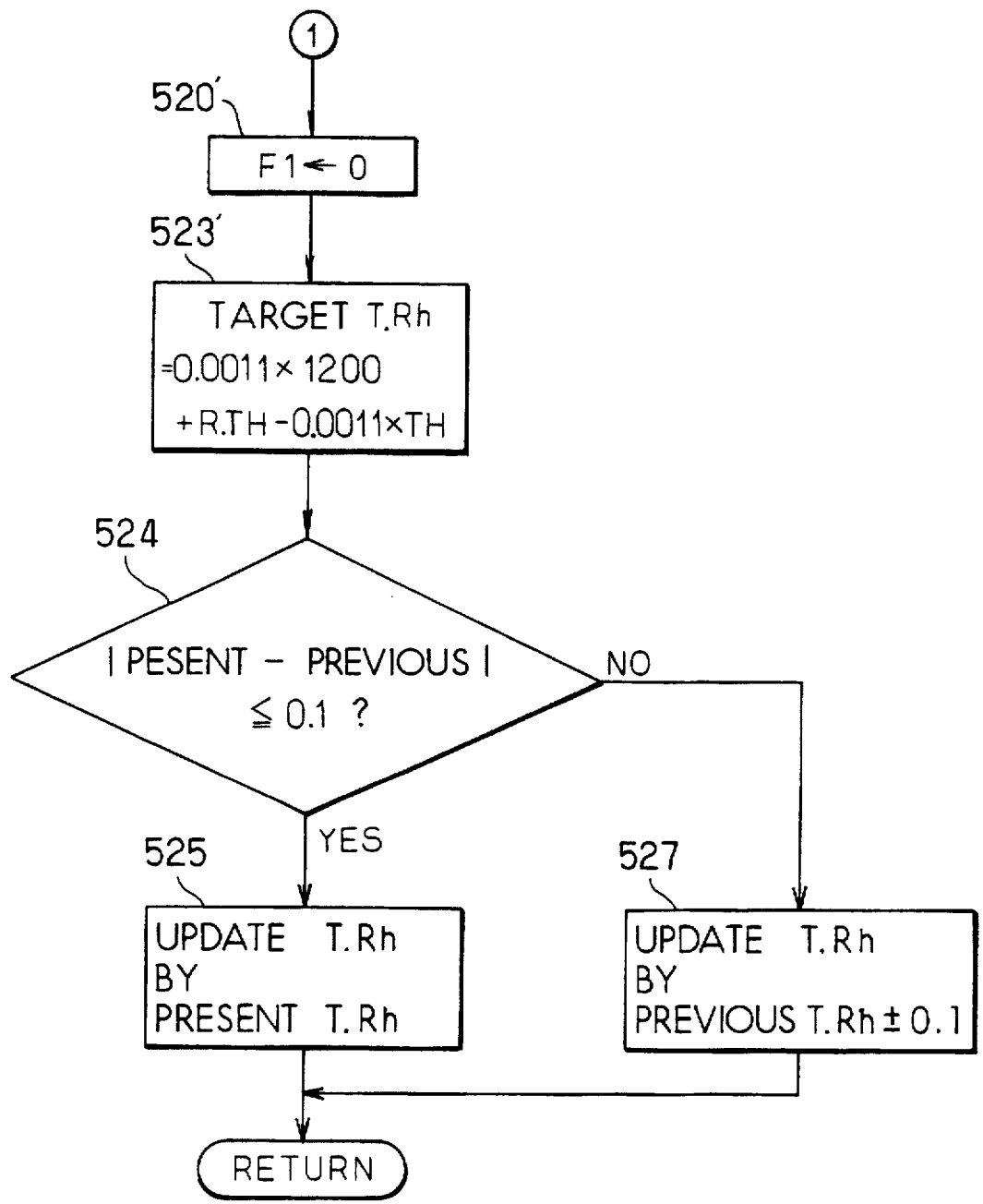
FIG. 21 is a flow chart showing an operation of the microcomputer in the sixth embodiment of the present invention.
Figure 22A:
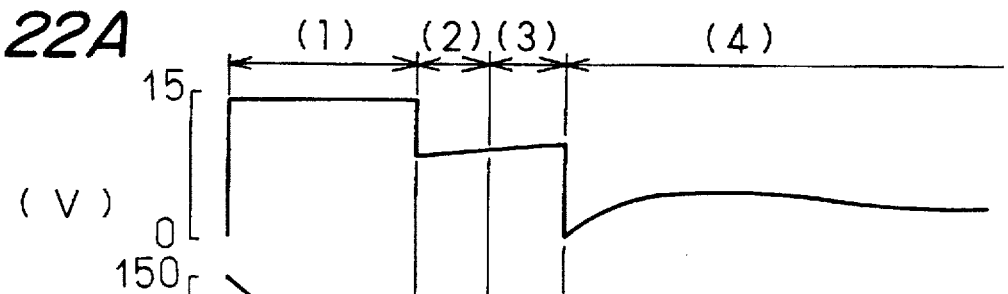
FIGS. 22A, 22B, 22C, and 22D are time charts explaining an operation of a seventh embodiment.
Figure 22B:
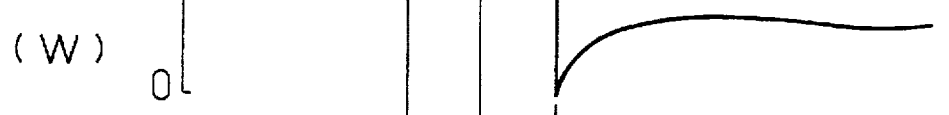
Figure 22C:
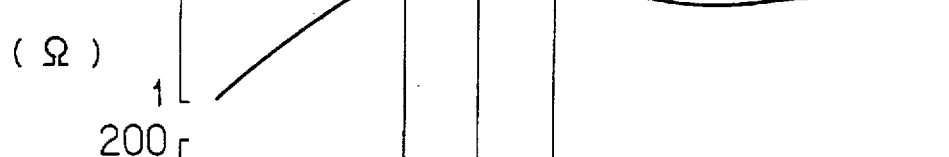
Figure 22D:
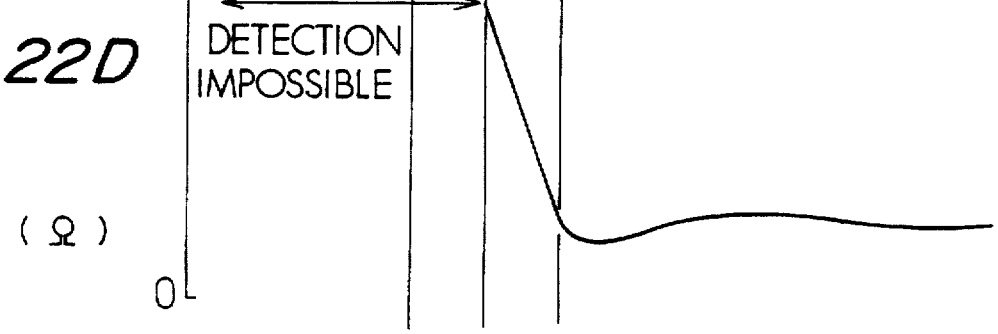

FIGS. 20 and 21 show flow charts of the present embodiment. The flow thereof basically is not changed from the fifth embodiment, but with respect to the fifth embodiment steps, 506, 507, 511 and 512 are omitted and where YES is determined in step 505, step 507' is proceeded to and after the heater temperature TH and heater resistance R.TH are written into RAM1, step 508 is proceeded to, and steps 521 and 522 are omitted and steps 520' and 523' are executed in place of steps 520 and 523. Since these are the only changes, explanation other than with regard to these will be omitted.

Here, in step 520', flag F1 is cleared and in the next step 523', a target heater resistance value TRh is computed as
[Equation 5]

$$T.Rh=0.0011 \times 1200 + RTH - 0.0011 \times TH$$

when at 1200° C. from the resistance change rate 0.0011 (Ω/°C.) as described above and heater temperature TH and heater resistance R.TH. Here the computation value is target heater resistance value T.Rh.

[Seventh Embodiment]

FIGS. 22A through 22D show time charts for heater control of the seventh embodiment. Heater control is divided into sections (1) to (4) from differences in the object and control method thereof. These will each be explained in order.

Section (1) is the full conduction control, and is a control for heating the heater 26 in a short time by supplying the maximum power to the heater 26 when the heater 26 and the sensor are cold. In actuality a voltage is applied at 100% duty.

Sections (2) and (3) are both power controls. In section (3), power is supplied to the heater 26 such that the heater temperature becomes a target upper limit temperature. Here, since heater temperature in a constant state is readily determined from the power supply, even where there are differences in the heater temperature resistance characteristic, where a given power is supplied, the whole of heater 26 becomes a constant temperature. However, when the thermal relationship between the heater 26 and sensor element is in a transition state and where attempting to make the heater temperature constant, it is necessary to change the power supply according to the sensor element temperature. In other words, the amount of radiated heat from the heater 26 when the element temperature is low, therefore much power is required, and conversely, where the element temperature is high, since the amount of heat radiated from the heater 26 decreases, a small amount of power can be supplied. This relationship is shown in FIG. 23. This shows the power required to maintain the heater temperature at 1200° C.

Consequently, section (3) supplies power according to the detected element direct current impedance. Also, section (2) is a region where the element direct current impedance cannot be detected and here a constant power is supplied, serving to connect to the controls from section (1) to section (3). In accordance with FIG. 23, since the element direct current impedance cannot be detected at 600Ω or more, a constant power of 60 W is supplied to the heater at this time (control of section (2)). Thereafter, upon the element temperature increasing and a direct current impedance becoming 600Ω or less, the electric power is supplied to the heater 26 according to the detected direct current impedance (control of section (3)).

Section (4) is an element temperature feedback control. This is a control for estimating the activation state of the element, feedback controlling the power supply to the heater 26 such that the element direct current impedance becomes 30Ω (corresponding to element temperature 700° C.).

Next, an explanation will be given of the shift timing of each control. Transition from full conduction control (1) to power control (2) is made when the interval for executing the control of (1) with the heater 26 and oxygen sensor S being in a cold state reaches a predetermined interval, it shifts to (2). It it is not in a cold state, when the heater resistance value detected from time to time becomes the target heater resistance value or more, it shift to (2). Using these two methods in this way is for preventing the heater temperature from becoming the upper limit temperature or higher when restarting engine.

The shift timing from (2) to (3) is whether or not in a state where the element direct current impedance can be detected. However, when the conditions for shifting from (1) to (2) are established, if in a state where the element direct current impedance can already be detected, (3) is performed without performing (2). The shift timing from (3) to (4) is when the element direct current impedance reaches 30Ω.

Although explanation has been given above in the order of (1) to (4), there are also cases where any one of these controls is skipped and the next control is performed, according to conditions.

Figure 24:
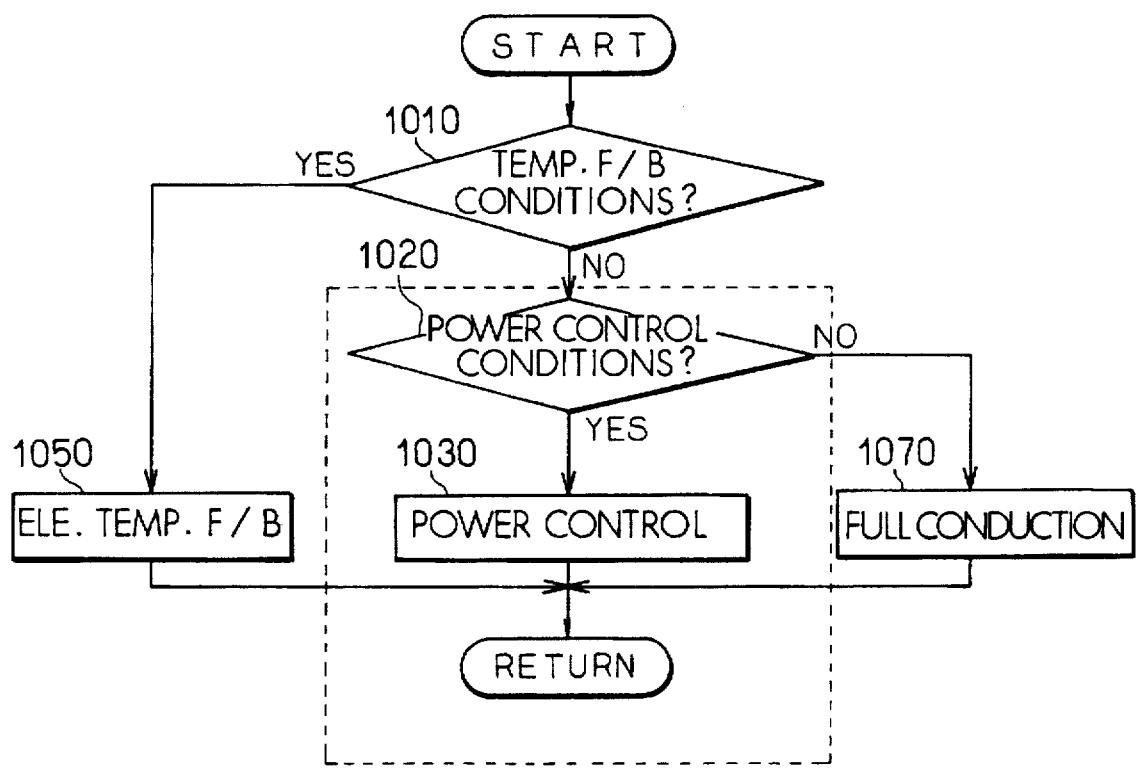
FIG. 24 is a flow chart showing an operation of a microcomputer in the seventh embodiment of the present invention.

Next, the heater control flow chart executed every 100 ms by the microcomputer 70 in the present embodiment in FIG. 24 will be explained. In step 1010 whether the conditions for executing element temperature feedback control or not is determined. This execution condition is whether or not the element direct current impedance is 30Ω or less, and where YES is determined the element is placed in an active state, step 1050 is proceeded to, and element temperature feedback control is executed in the same manner as step 211 in FIG. 12. Also, where element temperature feedback control is executed once, only this control is preformed until the ignition switch is turned off, the other controls of full conduction and power control not being performed. Where NO is determined in step 1010, step 1020 is proceeded to and whether or not the power control execution conditions are established is determined, and where determined as YES step 1030 is proceeded to and power supply to the heater 26 is executed. The details of steps 1020 and 1030 are described below. Where NO is determined in step 1020, step 1070 is proceeded to and full conduction control is executed at 100% duty.

Figure 25:
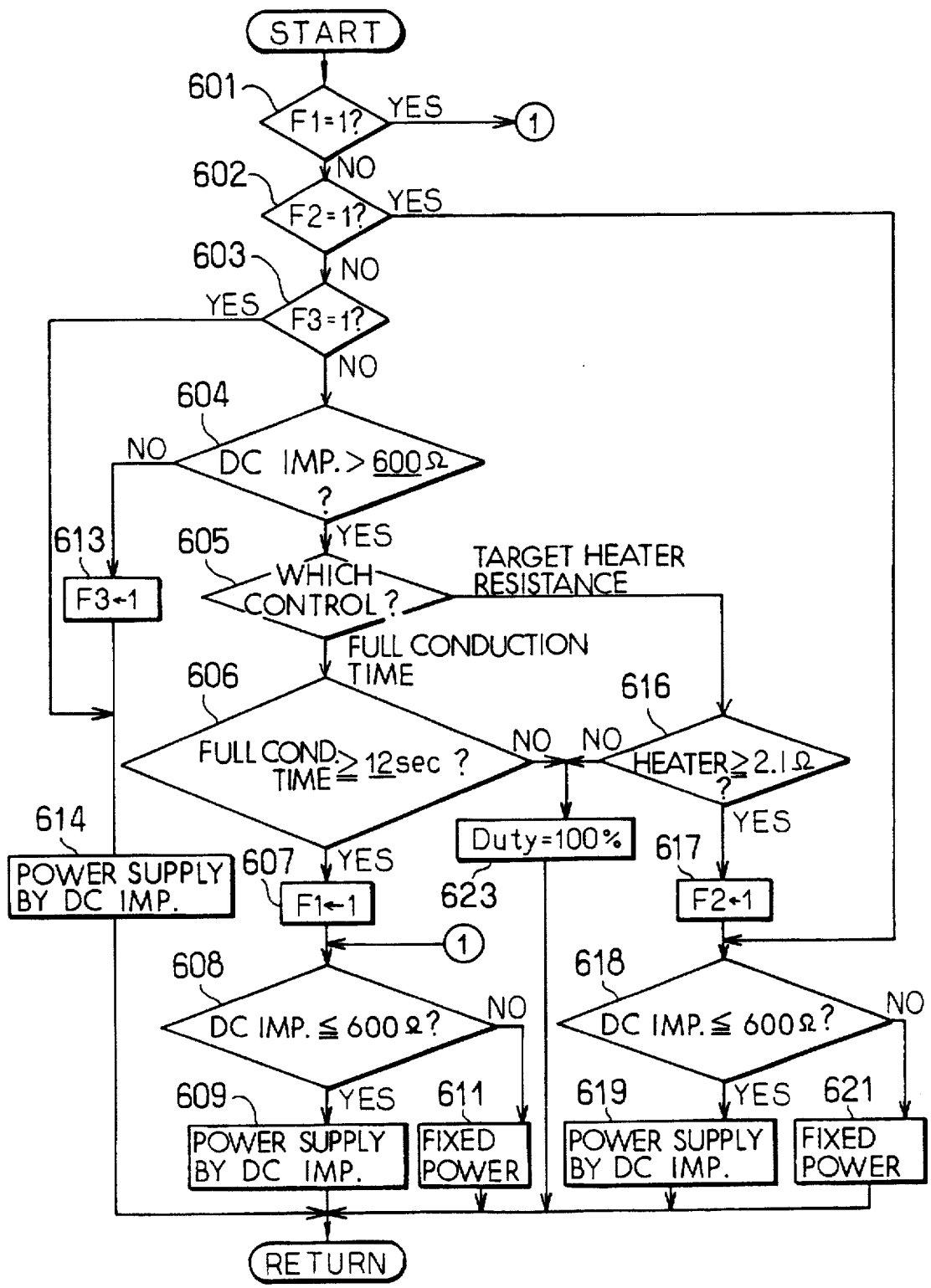
FIG. 25 is a flow chart showing an operation of the microcomputer in the seventh embodiment of the present invention.

The detailed flow of steps 1020 and 1030 is shown in FIG. 25. The flow of FIG. 25 shows controls from after NO of step 101 of FIG. 24. Step 601 determines whether F1 equals 1 and, where F1 does not equal 1, step 602 is proceeded to determine whether F2 is 1 or not. When F2 does not equal 1, step 603 is proceeded to and whether F3 is 1 or not is determined. When F3 does not equal 1 step 604 is proceeded to.

In step 604, whether the element direct current impedance is 600Ω or more is determined. Where NO is determined, step 613 is proceeded to and the flag F3 is set. Then, since YES is determined in step 603 in the following operation cycle, this control is repeatedly executed and does not proceed to step 605 and thereafter. This mode is a mode for shifting from section (1) directly to section (3) without performing the control of section (2) in the time chart of FIG. 22. It is to be noted that the criterion of step 604 is determined from detection performance of the element direct current impedance and normally any one of from 600 to 90Ω (corresponding to element temperature 500° to 600° C.) is used. In step 614 power is supplied in accordance with the element direct current impedance detected based on the relationship of FIG. 23.

FIG. 23 shows power when the heater temperature is 1200° C., but this value is arbitrarily set from the performance and reliability of the heater 26. Also, where the required power cannot be supplied for reasons of battery voltage reduction etc., maximum power is applied at this point in time. When YES is determined in step 604, step 605 is proceeded to. Although the shift timing from full conduction control to power control is determined, which of full conduction control continuation time or the target heater resistance value is to be used is selected. Here, which is selected is determined by the heater resistance value at the time of initiation of current supply. Details are described below.

In step 605, where the determination means for shift time is determined as the full conduction control continuation time period, step 606 is proceeded to and where it is the target heater resistance value, step 616 is proceeded to. It is to be noted that the shift time determination means determined by the heater resistance value at the time of initiation of current supply does not change until the ignition switch is turned off. Thereby, during the continuous heater control from the ignition switch ON to OFF, only one of the shift control of step 606 or the control from step 616 onward is performed.

Then, where proceeding to step 606, it is determined whether the full conduction control continuation period has been 12 sec. or longer. Where YES is determined in step 606 and full conduction control is performed thereafter, this is a region where there is a possibility that the heat resistance temperature of the heater 26 may be exceeded, in which case the power control is shifted to from step 607 onwards. Here, the determination time is determined by the heating performance and heat resistance limit of the heater, and in the present embodiment this is taken as 12 sec. Where NO is determined in step 606, step 623 is proceeded to and full conduction control at 100% duty continues to be performed. Where YES is determined in step 606 the flag F1 is set in step 607 and the process of the next operation is repeated from here onward.

In the next step 608, it is determined whether the element direct current impedance is 600Ω or less. Where NO is determined in step 608, this is a state where the element temperature has not yet risen and the element direct current impedance cannot be detected, in which case a fixed power is supplied in step 611. Based on FIG. 23 the power at this time is 60 W. It is preferable to use as the criterion of step 608 the same value as in step 604. Where YES is determined in step 608, step 609 is proceeded to and power is supplied according to the element direct current impedance in the same manner as in step 614.

Where the target heater resistance value is used as a shift time determination means for step 605, step 616 is proceeded to. In step 616 it is determined whether or not the heater resistance value is 2.1Ω or more. Where YES is determined in step 616 there is a possibility that inconsistent lower limit products of the heater temperature resistant characteristic exceed the heat resistance temperature, and power control is shifted to from step 617 onwards. Where NO is determined in step 616, step 623 is proceeded to and full conduction control continues to be performed.

In step 617 the flag F2 is set and control is repeatedly performed from here onward by determining YES in step 602. Since the next steps 618 to 621 are similar controls to the previously described steps 608 to 611, explanation thereof will be omitted for brevity. Here, power supply in steps 609, 611, 614, 619 and 621 by setting the power obtained in each of steps 609, 611, 614, 619 and 621 in place of the 21 W in step 214 of FIG. 8 and performing steps 215 and 217, each of these set powers can be supplied to the heater 26.

Figure 26:
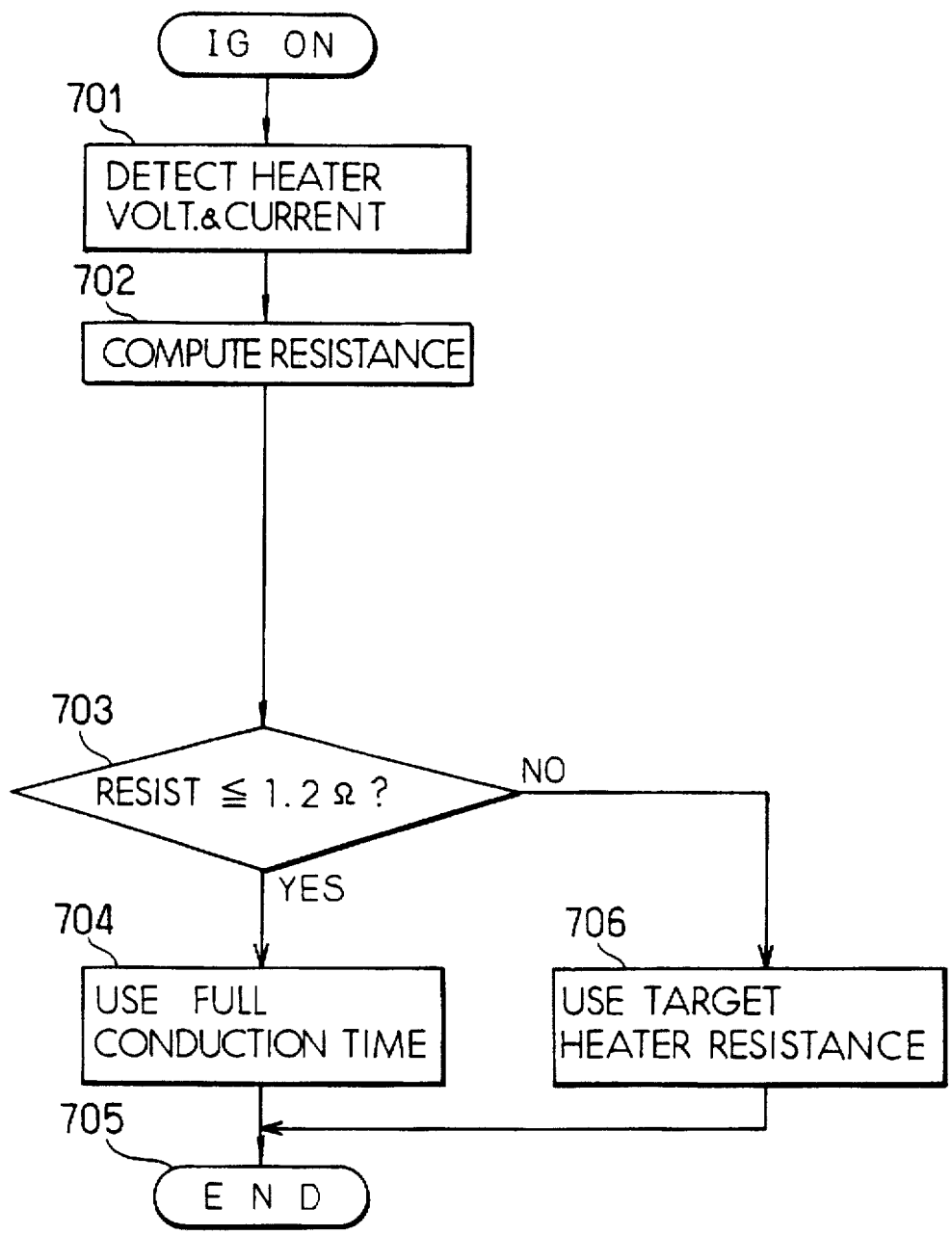
FIG. 26 is a flow chart showing an operation of the microcomputer in the seventh embodiment of the present invention.

Next, the determining method for the full conduction control continuation period or the target heater resistance selected in step 605 will be explained in detail. FIG. 26 is a flow chart showing the determination method for the shift time determination means. This control is performed only once when the ignition switch is turned on and the current supply to the heater 26 is initiated. In step 701 the voltage and current of the heater are detected and the heater resistance value is computed in step 702 based thereon. Where it is determined that accurate heater voltage and current cannot be detected due to the effect of a spike current immediately after heater current supply, after a constant period, e.g. 100 ms later, has passed after heater current supply, there is no problem with performing detection.

In the next step 703, whether the heater resistance value computed in step 702 is 1.2Ω or less is determined. Where YES is determined in step 703, it is determined whether the heater 26 and element are in a cold state or in the vicinity of a normal temperature, step 704 is proceeded to, and it is determined that the continuation period of full conduction control is to be used as the determination result of shift timing from the full conduction control to power control in step 605 of FIG. 25. Also, where NO is determined in step 703, it is considered that it is possible that the heater temperature has exceeded the heat resistance temperature in a continuous period without being sufficiently cooled, step 706 is proceeded to and it is determined that the target heater resistance is to be used as the determination result of shift timing in step 605 of FIG. 25.

In the seventh embodiment constant power control of section (2) of FIG. 22 is omitted and control shifts directly from section (1) to section (3), and it is possible to continuously control heater power at the element temperature response power control of section (3) while omitting the element temperature feedback control of section (4).

[Eighth Embodiment]

The present embodiment performs heater control in the same way while updating the target heater resistance in step 616 of the sixth embodiment. Updating of the target heater resistance detects the heater temperature resistance characteristic and performs updating based on this value. The heater temperature resistance characteristic estimates heater temperature from the power supply, engine revolutions and air intake pressure (air intake amount), and can attain detection of the heater resistance at that time. Also, in the seventh embodiment, the heater temperature may be estimated as in the fourth to sixth embodiments, and can update the target heater resistance value for determining the shift timing from full conduction control to power control.

[Ninth Embodiment]

Figure 27:
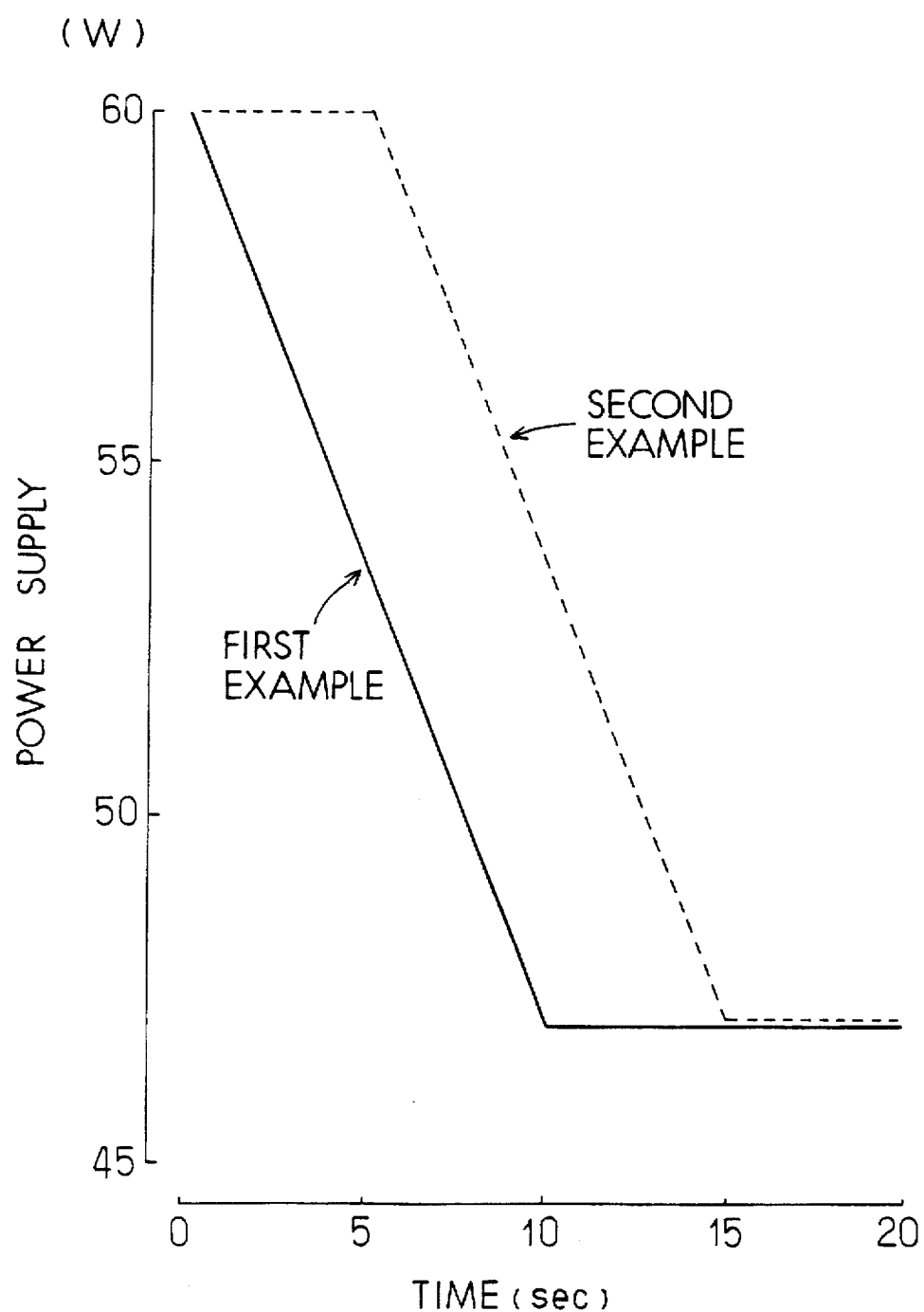
FIG. 27 is a characteristic graph showing power supply with respect to a power control intermittent period in a ninth embodiment.

Although power control of the seventh embodiment can vary the power supply according to the element direct current impedance in steps 609 and 619, in the present embodiment the power supply is variable with respect to a continuation period from the shift to power control. Although power supply with respect to the continuation period is shown in FIG. 27, it varies according to the heating performance and heat resistance temperature of the heater 26. FIG. 27 shows two examples of a solid line and broken line. Here, although power varies linearly, it may also vary in a curve.

[Tenth Embodiment]

In the sixth embodiment, determination of shift timing from full conduction control to power control is performed according to the continuation time in step 606 at the heater cooling time (state where the heater resistance at the current supply initiation time to the heater 26 is a predetermined value or less). In the present embodiment, in place thereof, determination is performed by the element direct current impedance. Further, it is also possible to determine from both the element direct current impedance and full conduction control continuation period.

[Eleventh Embodiment]

FIGS. 28A through 28C show time charts for heater control of the eleventh embodiment. Heater control is divided into sections (1) to (3) from differences in the purpose and control method thereof, and these will be explained in order.

The section (1) is a full conduction control, and is a control for heating the heater 26 in a short time by supplying maximum power to the heater 26 when the heater 26 and the sensor are cold. In actuality, a voltage is applied at 100% duty.

The section (2) is a power control. This supplies power to the heater 26 such that the heater temperature is kept at a target upper limit temperature. Here, since heater temperature in a constant state is readily determined from the power supply, even where there are differences in the heater temperature resistance characteristic, where a given power is supplied, the whole of heater 26 becomes a constant temperature. However, when the thermal relationship between the heater 26 and sensor element is in a transition state and where attempting to make the heater temperature constant, it is necessary to change the power supply according to the sensor element temperature. In other words, the amount of radiated heat from the heater 26 when the element temperature is low, therefore much power is required, and conversely, where the element temperature is high, since the amount of heat radiated from the heater 26 decreases, a small amount of power can be supplied. This relationship is shown in FIG. 23. This shows the power required to maintain the heater temperature at 1200° C.

Consequently, section (2) supplies power for the heater according to a detected element direct current impedance (element internal resistance).

The section (3) is an element temperature feedback control. This is a control for estimating the activation state of the element, feedback controlling the power supply to the heater 26 such that the element direct current impedance is a reference value ZDCD, 30Ω (corresponding to element temperature 700° C.). During this element feedback control, if the power supply to the heater 26 exceeds the upper limit value, the power supply to the heater 26 is restricted.

Next, explanation will be given of the shift timings of each of the controls. From full conduction control (1) to power control (2), the actual power supply cumulative amount reaches a target cumulative power supply (the target cumulative power supply is set based on the initial heater resistance value such that the temperature of the heater 26 from when current supply commences by means of full current supply to the heater 26 reaches an initial heating temperature of 1200° C. in the vicinity of the heat resistance limit temperature of the heater 26), and shifts to power control (2) when the heater resistance reaches a heater resistance learning value (described below). Here, considering the large differences as shown in FIG. 9 in the relationship of the heater resistance temperature characteristic, using the heater 26 having whatever heater resistance temperature characteristic from among these, naturally the target cumulative power supply is set based on the initial heater resistance, based on the difference in upper limit heater resistance temperature characteristic of FIG. 9 so that 1200° C. which is the heat resistance limit of the heater 26 is not exceeded.

Here, until both the actual power supply cumulative amount to the heater 26 reaches the target cumulative power supply and the heater resistance value reaches the heater resistance learning value and both are satisfied, the standby of the full conduction control (1), in a state where the heater resistance learning value in the initial operation of the internal combustion engine has not been learned, it for supplying a large power by means of the full conduction control (1) to the heater 26 until the power supply cumulative amount reaches the target cumulative power supply, whereafter, after the heater resistance learning value has been sufficiently learned, it is for controlling such that a large power is supplied to the heater 26 by means of the full conduction control (1) until the heater resistance value reaches the heater resistance learning value. Here, the shift time from (1) to (2), in order for the element direct current impedance to become a sufficiently smaller value than the 600Ω (FIG. 23) capable of detecting this value, power supply control to the heater 26 according to the element direct current impedance of (2) is immediately performed.

The shift timing from (2) to (3) is the time when the element direct current impedance reaches a switching setting value ZDCD1:30Ω (corresponding to element temperature 700° C.) equivalent to the target value ZDCD. Here, the switching setting value ZDCD1 can be set to a somewhat higher value or somewhat lower value than the target value ZDCD. Also, the heater resistance value is learned in the shift timing from (2) to (3). Here, the learning of this heater resistance value is not restricted to this shift timing from (2) to (3), and learning of the heater resistance value when the heater temperature is in the vicinity of 1200° C. from when the heater temperature is controlled in the vicinity of 1200° C. if during the power control of (2) is possible. Thereby, as shown in FIG. 9, even where differences occur in each product between the heater resistance value and the heater temperature, the heater resistance value can be learned when the heater temperature is in the vicinity of 1200° C.

Until the heater resistance learning value learned in this way is reached, large power is supplied to the heater 26 by the full conduction control (1), fast activation of the oxygen sensor S can be achieved without using an expensive temperature sensor having a sufficient durability at high temperatures and without adversely affecting the durability of the heater 26.

Although the above was explained in the order (1) to (3), there are also cases where any one of these controls can be skipped and the next control executed depending on conditions.

Next, explanation will be given of the heater control flow chart of the present embodiment shown in FIG. 29 and FIG. 30 executed by the microcomputer 70 every 100 ms. In step 801 whether the ignition switch is ON or not is determined, and when the ignition switch is ON step 802 is proceeded to, while when it is not ON step 806 is proceeded to. In step 802 it is determined whether an initial completion flag XINIT is 0 or not (this initial completion flag XINIT is reset to 0 when the ignition switch is activated), and when the initial completion flag XINIT is 0 step 803 is proceeded to, while when the initial completion flag XINIT is not 0 step 806 is proceeded to.

Figure 37:
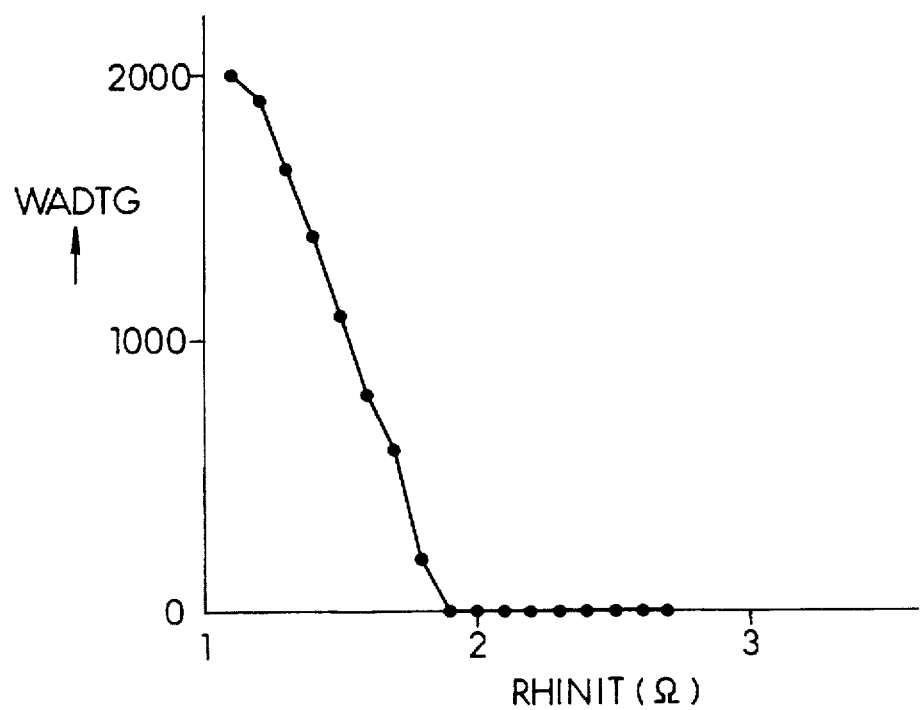
FIG. 37 is a characteristic graph showing a target cumulative power supply with respect to an initial value of heater resistance.

In step 803 power is supplied to the heater 26 and the heater resistance value RH obtained from the heater current IH and heater voltage VH detected at that time is detected as the initial heater resistance value RHINT. In the next step 804 the target cumulative power supply WADTG is searched from the map (set such that the target cumulative power supply WADTG decreases to the extent that the initial heater resistance value RHINT increases, i.e. to the extent that the initial temperature is high, and the target cumulative power supply WADTG becomes 0 when the initial heater resistance value is a predetermined value, e.g. 1.9Ω or more) previously stored in a ROM as shown in FIG. 37 to obtain a linear interpolation. In the next step 805, step 806 is proceeded to after the initial completion flag XINIT is set to 1. Consequently, upon the target cumulative power supply WADTG being obtained from when the ignition switch is activated, thereafter "NO" is determined in step 802 and step 806 is proceeded to.

Figure 28:
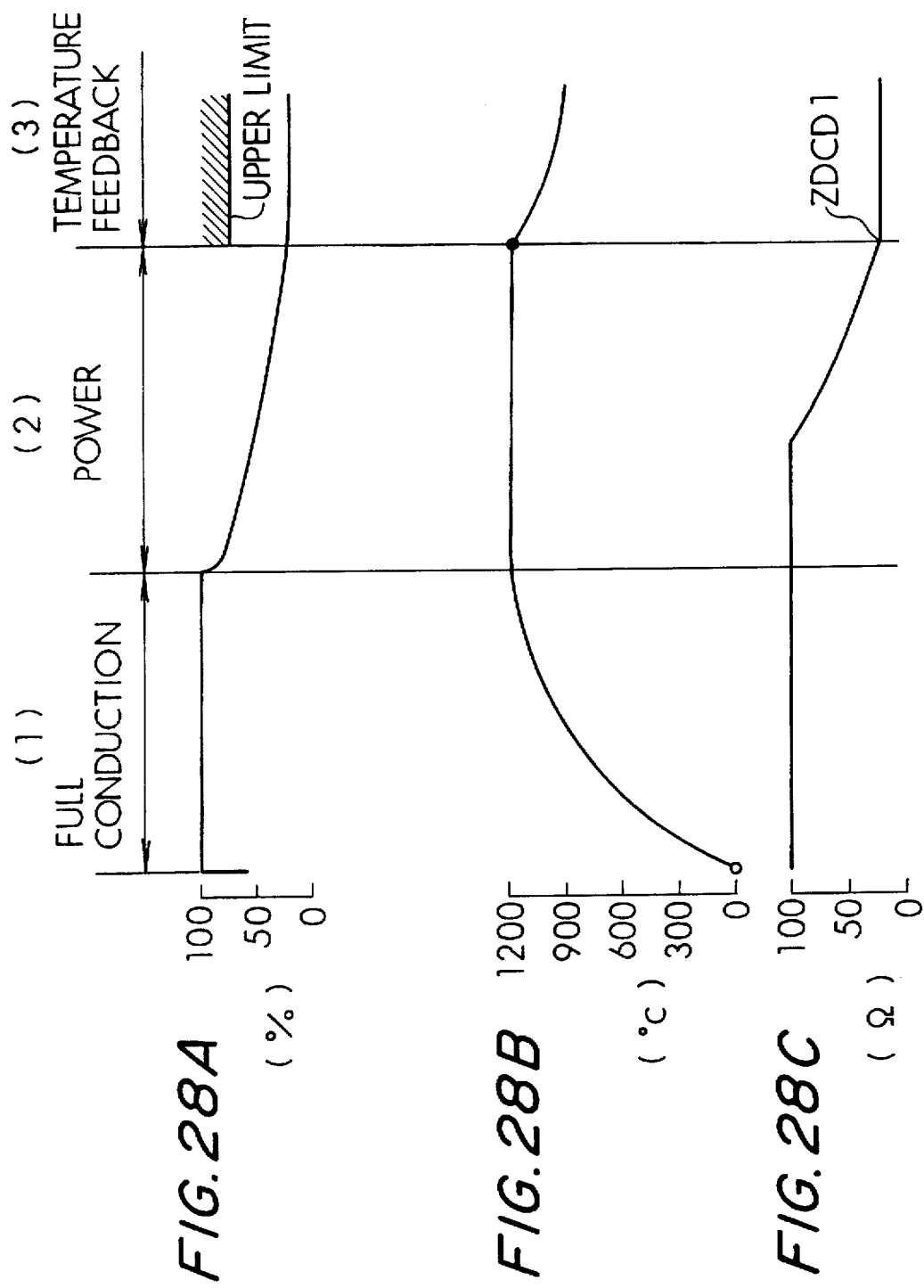
FIGS. 28A, 28B, and 28C are time charts explaining an operation of an eleventh embodiment.

In step 806 whether an element temperature feedback execution flag XEFB is 1 or not is determined, and where the element temperature feedback execution flag XEFB is 1 step 840 is proceeded to and element temperature feedback control shown in (3) of FIG. 28 is executed. When the element temperature feedback execution flag XEFB is not 1, step 807 is proceeded to and it is determined whether the internal resistance ZDC of the oxygen sensor S (detected in the same manner as in step 822 of FIG. 32 described hereafter) is the same or less than the value ZDCD1: 30Ω (equivalent to element temperature 700° C.) corresponding to the element temperature feedback execution temperature. Where ZDC is equal to or less than ZDCD1 step 815 is proceeded to, while where ZDC is not equal to or less than ZDCD1 step 808 is proceeded to. In step 808 it is determined whether the actual heater resistance value RH obtained at that time is equal to or more than the heater resistance learning value RHADP, and where the actual heater resistance value RH is equal to or more than the heater resistance learning value RHADP step 809 is proceeded to, while where the actual heater resistance value RH is not equal to or more than the heater resistance learning value RHADP step 810 is proceeded to and full conduction control shown in (1) of FIG. 28 is executed.

Also, in step 809 whether the actual cumulative power WADD supplied to the heater 26 is equal to or more than the target cumulative power supply WATDG is determined, and when the actual cumulative power WADD is not equal to or more than the target cumulative power supply WATDG step 810 is proceeded to, and when the actual cumulative power WADD is equal to or more than the target cumulative power supply WATDG step 820 is proceeded to and the power control shown in (2) of FIG. 28 is executed. Also, whether a power control execution flag XEWAT is 1 or not is determined in step 815, and when the power control execution flag XEWAT is not 1 step 840 is proceeded to, while when the power control execution flag XEWAT is 1, since this is a switching point from power control to element temperature feedback control, step 830 is proceeded to and after the heater resistance value is learned as RHADP step 840 is proceeded to.

Figure 31:
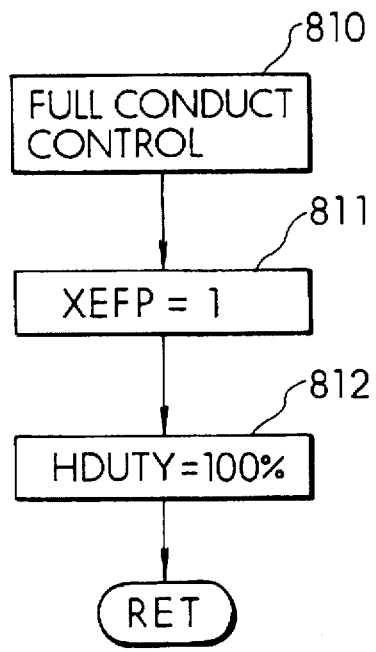
FIG. 31 is a flow chart showing an operation of full current supply control of the microcomputer in the eleventh embodiment of the present invention.

Next, the detailed flow of the full conduction control of step 810 is shown in FIG. 31. First, after a full conduction control execution flag XEFP is set to 1 in step 811, step 812 is proceeded to and the control duty HDUTY of the heater control circuit 80 is controlled at 100% duty and full power is supplied to the heater from the battery 81.

Figure 32:
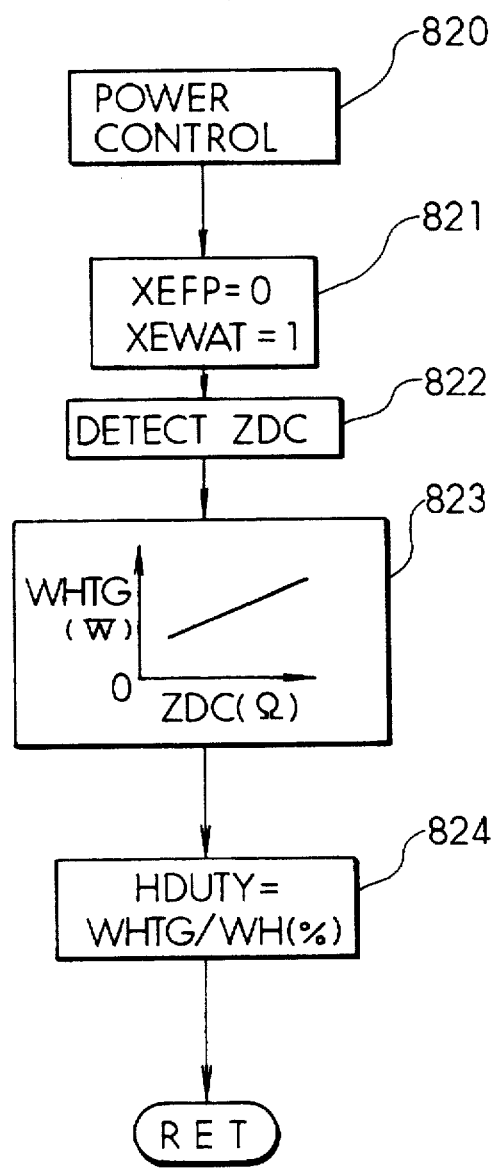
FIG. 32 is a flow chart showing an operation of power supply control of the microcomputer in the eleventh embodiment of the present invention.

Next, the detailed flow of the power control of step 820 is shown in FIG. 32. First, after the full conduction control execution flag XEFP is reset to 0 and the power control execution flag XEWAT is set to 1 in step 821, step 822 is proceeded to and the element internal resistance value ZDC is computed by the element application voltage Vneg and the negative current Ineg detected in the sensor current detection circuit 50 as ZDC=Vneg/Ineg. Next, in step 823 the target power supply WHTG is searched from the map shown in FIG. 23 and previously stored in the ROM, based on the internal resistance value ZDC of the oxygen sensor S, to obtain a linear interpolation. Next, in step 824 the control duty HDUTY of the heater control circuit 80 is set by calculating WHTG/WH (%) from the target power supply WHTG and present actual heater power WH.

Figure 33:
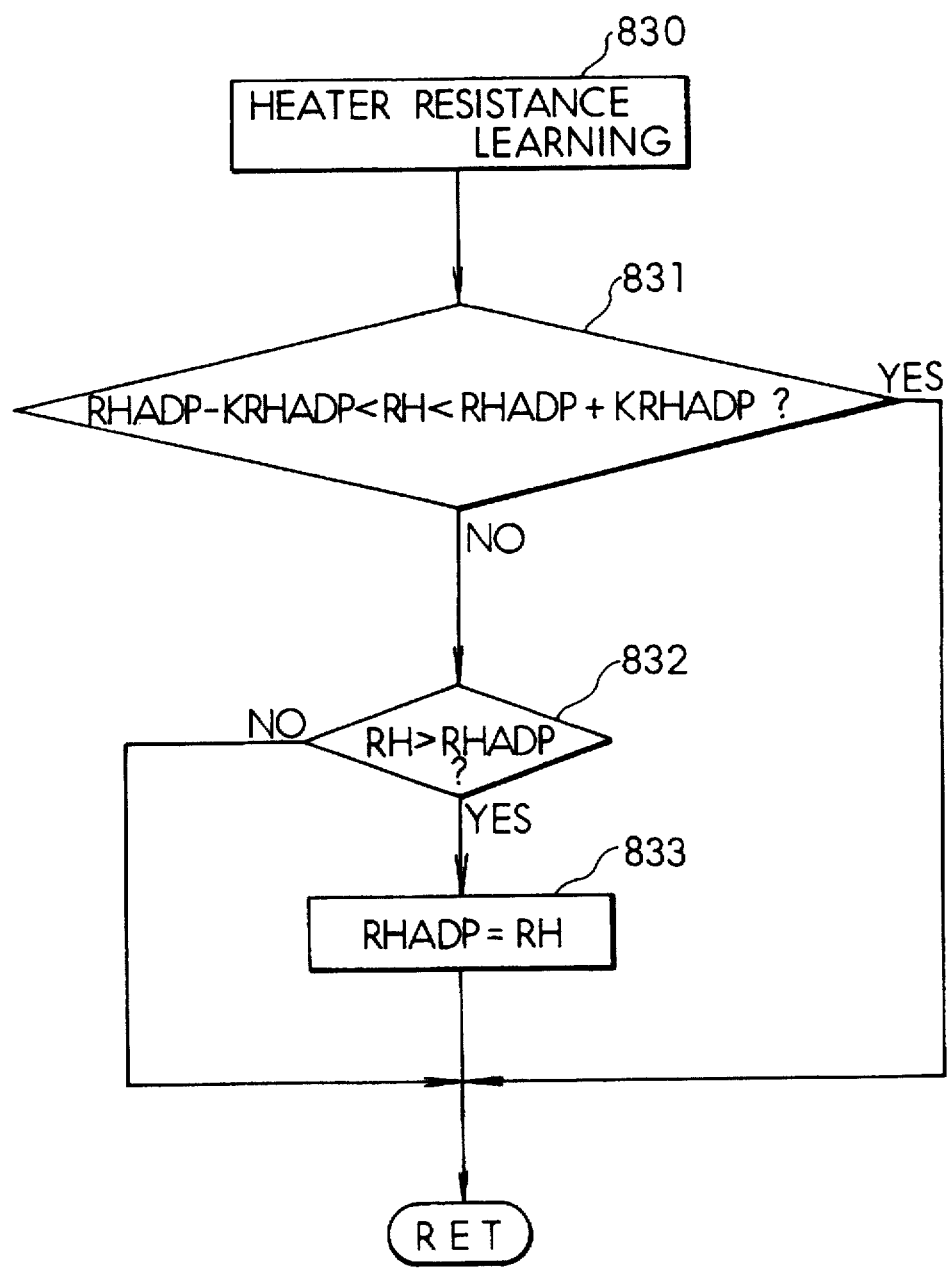
FIG. 33 is a flow chart showing an operation of a heater resistance learning routine of the microcomputer in the eleventh embodiment of the present invention.

Next, the detailed flow of the heater resistance learning of step 830 is shown in FIG. 33. First, it is determined in step 831 whether the present heater resistance value RH is within the limit of a neutral zone of ±KRHADP with respect to a present heater resistance learning value RHADP, and where it is within this neutral zone limit the present routine is exited without updating the heater resistance learning value RHADP. Where it is not within the limit of the neutral zone, step 832 is proceeded to since the heater resistance learning value RHADP is off by a predetermined value. It is determined whether the present heater resistance value RH is greater than the present heater resistance learning value RHADP. Where it is greater, step 833 is proceeded to and the present heater resistance value RH (an average value, central value, integral value, etc. of the heater resistance value RH during execution of power control may be used) is set as the heater resistance learning value RHADP, while where it is not greater the present routine is exited without updating the heater resistance learning value RHADP. Here, it is preferable that the value of the heater resistance learning value RHADP be held and stored in the backup RAM after the ignition switch is turned off.

Figure 34:
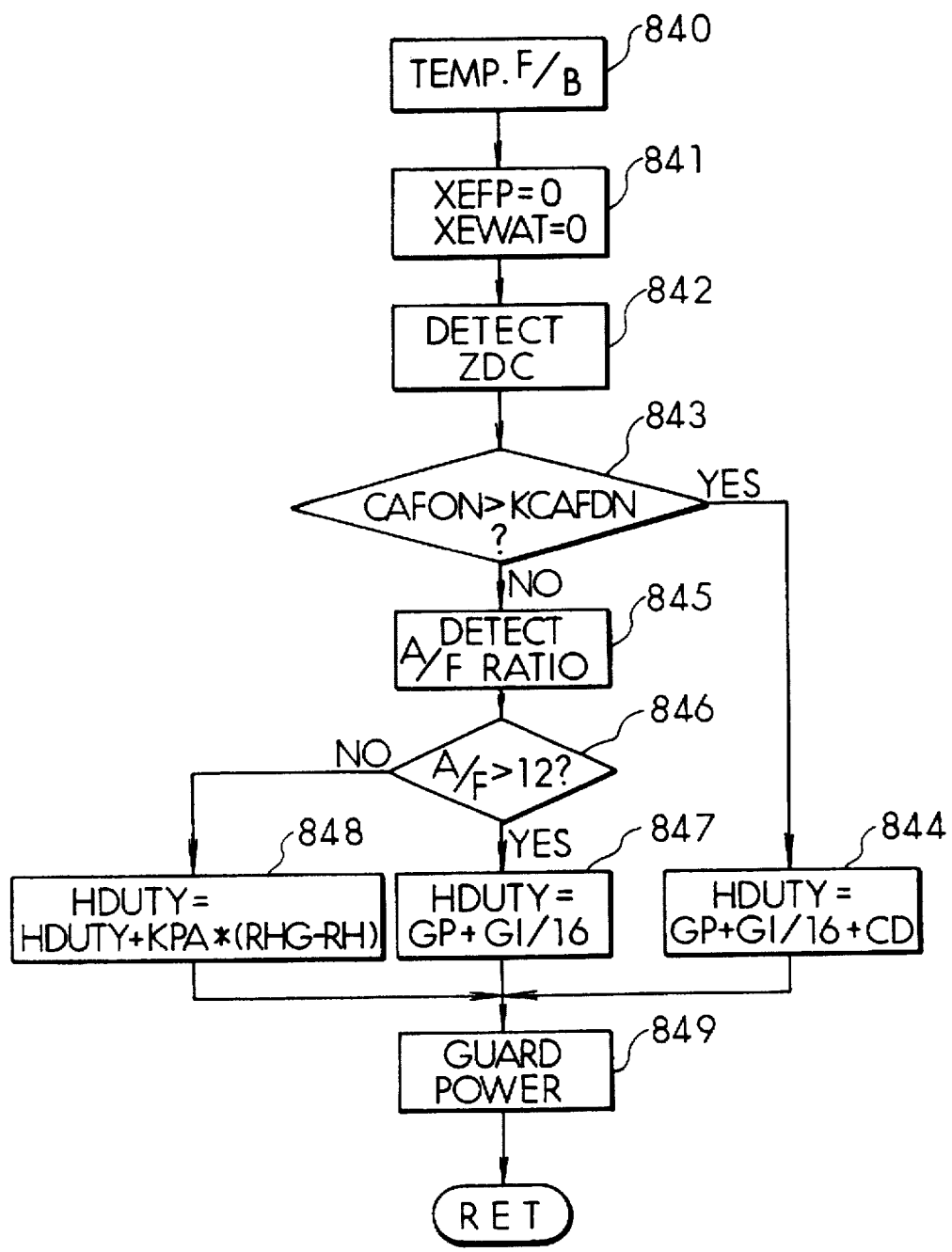
FIG. 34 is a flow chart showing an operation of an element temperature feedback control of the microcomputer in the eleventh embodiment of the present invention.

Next, the detailed flow of the element temperature feedback control of step 840 is shown in FIG. 34. First, after the full conduction control execution flag XEFP and the power control execution flag XEWAT are set to 0 in step 841. Step 842 is proceeded to and the element internal resistance value ZDC is computed by the element application voltage Vneg and the negative current Ineg detected in the sensor current detection circuit 50 as ZDC=Vneg/Ineg. Next, in step 843 it is determined whether a count value CAFON of a counter for counting the time after the ignition switch is turned ON is equal to or greater than a predetermined value KCAFON (e.g. 24.5 sec), and when it is equal to or greater than the predetermined value KCAFON step 844 is proceeded to, and where it is not equal to or greater than the predetermined value KCAFON step 845 is proceeded to.

In step 845, after the oxygen concentration in the exhaust gas, i.e. the air-fuel ratio in the mixed gases of the internal combustion engine, is detected by the limit current Ipos of the oxygen sensor S detected by the sensor current detection circuit 50, step 846 is proceeded to. In step 846 it is determined whether the air-fuel ratio detected by step 845 is 12 or more, and where the air-fuel ratio is 12 or more step 847 is proceeded to, while if the air-fuel ratio is not 12 or more step 848 is proceeded to.

In step 844, after calculating the control duty HDUTY of the heater control circuit 80 by GP+GI/16+GD using a proportional term GP, an integral term GI and a differential term GD, step 849 is proceeded to. In step 847, after calculating the control duty HDUTY of the heater control circuit 80 by GP+GI/16 using the proportional term GP and the integral term GI, step 849 is proceeded to. Here, the proportional term GP is computed by GP=KP×(ZDC−ZDCD), the integral term GI is computed by previous GI+KI×(ZDC−ZDCD), and the differential term GD is computed by GD=KD×(present ZDC−previous ZDC). Here, KP, KI and KD are constants.

In step 848, after calculating the control duty HDUTY of the heater control circuit 80 by previous HDUTY+KPA× (RHG−RH), using the previous control duty HDUTY, a constant KPA, the target heater resistance value RHG (2.1Ω is equivalent to 1020° C.) and the heater resistance value RH, step 849 is proceeded to. Here, if the air-fuel ratio is not 12 or more in step 848, execution of heater resistance feedback control without element temperature feedback control is because element temperature feedback control using the proportional, integral and differential by steps 844 and 847 is troublesome with respect to the characteristic of the oxygen sensor S where the air-fuel ratio is 12 or more. Also, in step 849 a guard process is performed so that the power supply of the heater 26 during the element temperature feedback control does not meet or exceed the upper limit value.

Figure 35:
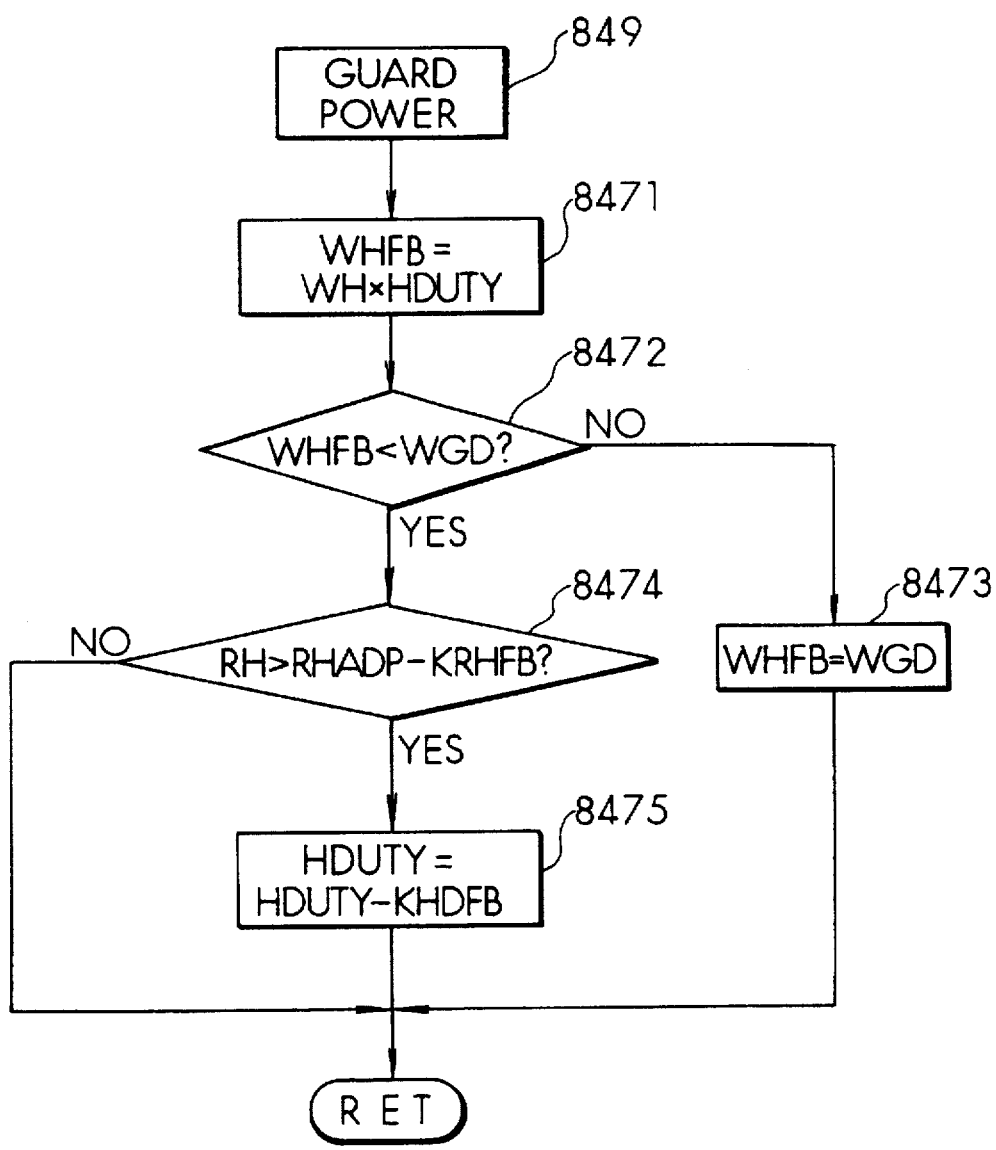
FIG. 35 is a flow chart showing an operation of a power supply guard process of the microcomputer in the eleventh embodiment of the present invention.

Next, the detailed flow of the power supply guard process of step 849 is shown in FIG. 35. First, after a set feedback power WHFB during element temperature feedback control in step 8471 is obtained by multiplying the heater power WH at that time and the control duty HDUTY, step 8472 is proceeded to. In step 8472 it is determined whether the set feedback power WHFB is equal to or less than an upper limit guard power WGD during element temperature feedback control, and where WHFB is not equal to or less than WGD step 8473 is proceeded to, while where WHFB is equal to or less than WGD step 8474 is proceeded to. In step 8473 after the set feedback power WHFB is set to the upper guard power WGD, the power supply guard process is finished.

In step 8474 it is determined whether the heater resistance RH is larger than a value wherein a constant KRHFB is subtracted from the heater resistance learning value RHADP, and where the heater resistance RH is larger than the value wherein a constant KRHFB is subtracted from the heater resistance learning value RHADP step 8475 is proceeded to, while the heater resistance RH is not larger than a value wherein a constant KRHFB is subtracted from the heater resistance learning value RHADP the power supply guard process is finished. In step 8475 the constant KHDFB is subtracted from the previous control duty HDUTY to make the present control duty HDUTY.

Next, the heater operational value process executed at every control cycle (128 ms) of the heater 26 will be explained in FIG. 36. First, after the heater current value IH is detected by the current detection resistor 82 in step 851, the heater voltage VH is detected in the next step 852. In the next step 853 the heater voltage VH is divided by the heater current value IH to obtain the heater resistance value RH, and after the heater voltage VH and the heater current value IH are multiplied to obtain the present heater power supply WH in the next step 854, the present actual heater power supply cumulative value WADD is obtained by adding the present heater power supply WH to the previous actual heater power supply cumulative value WADD in the following step 855. Then, these obtained values are suitably used in FIGS. 29 to 35.

[Twelfth Embodiment]

In the above-described eleventh embodiment, when controlling in a state where the heater is cooled although the element itself of the oxygen sensor S is not cooled, for example, a state where the element portion of the oxygen sensor S at exhaust temperature awaits temperature and the heater power is low due to element temperature feedback control, the internal combustion engine is stopped, and when the internal combustion engine is restarted immediately thereafter etc., upon determining a target cumulative power supply WADTG only at heater initiation resistance value RHINT, the element reaches an abnormal temperature and there is a possibility of reaching element damage. Here, element temperature and heater temperature are detected at an initial time when detection of the air-fuel ratio is unnecessary, from which value the target cumulative power supply WADTG is determined. Further, when the initial element temperature is a predetermined value or more, this is improved by the durability of the element due to termination of the full conduction control (1).

Also, although the cumulative power supply necessary for the heater temperature to be the target temperature is basically constant, the cumulative power supply necessary for the heater temperature to be the target temperature changes due to heat radiating operation of the heater 26. Here, the heat radiation amount of the heater 26 is obtained by the difference between the heater temperature and the element temperature and accumulation of power supply intervals. Also, where the voltage applied to the heater 26 from the battery 81 is low, since the power supplied to the heater 26 decreases, it is necessary to extend the full power supply interval. Here, interpolation the target cumulative power supply WADTG obtained by the heater initial resistance value RHINT by combining heater temperature, element temperature, full power supply time and battery voltage (heater voltage) (may also be any one thereof) is effective.

Figure 39:
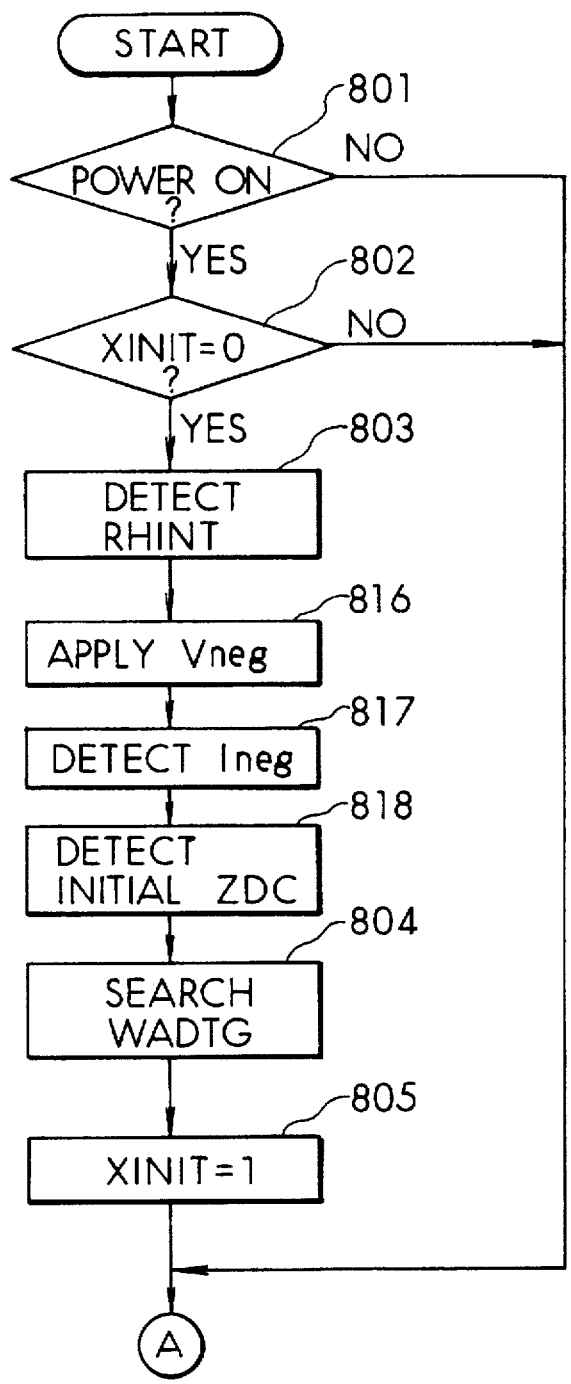
FIG. 39 is a flow chart showing an operation of a microcomputer in a twelfth embodiment of the present invention.

Those portions which differ from the eleventh embodiment described above will be explained below by way of the flow charts of FIGS. 39 to 42 of heater control executed by the microcomputer 70 in the present embodiment. The present embodiment uses the same flow charts as in FIGS. 31 to 35 in the eleventh embodiment. FIG. 39 is used in place of FIG. 29, wherein after step 803, step 816 is proceeded to and after the negative bias voltage Vneg is applied to the oxygen sensor S, step 817 is proceeded to and the temperature current Ineg is detected, while in step 818, after the initial element impedance ZDC is computed as ZDC=Vneg/Ineg, step 804 is proceeded to.

In step 804, the initial target cumulative power supply WADTG is searched, based on the initial heater resistance value RHINT and the initial element impedance ZDC, from a map (set such that the initial target cumulative power supply WADTG decreases to the extent that the initial heater resistance value RHINT increases, i.e. to the extent that the initial heater temperature is high, the initial target cumulative power supply WADTG decreases to the extent that the initial element impedance ZDC decreases, i.e. to the extent that the initial element temperature is high, and the initial target cumulative power supply WADTG becomes 0 when the initial element temperature is a predetermined value, e.g. 100Ω or less) previously stored in a ROM as shown in FIG. 43 to obtain a linear interpolation.

Figure 30:
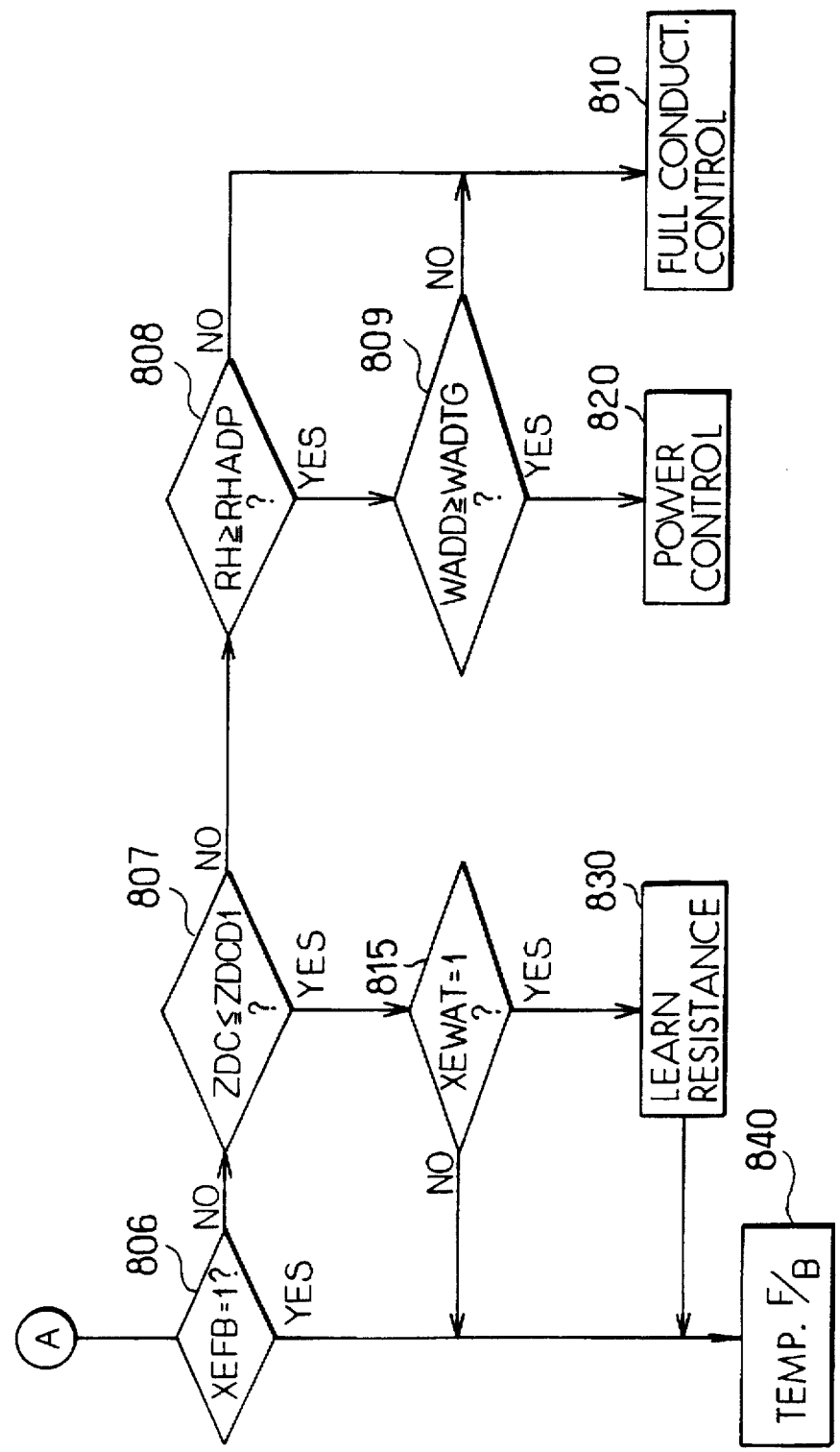
FIG. 30 is a flow chart showing an operation of the microcomputer in the eleventh embodiment of the present invention.
Figure 40:
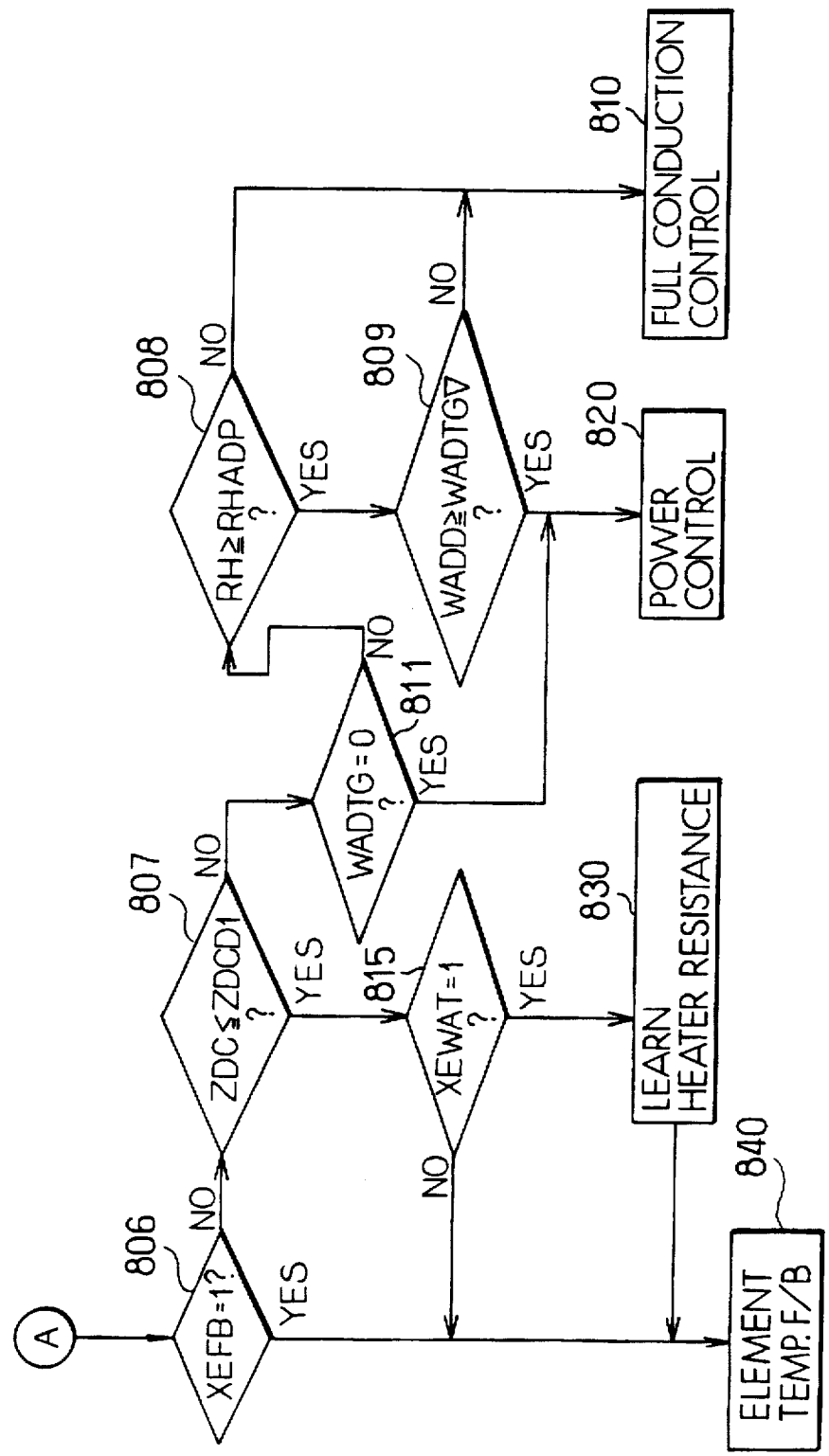
FIG. 40 is a flow chart showing an operation of the microcomputer in the twelfth embodiment of the present invention.

Process in FIG. 40 is used in place of process in FIG. 30, and where it is determined that ZDC is not equal to or less than ZDCD1 in step 807 step 811 is proceeded to and it is determined whether or not the initial target cumulative power supply WADTG is 0 or not. Where it is determined that the initial target cumulative power supply WADTG is not 0 step 808 is proceeded to, while where it is determined that the initial target cumulative power supply WADTG is 0 step 820 is proceeded to and power control is executed to forcibly terminate the execution of the full current supply control of step 810. Also, in step 809 it is determined whether or not the actual cumulative power WADD is greater than or equal to a corrected target cumulative power supply WADTGV.

Figure 36:
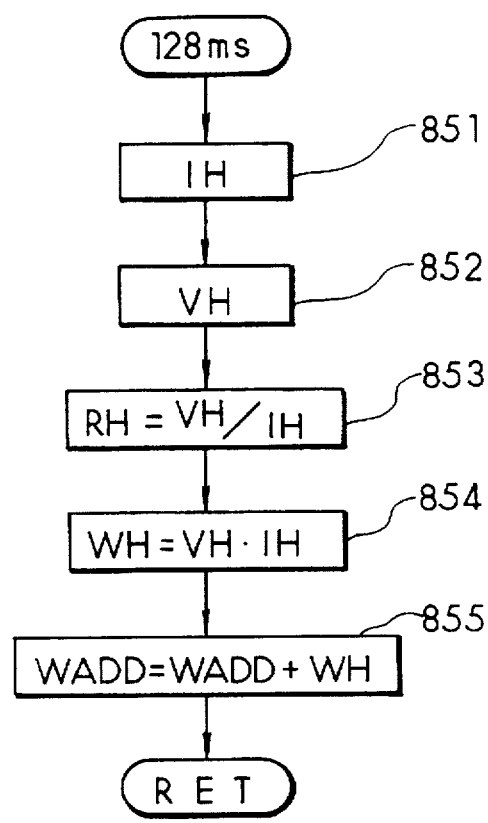
FIG. 36 is a flow chart showing an operation of a heater computation value process of the microcomputer in the eleventh embodiment of the present invention.
Figure 41:
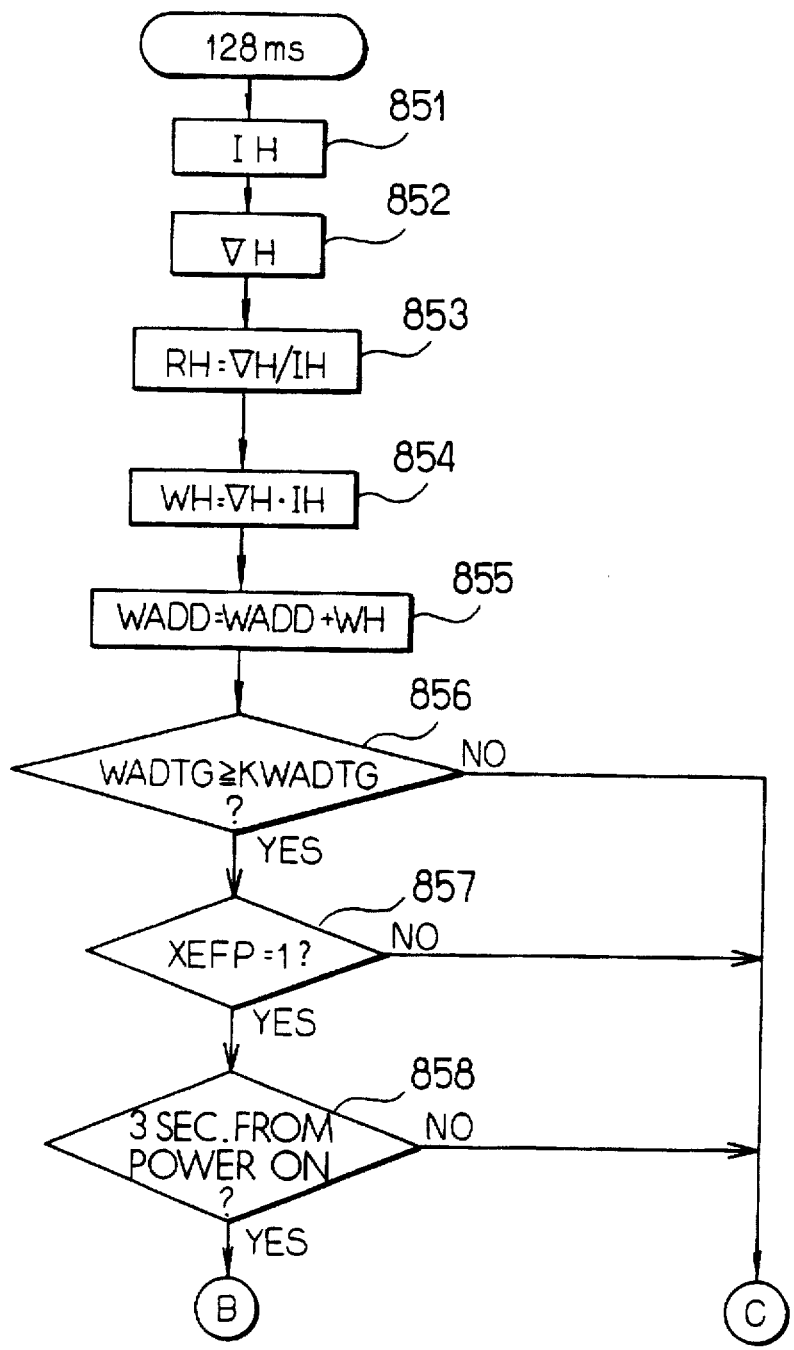
FIG. 41 is a flow chart showing an operation of a heater computation value process of the microcomputer in the twelfth embodiment of the present invention.
Figure 42:
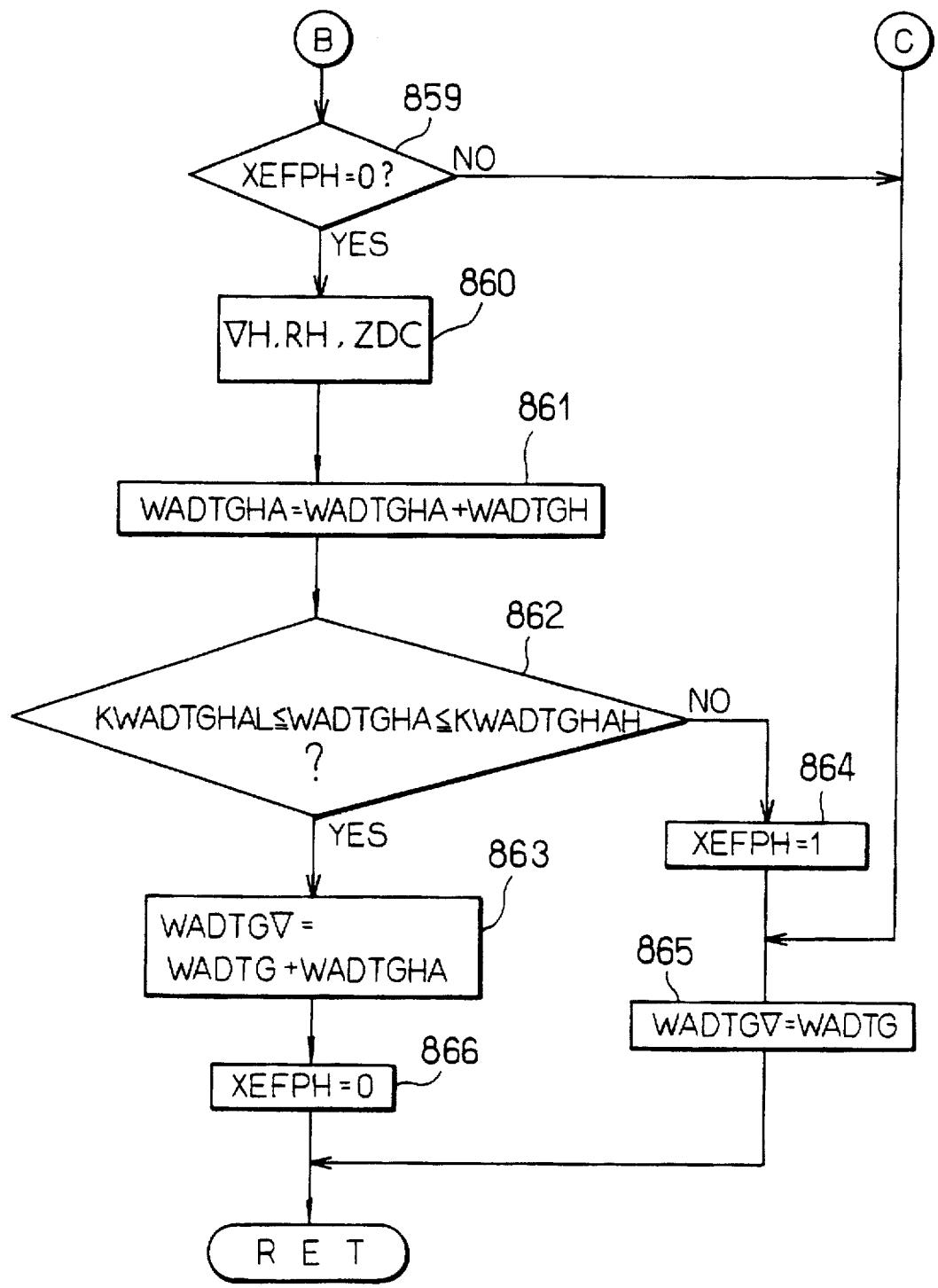
FIG. 42 is a flow chart showing an operation of a heater computation value process of the microcomputer in the twelfth embodiment of the present invention.

Processes in FIG. 41 and FIG. 42 are used in place of the process in FIG. 36, wherein step 856 is proceeded to after step 855. It is determined whether the initial target cumulative power supply WADTG is higher than a lower limit target cumulative power supply KWADTG. In step 856, if it is determined that the initial target cumulative power supply WADTG is higher than a lower limit target cumulative power supply KWADTG step 857 is proceeded to, while if it is determined that the initial target cumulative power supply WADTG is not higher than a lower limit target cumulative power supply KWADTG step 865 is proceeded to.

In step 857 it is determined whether the full conduction control flag XEFP is 1 or not, and if it is determined that the full conduction control flag XEFP is 1 step 858 is proceeded to, while if it is determined that the full conduction control flag is not 1 step 865 is proceeded to. In step 858 it is determined whether 3 seconds have elapsed from the ignition switch being turned ON or not, and if it is determined that 3 seconds have elapsed from the ignition switch being turned ON step 859 is proceeded to, while if it is determined that 3 seconds have not elapsed from the ignition switch being turned ON step 865 is proceeded to.

Figure 44:
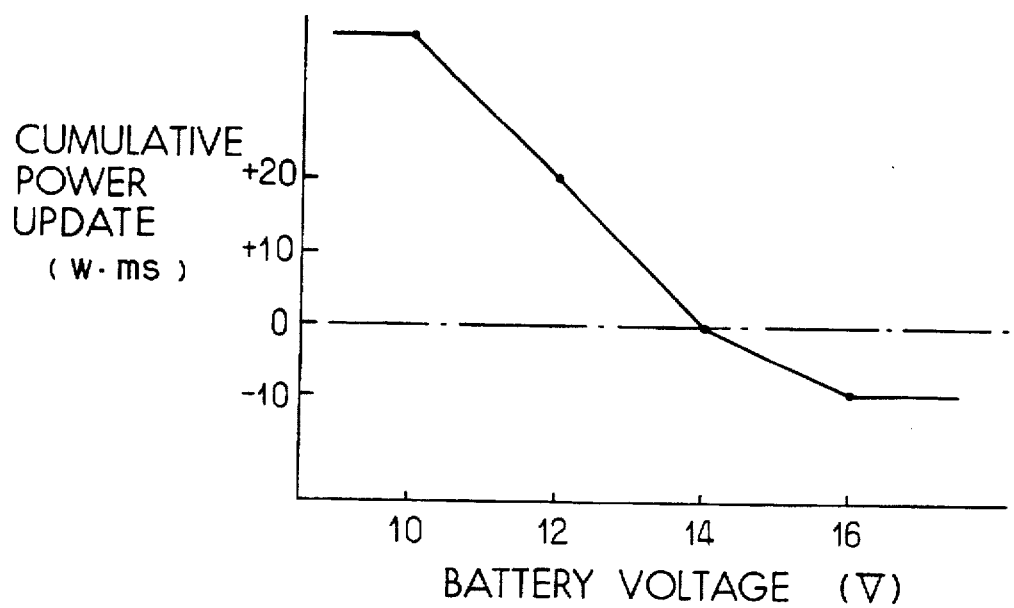
FIG. 44 is a characteristic graph showing a target cumulative power supply update amount with respect to a battery voltage.
Figure 45:
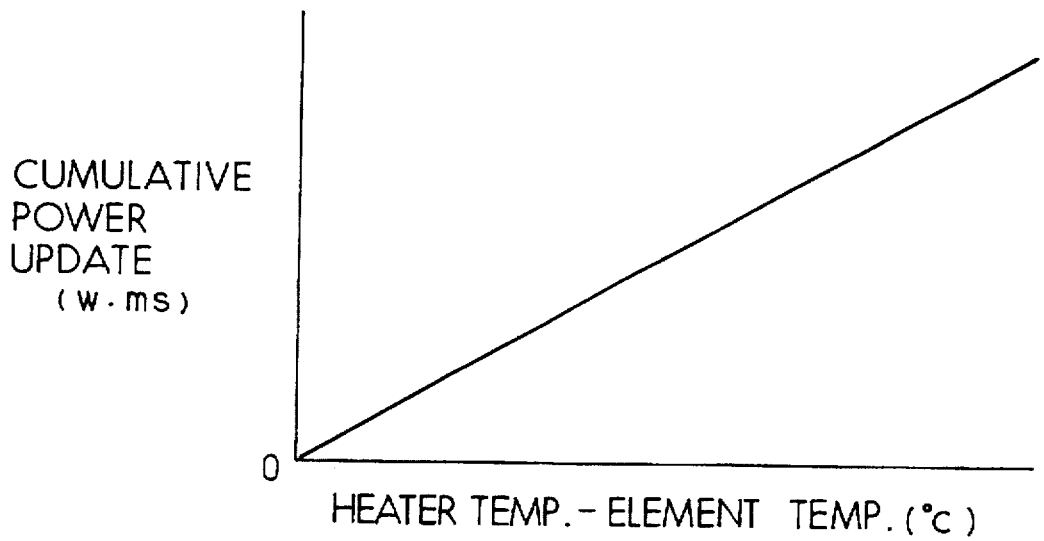
FIG. 45 is a characteristic graph showing a target cumulative power supply update amount with respect to heater temperature-element temperature.

In step 859 it is determined whether a guard out flag XEFPH is 0 or not. If it is determined that the guard out flag XEFPH is 0 step 860 is proceeded to, while if it is determined that the guard out flag XEFPH is not 0 step 865 is proceeded to. This guard out flag XEFPH is reset to 0 when the ignition switch is activated. In step 860 a target cumulative power supply update amount WADTGH is searched, according to the present battery voltage (heater voltage) VH, the present heater resistance RH and the present element impedance ZDC, from a data map previously stored in the ROM to obtain a linear interpolation. Here, the target cumulative power supply update amount with respect to the battery voltage (heater voltage) VH, as shown in FIG. 44, is set small to the extent that the battery voltage increases and, as shown in FIG. 45, the target cumulative power supply update amount is set so that it becomes large to the extent that the difference between heater temperature and element temperature increases.

In the next step 861, after the target cumulative power supply update amount WADTGH is added to a previous target cumulative power supply correction amount WADTGHA to obtain a present target cumulative power supply correction amount WADTGHA, step 862 is proceeded to. In step 862, it is determined whether the present target cumulative power supply correction amount WADTGHA falls within the limits of a lower limit target cumulative power supply correction amount KWADTGHAL and an upper limit present target cumulative power supply correction amount KWADTGHAH, and if it is determined that the present target cumulative power supply correction amount WADTGHA falls within the limits of the lower limit target cumulative power supply correction amount KWADTGHAL and the upper limit present target cumulative power supply correction amount KWADTGHAH, step 863 is proceeded to. If it is determined that it is not within those limits, step 864 is proceeded to. In step 863, after the present target cumulative power supply correction amount WADTGHA is added to the initial target cumulative power supply WADTG to obtain a corrected cumulative power supply WADTGV, step 866 is proceeded to, the guard out flag XEFPH is reset to 0 and the routine is exited.

In this way, during the full conduction control period, the target cumulative power supply correction amount WADTGHA is updated by addition using the target cumulative power supply update amount WADTGH in step 861 every 128 ms of the operation cycle, and by correcting the target cumulative power supply WADTG using this sum-updated target cumulative power supply correction amount WADTGHA, the target cumulative power supply WADTGV is corrected according to the battery voltage (heater voltage), heater temperature and element temperature difference, and full power supply interval. Here, even without definitely using both the maps of FIGS. 44 and 45, but using only either one thereof, the correction result of the target cumulative power supply can to a certain extent be attained.

After the guard out flag XEFPH is set to 1 in step 864, step 865 is proceeded to, the corrected target cumulative power supply WADTGV is set as the initial target cumulative power supply WADTG and the routine is exited.

Figure 29:
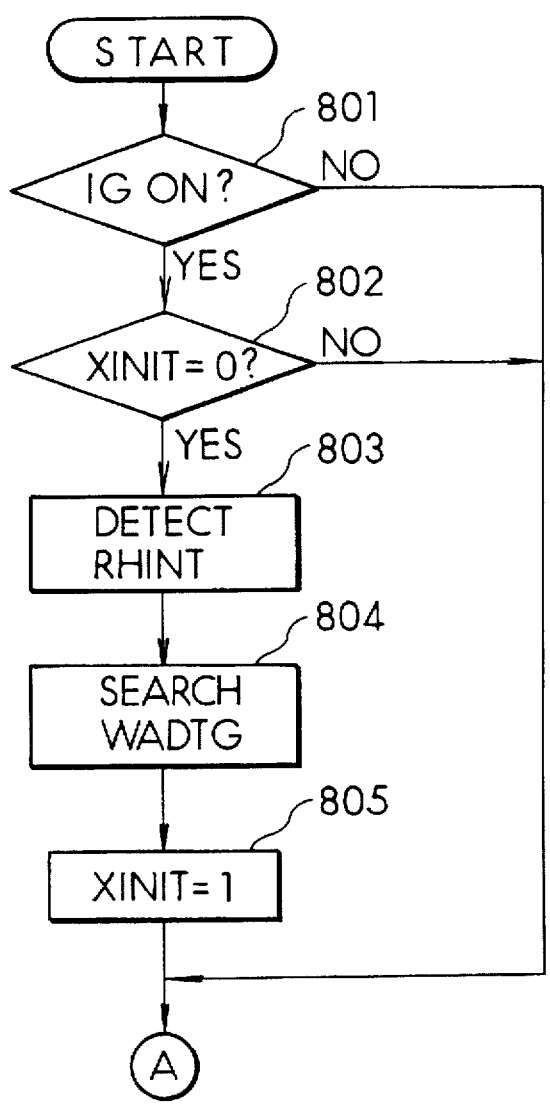
FIG. 29 is A flow chart showing the action of a microcomputer in a eleventh embodiment of the present invention.

In the twelfth embodiment, the flow chart of FIG. 29 of the eleventh embodiment may be used in place of FIG. 39, and the flow chart of FIG. 36 of the eleventh embodiment may be used in place of FIGS. 41 and 42.

[Other Embodiments]

In each of the above-described embodiments, although the heater temperature and element temperature are estimated by the heater resistance and element resistance, the heater temperature and element temperature may also be detected by a temperature sensor. However, it is necessary to use an expensive thermoelectric type temperature sensor having high durability and which can detect at high temperatures of 1200° C. or more.

Also, in each of the above-described embodiments, although 100% full power is supplied to the heater 26 at the time of current supply initiation to the heater 26, it is also permissible to supply power in the vicinity of full power within the range of 80 to 100%.

Figure 11:
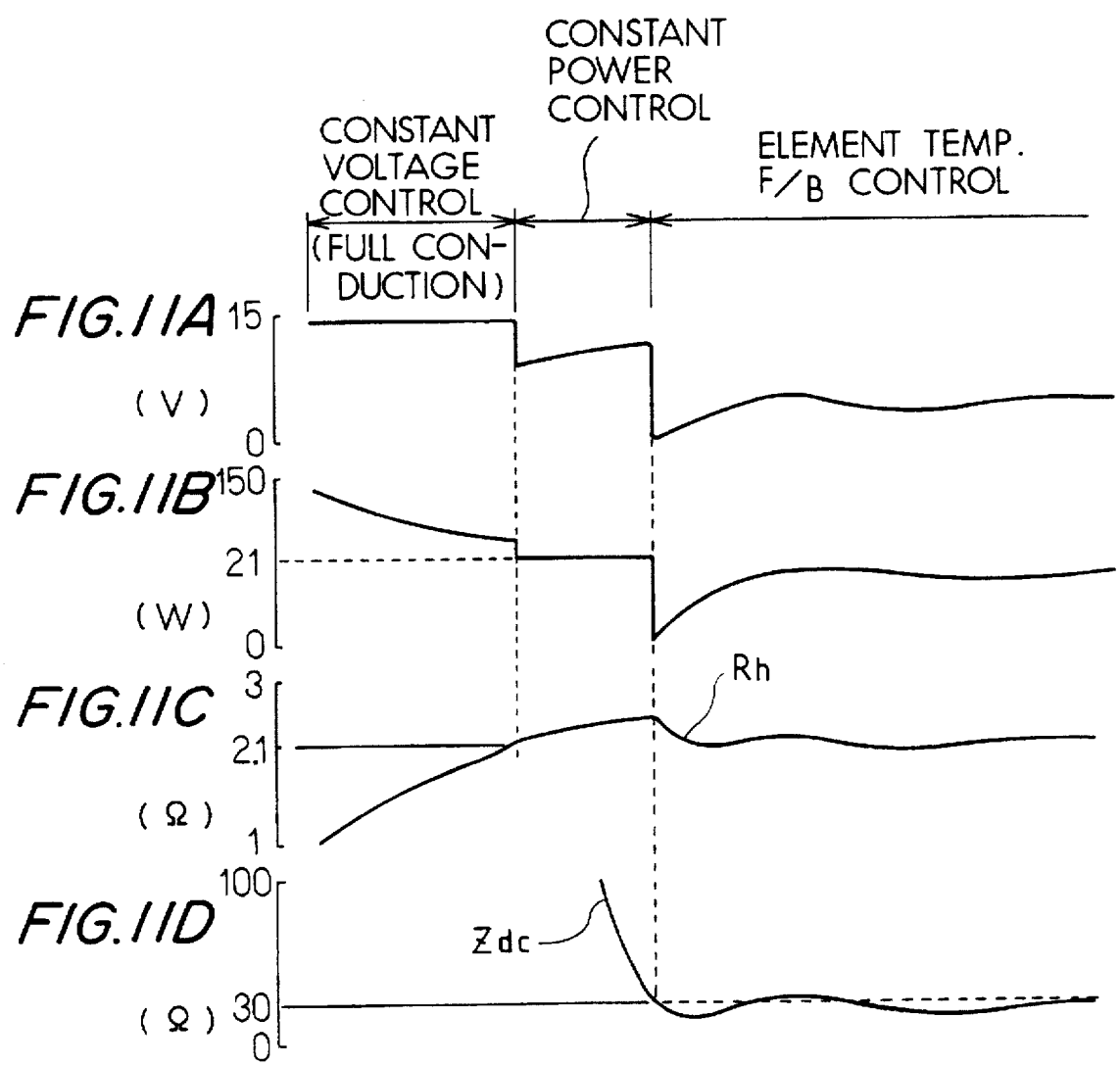
FIGS. 11A, 11B, 11C, and 11D are time charts explaining the operation of the first embodiment.

Also, power control in step 820 of FIGS. 30 and 40 is not limited to the heater power control according to the element impedance ZDC in FIG. 32, but as in the explanations of previously described FIGS. 1 to 10, any one of heater temperature upper limit hold control as shown in section (2) of FIG. 4, constant power control of FIG. 11, and power control of sections (2) and (3) of FIG. 22 may be used to control the heater power, and also, obtaining a target power by means of a data map based on engine revolutions and air intake pressure (or air intake amount) as described in Published Unexamined Japanese Patent Application No. S61-132851 to control heater power so that the heater temperature is in the vicinity of 1200° C. is also permissible. Also, in order to control so that the heater temperature is in the vicinity of 1200° C. by heater power control, it is also possible to omit the element temperature feedback control of step 840 of FIGS. 30 and 40 (naturally, using the element temperature feedback control can maintain the element temperature at a favorable predetermined value).

Also, it is also possible to combine the full power supply control based on the target cumulative power supply of the eleventh and twelfth embodiments with each type of full power supply control of the first to tenth embodiments.

In the above-described embodiments, the sensor current detection circuit 50, step 104, and steps 203, 822 and 842 constitutes element temperature detection means and element resistance detection means. The current detection resistor 82, step 104 and steps 206 and 853 constitutess heater temperature detection means and heater resistance detection means. Step 205 constitutes heater voltage detection means and heater current detection means. Steps 106, 111, 204, 211, 840 and 1050 constitute element temperature response current supply control means, steps 107, 107', 108, 207, 207', 208, 307, 810 and 1070 constitute full power supply means, steps 107, 107', 207 and 207'constitute initial heating temperature detection means, and step 307 constitutes timer means.

Also, steps 107, 107', 108 and 110 constitute heater temperature response current supply control means and heater temperature feedback control means as power control means, steps 213 to 215 and 217 constitute heater temperature response current supply control means and heater constant power control means as power control means, steps 105, 113 and 114 constitute element temperature feedback interrupt means, steps 115 and 118 constitute element temperature response voltage application termination means, steps 116, 116' and 118 constitute heater temperature response voltage application termination means, steps 212, 219 and 220 constitute initial duty setting means, steps 222, 222' and 223 constitute duty rapid reduction means, and steps 214 and 215 constitute duty gradual increase means.

Also, steps 401 to 415 constitute heater temperature estimation means, steps 401 to 407 constitute constant time heater temperature setting means, step 408 constitutes time constant setting means, step 413 constitutes heater temperature computation means, steps 501 to 512, 507', 520 to 527, 520' and 523' constitute target resistance value computation means, step 503 constitute heater resistance computation means, step 1030 constitutes power control means, steps 611 and 621 constitutes constant power supply means as power means, steps 609, 614, 619 and 820 constitute element temperature response power supply means as power supply means, and steps 605, 606, 616, and 701 to 706 constitutes determining means.

Further, step 803 constitutes resistance value detection means, step 804 constitutes target cumulative power supply setting means, step 808 constitutes heater resistance value determining means, step 809 constitutes cumulative power approach determining means, step 830 constitutes heater resistance learning means, step 849 constitutes power restriction means, step 855 constitutes actual cumulative power computation means, step 818 constitutes initial element temperature detection means, steps 804 and 811 constitutes full power supply termination means, and step 856 to step 866 constitute target cumulative power supply correction means.

As a result, as well as power in the vicinity of full power being supplied to the heater until the heater temperature at commencement of current supply reaches an initial heating temperature, by thereafter controlling the current supply to the heater such that the heater temperature becomes a predetermined value, not only can-the oxygen sensor be activated in a short time while preventing wire breakage to the heater, but there are also the advantages of superior durability of the heater and the element. Further, by controlling the current supply to the heater according to the element temperature after the element temperature of the oxygen sensor reaches a predetermined value, damage to the element can be prevented and the activation state of the oxygen sensor can be maintained without being affected by the surrounding environment such as the exhaust gas temperature etc.

What is claimed is:

1. A method of controlling a heater for heating an oxygen sensor, comprising:

a first step of supplying electrical power to the heater from commencement of current supply to the heater till a temperature of the heater reaches a set value set to a substantially low value from a threshold heat resistance temperature;

a second step of controlling current supply to the heater such that the temperature of the heater is kept at a temperature corresponding to the set value, upon the temperature of the heater reaching the set value by execution of the first step; and a third step of controlling feedback of the current supply to the heater such that an element temperature of the oxygen sensor is kept at a target value upon the element temperature of the oxygen sensor reaching the target value by execution of the second step.

2. A heater control apparatus for an oxygen sensor comprising:

element temperature detection means for detecting an element temperature of the oxygen sensor;

a heater for heating the oxygen sensor;

heater temperature detection means for detecting a temperature of the heater;

power supply means for supplying power from a power source in the heater from commencement of current supply to the heater until a temperature of the heater reaches an initial heating temperature;

heater temperature responsive current supply control means for controlling supply of current to the heater according to a heater temperature detected by the heater temperature detection means upon the temperature of the heater reaching the initial heating temperature by heating of the heater by the power supply means; and element temperature responsive current supply control means for controlling current supply to the heater according to the element temperature detected by the element temperature detection means upon the element temperature detected by the element temperature detection means reaching a predetermined value by heating of the heater by the heater temperature responsive current supply control means.

3. The heater control apparatus for an oxygen sensor according to claim 2, wherein:

the power supply means includes means for supplying 100% voltage to the heater from the power source, and the heater temperature responsive current supply control means includes heater temperature feedback control means for feedback controlling power supplied to the heater from the power source such that the heater temperature detected by the heater temperature detection means reaches the predetermined value.

4. The heater control apparatus for an oxygen sensor according to claim 2, wherein:

the element temperature detection means comprises means for detecting an internal resistance of the oxygen sensor as a value corresponding to the element temperature.

5. The heater control apparatus for an oxygen sensor according to claim 4, wherein:

the heater temperature responsive current supply control means comprises power control means for controlling a power supply to the heater to a predetermined value according to heater current and heater voltage, and the power control means includes constant power supply means for supplying a constant power to the heater where the internal resistance of the oxygen sensor is in an undetectable region as a value corresponding to element temperature, and element temperature responsive power supply means for supplying power to the heater according to the element temperature upon the internal resistance of the oxygen sensor becoming a detectable region as a value corresponding to element temperature.

6. The heater control apparatus for an oxygen sensor according to claim 5, further comprising:

determining means for selectively using one of a time lapse from commencement of current supply to the heater and a resistance value of the heater, based on the heater temperature at the time of current supply initiation to the heater, in a switching decision from control by the power supply means to control by the power control means.

7. The heater control apparatus for an oxygen sensor according to claim 2, wherein:

the power supply means includes initial heating temperature detection means for detecting when a heater temperature detected by the heater temperature detection means reaches the initial heating temperature.

8. The heater control apparatus for an oxygen sensor according to claim 2, wherein:

the power supply means includes timer means for detecting a lapse of time corresponding to the heater temperature reaching the initial heating temperature from commencement of current supply to the heater.

9. The heater control apparatus for an oxygen sensor according to claim 2, wherein:

the element temperature responsive current supply control means includes means for feedback controlling power supplied to the heater such that the element temperature of the oxygen sensor is kept at a target value.

10. The heater control apparatus for an oxygen sensor according to claim 9, wherein:

the initial heating temperature of the heater is set to a value higher than the target value of the element temperature and lower than a limit heat resistance heating temperature of the heater.

11. The heater control apparatus for an oxygen sensor according to claim 9, further comprising:

element temperature feedback interrupt means for, during feedback control execution by the element temperature responsive current supply control means, interrupting execution of feedback control by the element temperature responsive current supply control means when the element temperature of the oxygen sensor drops below the target value by more than a predetermined limit value and recommencing control by the heater temperature responsive current supply control means.

12. The heater control apparatus for an oxygen sensor according to claim 2, further comprising:

element temperature responsive voltage application termination means for terminating voltage application to the heater immediately upon the element temperature of the oxygen sensor reaching a value corresponding to a limit heat resistance temperature.

13. The heater control apparatus for an oxygen sensor according to claim 2, further comprising:

heater temperature responsive voltage application termination means for terminating voltage application to the heater immediately upon the temperature of the heater reaching a value corresponding to a limit heat resistance temperature.

14. The heater control apparatus for an oxygen sensor according to claim 2, further comprises:

heater voltage detection means for detecting a voltage applied to the heater, wherein the power supply means includes means for supplying 100% voltage to the heater from the power source, the heater temperature detection means comprises heater current detection means from detecting a current circulating to the heater, and the heater temperature responsive current supply control means comprises heater constant power control means for constant power controlling, at the predetermined value, a power supply to the heater according to the heater current detected by the heater current detection means and the heater voltage detected by the heater voltage detection means.

15. The heater control apparatus for an oxygen sensor according to claim 2, wherein:

the oxygen sensor is provided in an internal combustion engine exhaust path; and the heater temperature detection means includes heater temperature estimate means for estimating a temperature of the heater from revolutions of the internal combustion engine, one of air intake pressure and air intake amount, and heater voltage and heater current.

16. The heater control apparatus for an oxygen sensor according to one of claim 15, further comprising:

target resistance value computation means for calculating a target heater resistance value from the heater temperature estimated by the heater temperature estimate means; and heater resistance computing means for obtaining a heater resistance from the heater voltage and the heater current, wherein the heater temperature responsive current supply control means includes heater temperature feedback control means for feedback controlling power supplied to the heater from the power source such that the heater temperature obtained by the heater resistance computing means becomes a target heater resistance value.

17. The heater control apparatus for an oxygen sensor according to claim 15, wherein:

the heater temperature estimate means includes constant time heater temperature estimate means for readily determining heater temperature in a steady state of the internal combustion engine from the revolutions, one of an air intake pressure and an air intake amount, and the heater voltage and the heater current.

18. The heater control apparatus for an oxygen sensor according to claim 15, wherein the heater temperature estimate means includes:

constant time heater temperature determining means for readily determining heater temperature in a steady state of the internal combustion engine from the revolutions, one of an air intake pressure and an air intake amount, and the heater voltage and the heater current;

time constant determining means for readily determining a time constant at a transition time of the internal combustion engine from one of the revolutions, the air intake pressure and the air intake amount; and heater temperature determining means for computing a temperature of the heater using heater temperature in the steady state and a time constant at the transition time.

19. The heater control apparatus for an oxygen sensor according to claim 18, wherein:

the time constant determining means has two time constants, one time constant being with respect to changes in the revolutions and one of the air intake pressure and air intake amount, and another time constant being with respect to power supply changes to the heater.

20. A heater control apparatus for an oxygen sensor comprising:

element resistance detection means for detecting an element internal resistance of the oxygen sensor;

a heater for heating the oxygen sensor;

heater current detection means for detecting a current of the heater;

heater voltage detection means for detecting a voltage of the heater;

full power supply means for supplying power from a power source in the heater from commencement of current supply to the heater until a temperature of the heater reaches an initial heating temperature;

a heater constant power control means for controlling power supply to the heater such that it is kept at a predetermined constant power, according to the heater current detected by the heater current detection means and a heater voltage detected by the heater voltage detection means, upon the temperature of the heater reaching the initial heating temperature by heating of the heater by the power supply means; and element temperature responsive current supply control means for controlling current supply to the heater according to the internal resistance of the element detected by the element resistance detection means upon the element resistance detected by the element resistance detection means reaching a predetermined value corresponding to a predetermined element temperature by heating of the heater by the heater constant power control means.

21. The heater control apparatus for an oxygen sensor according to claim 20, wherein:

the heater constant power control means includes means for controlling power supply to the heater by duty controlling a voltage supplied to the heater; and duty rapid reduction means is provided for rapidly reducing the duty controlled by the heater constant power control means upon the temperature of the heater reaching a value corresponding to a limit heat resistance temperature.

22. The heater control apparatus for an oxygen sensor according to claim 21, wherein the heater constant power control means includes:

initial duty setting means for setting a relatively small initial duty with respect to the heater immediately after the temperature of the heater reaches the initial heating temperature by heating the heater by the power supply means; and duty gradual increase means for gradually increasing a duty such that the power supply of the duty gradually approaches a target power supply by means of the initial duty set by the initial duty setting means.

23. A heater control apparatus for an oxygen sensor, comprising:

element temperature detection means for detecting an element temperature of the oxygen sensor;

a heater for heating the oxygen sensor;

first power supply means for supplying power from a power source in the heater from commencement of current supply to the heater until a temperature of the heater reaches an initial heating temperature;

element temperature responsive power supply means for supplying power to the heater according to the element temperature detected by the element temperature detection means such that the heater temperature is maintained at a predetermined temperature upon the temperature of the heater reaching the initial heating temperature by heating of the heater by the first power supply means; and element temperature responsive current supply control means for controlling current supply to the heater according to the element temperature detected by the element temperature detection means upon the element temperature detected by the element temperature detection means reaching a predetermined value by heating of the heater by the element temperature responsive power supply means.

24. The heater control apparatus for an oxygen sensor according to claim 23, further comprising:

target cumulative power setting means for setting a target cumulative power supply to the heater according to whether the temperature of the heater is the initial heating temperature;

actual cumulative power computation means for calculating an actual power supply cumulative value to the heater; and cumulative power approach determination means for determining that the initial heating temperature has been reached upon the actual power supply cumulative value computed by the actual cumulative power computation means reaching the target cumulative power supply set by the target cumulative power setting means from commencement of current supply to the heater.

25. The heater control apparatus for an oxygen sensor according to claim 23, further comprising:

target cumulative power setting means for setting a target cumulative power supply to the heater according to whether the temperature of the heater is the initial heating temperature;

actual cumulative power computation means for calculating an actual power supply cumulative value to the heater; and cumulative power approach determination means for determining that the initial heating temperature has been reached upon the actual power supply cumulative value computed by the actual cumulative power computation means reaching the target cumulative power supply set by the target cumulative power setting means from commencement of current supply to the heater.

26. A heater control apparatus for an oxygen sensor comprising:

a heater for heating the oxygen sensor;

target cumulative power setting means for setting a target cumulative power supply to the heater according to whether the temperature of the heater is in an initial heating temperature;

actual cumulative power computation means for calculating an actual power supply cumulative value to the heater;

cumulative power approach determination means for determining whether the actual power supply cumulative value computed by the actual cumulative power computation means has reached the target cumulative power supply set by the target cumulative power setting means from commencement of current supply to the heater;

power supply means for supplying a predetermined amount of power from a power source in the heater from commencement of current supply to the heater until the actual power supply cumulative value has been determined by the cumulative power approach determination means as reaching the target cumulative power supply; and power control means for controlling power supplied to the heater such that the heater temperature reaches a predetermined value, upon the actual power supply cumulative value being determined by the cumulative power approach determination means as reaching the target cumulative power supply by heating of the heater by the power supply means.

27. The heater control apparatus for an oxygen sensor according to claim 26, further comprising:

heater resistance value detection means for detecting an internal resistance of the heater as heater temperature, wherein the target cumulative power supply of the target cumulative power supply means is set according to an initial resistance value of the heater detected by the heater resistance value detection means.

28. The heater control apparatus for an oxygen sensor according to claim 27, further comprising:

heater resistance learning means for learning a heater resistance value detected by the heater resistance value detecting means at a time when power supplied to the heater is controlled by the power control means; and heater resistance value determination means for determining whether a heater resistance detected by the heater resistance detection means is greater than the heater resistance learning value learned by the heater resistance learning means, wherein the power supply to the heater is switched from the power supply means to the power control means upon the heater resistance being determined by the heater resistance value determining means as being greater than the heater resistance learning value and the actual power supply cumulative value being determined by the cumulative power approach determining means as having reached the target cumulative power supply.

29. The heater control apparatus for an oxygen sensor according to claim 28, further comprising:

element temperature responsive current supply control means for controlling current supply to the heater according to an element temperature of the oxygen sensor such that the element temperature maintains a predetermined temperature, upon the element temperature detected by the element temperature detection means reaching the predetermined value by heating of the heater by the power control means.

30. The heater control apparatus for an oxygen sensor according to claim 29, further comprising:

power restriction means for restricting power to the heater when a heater resistance value detected by the heater resistance value detection means is above an upper limit value set according to the heater resistance learning value learned by the heater resistance learning means, when current supply to the heater is being controlled by the element temperature responsive current supply control means.

31. The heater control apparatus for an oxygen sensor according to claim 29, wherein:

the heater resistance learning means learns the heater resistance value detected by the heater resistance value detection means when the element temperature reaches a predetermined value and current supply to the heater is switched from the power control means to the element temperature responsive current supply control means.

32. The heater control apparatus for an oxygen sensor according to claim 26, further comprising:

element temperature detection means for detecting an element temperature of the oxygen sensor, wherein the power control means includes element temperature responsive power supply means for supplying power to the heater according to the element temperature detected by the element temperature detection means such that the heater temperature maintains a predetermined temperature.

33. The heater control apparatus for an oxygen sensor according to claim 32, wherein the element temperature detection means comprises:

means for detecting an internal resistance of the oxygen sensor as a value corresponding to the element temperature.

34. The heater control apparatus for an oxygen sensor according to claim 26, further comprising:

initial element temperature detection means for detecting an initial element temperature of the oxygen sensor; and power supply termination means for terminating supply of said predetermined amount of power to the heater by the said predetermined amount of power supply means when an initial element temperature of the heater detected by the initial element temperature detection means is above a predetermined value.

35. The heater control apparatus for an oxygen sensor according to claim 26, further comprising:

target cumulative power supply correction means for correcting the target cumulative power supply set by the target cumulative power supply means according to at least one of the heater temperature, the element temperature of the oxygen sensor, a supply time of said predetermined amount of power to the heater by the power supply means and an applied voltage to the heater.

36. The heater control apparatus for an oxygen sensor according to claim 35, wherein:

the target cumulative power supply correction means corrects the target cumulative power supply according to a difference between the heater temperature and the element temperature of the oxygen sensor, and the supply time of full power to the heater by the said predetermined amount of power supply means.

37. The heater control apparatus for an oxygen sensor according to claim 35, wherein:

the target cumulative power supply correction means corrects the target cumulative power supply according to the applied voltage to the heater and the supply time of said predetermined amount of power to the heater by the power supply means.

38. The heater control apparatus for an oxygen sensor according to claim 26, further comprising:

initial element temperature detection means for detecting an initial element temperature of the oxygen sensor, wherein the target cumulative power supply of the target cumulative power supply means is set according to an initial element temperature of the heater detected by the initial element temperature detection means.

* * * * *